(12) United States Patent
Turner et al.

(10) Patent No.: US 9,290,800 B2
(45) Date of Patent: Mar. 22, 2016

(54) TARGETED ROLLING CIRCLE AMPLIFICATION

(71) Applicants: Pacific Biosciences of California, Inc., Menlo Park, CA (US); The Regents of the University of California, Oakland, CA (US)

(72) Inventors: Stephen W. Turner, Menlo Park, CA (US); Thang Pham, Mountain View, CA (US); Paul Hagerman, Davis, CA (US)

(73) Assignees: Pacific Biosciences of California, Inc., Menlo Park, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/208,451

(22) Filed: Mar. 13, 2014

(65) Prior Publication Data

US 2014/0295498 A1    Oct. 2, 2014

Related U.S. Application Data

(60) Provisional application No. 61/799,237, filed on Mar. 15, 2013.

(51) Int. Cl.
    *C12Q 1/68*      (2006.01)
    *C07H 21/04*     (2006.01)
(52) U.S. Cl.
    CPC .................................. *C12Q 1/6853* (2013.01)
(58) Field of Classification Search
    CPC ........... C12Q 1/6853; C12Q 2521/301; C12Q 2525/131; C12Q 2531/125
    See application file for complete search history.

(56) References Cited

U.S. PATENT DOCUMENTS

| | | |
|---|---|---|
| 4,965,188 A | 10/1990 | Mullis et al. |
| 5,001,050 A | 3/1991 | Blanco et al. |
| 5,198,543 A | 3/1993 | Blanco et al. |
| 5,576,204 A | 11/1996 | Blanco et al. |
| 6,451,563 B1 | 9/2002 | Wittig et al. |
| 6,498,023 B1 | 12/2002 | Abarzua et al. |
| 7,033,764 B2 | 4/2006 | Korlach et al. |

(Continued)

FOREIGN PATENT DOCUMENTS

| | | |
|---|---|---|
| EP | 2428588 A2 | 2/2003 |
| EP | 2391731 B1 | 1/2013 |

(Continued)

OTHER PUBLICATIONS

Callow, M.J. et al., Nucl. Acids Res., vol. 32, e21, pp. 1-6 (2004).*

(Continued)

*Primary Examiner* — Teresa E Strzelecka
(74) *Attorney, Agent, or Firm* — Monica Elrod-Erickson

(57) ABSTRACT

Methods for amplifying a desired target region of a nucleic acid through rolling circle amplification with a strand-displacing polymerase are provided. Concatameric hairpin products are resolved with endonuclease digestion, and the resulting amplified product hairpins or fragments can be circularized and employed as templates in a subsequent round of amplification. The methods are effective for targeted amplification of even highly repetitive sequences. Compositions, kits, and systems related to or useful in the methods are also described.

21 Claims, 6 Drawing Sheets

(56) References Cited

U.S. PATENT DOCUMENTS

| | | | |
|---|---|---|---|
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,368,265 | B2 | 5/2008 | Brenner et al. |
| 8,153,375 | B2 | 4/2012 | Travers et al. |
| 8,257,954 | B2 | 9/2012 | Clark et al. |
| 8,309,330 | B2 | 11/2012 | Travers et al. |
| 8,420,366 | B2 | 4/2013 | Clark et al. |
| 8,455,193 | B2 | 6/2013 | Travers et al. |
| 8,530,164 | B2 | 9/2013 | Patel et al. |
| 8,658,364 | B2 | 2/2014 | Pham et al. |
| 2009/0298075 | A1* | 12/2009 | Travers et al. ............... 435/6 |
| 2009/0305419 | A1 | 12/2009 | Miller |
| 2010/0093555 | A1 | 4/2010 | Bjornson et al. |
| 2011/0287512 | A1 | 11/2011 | Paschon et al. |
| 2012/0034602 | A1 | 2/2012 | Emig et al. |
| 2013/0217007 | A1 | 8/2013 | Kamtekar et al. |
| 2014/0094374 | A1 | 4/2014 | Kamtekar et al. |
| 2014/0134610 | A1 | 5/2014 | Pham et al. |

FOREIGN PATENT DOCUMENTS

| | | | |
|---|---|---|---|
| WO | WO 2007/075873 A2 | 7/2007 | |
| WO | WO 2007/075987 A2 | 7/2007 | |
| WO | WO 2007/076057 A2 | 7/2007 | |
| WO | WO 2008/051530 A2 | 5/2008 | |
| WO | WO 2010/086626 A1 | 8/2010 | |
| WO | WO 2012/017210 A1 | 2/2012 | |
| WO | WO 2013/148400 A1 | 10/2013 | |
| WO | WO 2014/071070 A1 | 5/2014 | |

OTHER PUBLICATIONS

Osborne, R.J. et al., Nucl. Acids Res., vol. 36, e24, pp. 1-7 (2008).*

Fujii, et al. (2004) "One-step random mutagenesis by error-prone rolling circle amplification." *Nucleic Acids Research*, 32(19):e145.

Fujii, et al. (2006) "Error-prone rolling circle amplification: the simplest random mutagenesis protocol." *Nature Protocols*, 1(5):2493-2497.

Gaj, et al. (2013) "A comprehensive approach to zinc-finger recombinase customization enables genomic targeting in human cells." *Nucleic Acids Research*, 41(6):3937-3946.

Huovinen, et al. (2011) "Enhanced error-prone RCA mutagenesis by concatamer resolution." *Plasmid*, 66(1):47-51.

Lacroix, et al. (2011) "FLP/FRT-mediated conditional mutagenesis in pre-erythrocytic stages of Plasmodium berghei." *Nature Protocols*, 6(9):1412-1428.

Meijer, et al. (2001) "Φ29 Family of Phages." *Microbiology and Molecular Biology Reviews*, 65(2):261-287.

Pinard, et al. (2006) "Assessment of whole genome amplification-induced bias through high-throughput, massively parallel whole genome sequencing." BMC Genomics 7:216.

Silander and Saarela (2008) "Whole Genome Amplification with Phi29 DNA Polymerase to Enable Genetic or Genomic Analysis of Samples of Low DNA Yield." *Methods in Molecular Biology*, 439:1-18.

Travers, et al. (2010) "A flexible and efficient template format for circular consensus sequencing and SNP detection." *Nucleic Acids Research*, 38(15):e159.

* cited by examiner

SEQUENCE LISTING

<160> NUMBER OF SEQ ID NOS: 9

<210> SEQ ID NO 1
<211> LENGTH: 575
<212> TYPE: PRT
<213> ORGANISM: Bacteriophage phi-29

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365
```

```
Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 572
<212> TYPE: PRT
<213> ORGANISM: Bacteriophage M2Y

<400> SEQUENCE: 2

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175
```

```
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
        195                 200                 205
Pro Lys Leu Ser Leu Pro Met Asp Lys Glu Ile Arg Lys Ala Tyr Arg
    210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
        275                 280                 285
Phe Glu Leu Lys Glu Gly Tyr Ile Pro Thr Ile Gln Ile Lys Lys Asn
    290                 295                 300
Pro Phe Phe Lys Gly Asn Glu Tyr Leu Lys Asn Ser Gly Val Glu Pro
305                 310                 315                 320
Val Glu Leu Tyr Leu Thr Asn Val Asp Leu Glu Leu Ile Gln Glu His
                325                 330                 335
Tyr Glu Leu Tyr Asn Val Glu Tyr Ile Asp Gly Phe Lys Phe Arg Glu
            340                 345                 350
Lys Thr Gly Leu Phe Lys Asp Phe Ile Asp Lys Trp Thr Tyr Val Lys
        355                 360                 365
Thr His Glu Glu Gly Ala Lys Lys Gln Leu Ala Lys Leu Met Leu Asn
    370                 375                 380
Ser Leu Tyr Gly Lys Phe Ala Ser Asn Pro Asp Val Thr Gly Lys Val
385                 390                 395                 400
Pro Tyr Leu Lys Asp Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
        435                 440                 445
Ile Ile Tyr Cys Asp Thr Asp Ser Ile His Leu Thr Gly Thr Glu Val
    450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Val Lys Glu Val Asp Gly Lys Leu Lys Glu
            500                 505                 510
Cys Ser Pro Asp Glu Ala Thr Thr Thr Lys Phe Ser Val Lys Cys Ala
        515                 520                 525
Gly Met Thr Asp Thr Ile Lys Lys Lys Val Thr Phe Asp Asn Phe Ala
    530                 535                 540
Val Gly Phe Ser Ser Met Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 3
<211> LENGTH: 572
```

<212> TYPE: PRT
<213> ORGANISM: Bacteriophage B103

<400> SEQUENCE: 3

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

```
Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Arg
            530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 4
<211> LENGTH: 578
<212> TYPE: PRT
<213> ORGANISM: Bacteriophage GA-1

<400> SEQUENCE: 4

Met Ala Arg Ser Val Tyr Val Cys Asp Phe Glu Thr Thr Thr Asp Pro
1               5                   10                  15

Glu Asp Cys Arg Leu Trp Ala Trp Gly Trp Met Asp Ile Tyr Asn Thr
            20                  25                  30

Asp Lys Trp Ser Tyr Gly Glu Asp Ile Asp Ser Phe Met Glu Trp Ala
            35                  40                  45

Leu Asn Ser Asn Ser Asp Ile Tyr Phe His Asn Leu Lys Phe Asp Gly
        50                  55                  60

Ser Phe Ile Leu Pro Trp Trp Leu Arg Asn Gly Tyr Val His Thr Glu
65                  70                  75                  80

Glu Asp Arg Thr Asn Thr Pro Lys Glu Phe Thr Thr Thr Ile Ser Gly
            85                  90                  95

Met Gly Gln Trp Tyr Ala Val Asp Val Cys Ile Asn Thr Arg Gly Lys
            100                 105                 110

Asn Lys Asn His Val Val Phe Tyr Asp Ser Leu Lys Lys Leu Pro Phe
        115                 120                 125

Lys Val Glu Gln Ile Ala Lys Gly Phe Gly Leu Pro Val Leu Lys Gly
        130                 135                 140

Asp Ile Asp Tyr Lys Lys Tyr Arg Pro Val Gly Tyr Val Met Asp Asp
145                 150                 155                 160

Asn Glu Ile Glu Tyr Leu Lys His Asp Leu Leu Ile Val Ala Leu Ala
            165                 170                 175

Leu Arg Ser Met Phe Asp Asn Asp Phe Thr Ser Met Thr Val Gly Ser
            180                 185                 190

Asp Ala Leu Asn Thr Tyr Lys Glu Met Leu Gly Val Lys Gln Trp Glu
```

```
                195                 200                 205
Lys Tyr Phe Pro Val Leu Ser Leu Lys Val Asn Ser Glu Ile Arg Lys
210                 215                 220

Ala Tyr Lys Gly Gly Phe Thr Trp Val Asn Pro Lys Tyr Gln Gly Glu
225                 230                 235                 240

Thr Val Tyr Gly Gly Met Val Phe Asp Val Asn Ser Met Tyr Pro Ala
                245                 250                 255

Met Met Lys Asn Lys Leu Leu Pro Tyr Gly Pro Val Met Phe Lys
        260                 265                 270

Gly Glu Tyr Lys Lys Asn Val Glu Tyr Pro Leu Tyr Ile Gln Gln Val
            275                 280                 285

Arg Cys Phe Glu Leu Lys Lys Asp Lys Ile Pro Cys Ile Gln Ile
290                 295                 300

Lys Gly Asn Ala Arg Phe Gly Gln Asn Glu Tyr Leu Ser Thr Ser Gly
305                 310                 315                 320

Asp Glu Tyr Val Asp Leu Tyr Val Thr Asn Val Asp Trp Glu Leu Ile
                325                 330                 335

Lys Lys His Tyr Asp Ile Phe Glu Glu Phe Ile Gly Gly Phe Met
            340                 345                 350

Phe Lys Gly Phe Ile Gly Phe Phe Asp Glu Tyr Ile Asp Arg Phe Met
            355                 360                 365

Glu Ile Lys Asn Ser Pro Asp Ser Ser Ala Glu Gln Ser Leu Gln Ala
370                 375                 380

Lys Leu Met Leu Asn Ser Leu Tyr Gly Lys Phe Ala Thr Asn Pro Asp
385                 390                 395                 400

Ile Thr Gly Lys Val Pro Tyr Leu Asp Glu Asn Gly Val Leu Lys Phe
                405                 410                 415

Arg Lys Gly Glu Leu Lys Glu Arg Asp Pro Val Tyr Thr Pro Met Gly
            420                 425                 430

Cys Phe Ile Thr Ala Tyr Ala Arg Glu Asn Ile Leu Ser Asn Ala Gln
            435                 440                 445

Lys Leu Tyr Pro Arg Phe Ile Tyr Ala Asp Thr Asp Ser Ile His Val
450                 455                 460

Glu Gly Leu Gly Glu Val Asp Ala Ile Lys Asp Val Ile Asp Pro Lys
465                 470                 475                 480

Lys Leu Gly Tyr Trp Asp His Glu Ala Thr Phe Gln Arg Ala Arg Tyr
                485                 490                 495

Val Arg Gln Lys Thr Tyr Phe Ile Glu Thr Thr Trp Lys Glu Asn Asp
            500                 505                 510

Lys Gly Lys Leu Val Val Cys Glu Pro Gln Asp Ala Thr Lys Val Lys
            515                 520                 525

Pro Lys Ile Ala Cys Ala Gly Met Ser Asp Ala Ile Lys Glu Arg Ile
530                 535                 540

Arg Phe Asn Glu Phe Lys Ile Gly Tyr Ser Thr His Gly Ser Leu Lys
545                 550                 555                 560

Pro Lys Asn Val Leu Gly Gly Val Val Leu Met Asp Tyr Pro Phe Ala
                565                 570                 575

Ile Lys

<210> SEQ ID NO 5
<211> LENGTH: 566
<212> TYPE: PRT
<213> ORGANISM: Bacteriophage AV-1
```

<400> SEQUENCE: 5

```
Met Val Arg Gln Ser Thr Ile Ala Ser Pro Ala Arg Gly Val Arg
1               5                   10                  15

Arg Ser His Lys Lys Val Pro Ser Phe Cys Ala Asp Phe Glu Thr Thr
            20                  25                  30

Thr Asp Glu Asp Asp Cys Arg Val Trp Ser Trp Gly Ile Ile Gln Val
        35                  40                  45

Gly Lys Leu Gln Asn Tyr Val Asp Gly Ile Ser Leu Asp Gly Phe Met
50                  55                  60

Ser His Ile Ser Glu Arg Ala Ser His Ile Tyr Phe His Asn Leu Ala
65                  70                  75                  80

Phe Asp Gly Thr Phe Ile Leu Asp Trp Leu Leu Lys His Gly Tyr Arg
                85                  90                  95

Trp Thr Lys Glu Asn Pro Gly Val Lys Glu Phe Thr Ser Leu Ile Ser
            100                 105                 110

Arg Met Gly Lys Tyr Tyr Ser Ile Thr Val Val Phe Glu Thr Gly Phe
        115                 120                 125

Arg Val Glu Phe Arg Asp Ser Phe Lys Lys Leu Pro Met Ser Val Ser
    130                 135                 140

Ala Ile Ala Lys Ala Phe Asn Leu His Asp Gln Lys Leu Glu Ile Asp
145                 150                 155                 160

Tyr Glu Lys Pro Arg Pro Ile Gly Tyr Ile Pro Thr Glu Gln Glu Lys
                165                 170                 175

Arg Tyr Gln Arg Asn Asp Val Ala Ile Val Ala Gln Ala Leu Glu Val
            180                 185                 190

Gln Phe Ala Glu Lys Met Thr Lys Leu Thr Ala Gly Ser Asp Ser Leu
        195                 200                 205

Ala Thr Tyr Lys Lys Met Thr Gly Lys Leu Phe Ile Arg Arg Phe Pro
    210                 215                 220

Ile Leu Ser Pro Glu Ile Asp Thr Glu Ile Arg Lys Ala Tyr Arg Gly
225                 230                 235                 240

Gly Phe Thr Tyr Ala Asp Pro Arg Tyr Ala Lys Lys Leu Asn Gly Lys
                245                 250                 255

Gly Ser Val Tyr Asp Val Asn Ser Leu Tyr Pro Ser Val Met Arg Thr
            260                 265                 270

Ala Leu Leu Pro Tyr Gly Glu Pro Ile Tyr Ser Glu Gly Ala Pro Arg
        275                 280                 285

Thr Asn Arg Pro Leu Tyr Ile Ala Ser Ile Thr Phe Thr Ala Lys Leu
    290                 295                 300

Lys Pro Asn His Ile Pro Cys Ile Gln Ile Lys Lys Asn Leu Ser Phe
305                 310                 315                 320

Asn Pro Thr Gln Tyr Leu Glu Glu Val Lys Glu Pro Thr Thr Val Val
                325                 330                 335

Ala Thr Asn Ile Asp Ile Glu Leu Trp Lys Lys His Tyr Asp Phe Lys
            340                 345                 350

Ile Tyr Ser Trp Asn Gly Thr Phe Glu Phe Arg Gly Ser His Gly Phe
        355                 360                 365

Phe Asp Thr Tyr Val Asp His Phe Met Glu Ile Lys Lys Asn Ser Thr
    370                 375                 380

Gly Gly Leu Arg Gln Ile Ala Lys Leu His Leu Asn Ser Leu Tyr Gly
385                 390                 395                 400

Lys Phe Ala Thr Asn Pro Asp Ile Thr Gly Lys His Pro Thr Leu Lys
                405                 410                 415
```

```
Asp Asn Arg Val Ser Leu Val Met Asn Glu Pro Glu Thr Arg Asp Pro
            420                 425                 430

Val Tyr Thr Pro Met Gly Val Phe Ile Thr Ala Tyr Ala Arg Lys Lys
            435                 440                 445

Thr Ile Ser Ala Ala Gln Asp Asn Tyr Glu Thr Phe Ala Tyr Ala Asp
            450                 455                 460

Thr Asp Ser Leu His Leu Ile Gly Pro Thr Thr Pro Pro Asp Ser Leu
465                 470                 475                 480

Trp Val Asp Pro Val Glu Leu Gly Ala Trp Lys His Glu Ser Ser Phe
                485                 490                 495

Thr Lys Ser Val Tyr Ile Arg Ala Lys Gln Tyr Ala Glu Glu Ile Gly
            500                 505                 510

Gly Lys Leu Asp Val His Ile Ala Gly Met Pro Arg Asn Val Ala Ala
            515                 520                 525

Thr Leu Thr Leu Glu Asp Met Leu His Gly Gly Thr Trp Asn Gly Lys
            530                 535                 540

Leu Ile Pro Val Arg Val Pro Gly Gly Thr Val Leu Lys Asp Thr Thr
545                 550                 555                 560

Phe Thr Leu Lys Ile Asp
            565

<210> SEQ ID NO 6
<211> LENGTH: 568
<212> TYPE: PRT
<213> ORGANISM: Bacteriophage CP-1

<400> SEQUENCE: 6

Met Thr Cys Tyr Tyr Ala Gly Asp Phe Glu Thr Thr Thr Asn Glu Glu
1               5                   10                  15

Glu Thr Glu Val Trp Leu Ser Cys Phe Ala Lys Val Ile Asp Tyr Asp
            20                  25                  30

Lys Leu Asp Thr Phe Lys Val Asn Thr Ser Leu Glu Asp Phe Leu Lys
            35                  40                  45

Ser Leu Tyr Leu Asp Leu Asp Lys Thr Tyr Thr Glu Thr Gly Glu Asp
50                  55                  60

Glu Phe Ile Ile Phe Phe His Asn Leu Lys Phe Asp Gly Ser Phe Leu
65                  70                  75                  80

Leu Ser Phe Phe Leu Asn Asn Asp Ile Glu Cys Thr Tyr Phe Ile Asn
                85                  90                  95

Asp Met Gly Val Trp Tyr Ser Ile Thr Leu Glu Phe Pro Asp Phe Thr
            100                 105                 110

Leu Thr Phe Arg Asp Ser Leu Lys Ile Leu Asn Phe Ser Ile Ala Thr
            115                 120                 125

Met Ala Gly Leu Phe Lys Met Pro Ile Ala Lys Gly Thr Thr Pro Leu
            130                 135                 140

Leu Lys His Lys Pro Glu Val Ile Lys Pro Glu Trp Ile Asp Tyr Ile
145                 150                 155                 160

His Val Asp Val Ala Ile Leu Ala Arg Gly Ile Phe Ala Met Tyr Tyr
                165                 170                 175

Glu Glu Asn Phe Thr Lys Tyr Thr Ser Ala Ser Glu Ala Leu Thr Glu
            180                 185                 190

Phe Lys Arg Ile Phe Arg Lys Ser Lys Arg Lys Phe Arg Asp Phe Phe
            195                 200                 205

Pro Ile Leu Asp Glu Lys Val Asp Asp Phe Cys Arg Lys His Ile Val
```

Gly Ala Gly Arg Leu Pro Thr Leu Lys His Arg Gly Arg Thr Leu Asn
225                 230                 235                 240

Gln Leu Ile Asp Ile Tyr Asp Ile Asn Ser Met Tyr Pro Ala Thr Met
            245                 250                 255

Leu Gln Asn Ala Leu Pro Ile Gly Ile Pro Lys Arg Tyr Lys Gly Lys
                260                 265                 270

Pro Lys Glu Ile Lys Glu Asp His Tyr Tyr Ile Tyr His Ile Lys Ala
            275                 280                 285

Asp Phe Asp Leu Lys Arg Gly Tyr Leu Pro Thr Ile Gln Ile Lys Lys
        290                 295                 300

Lys Leu Asp Ala Leu Arg Ile Gly Val Arg Thr Ser Asp Tyr Val Thr
305                 310                 315                 320

Thr Ser Lys Asn Glu Val Ile Asp Leu Tyr Leu Thr Asn Phe Asp Leu
                325                 330                 335

Asp Leu Phe Leu Lys His Tyr Asp Ala Thr Ile Met Tyr Val Glu Thr
            340                 345                 350

Leu Glu Phe Gln Thr Glu Ser Asp Leu Phe Asp Asp Tyr Ile Thr Thr
        355                 360                 365

Tyr Arg Tyr Lys Lys Glu Asn Ala Gln Ser Pro Ala Glu Lys Gln Lys
        370                 375                 380

Ala Lys Ile Met Leu Asn Ser Leu Tyr Gly Lys Phe Gly Ala Lys Ile
385                 390                 395                 400

Ile Ser Val Lys Lys Leu Ala Tyr Leu Asp Asp Lys Gly Ile Leu Arg
                405                 410                 415

Phe Lys Asn Asp Asp Glu Glu Val Gln Pro Val Tyr Ala Pro Val
            420                 425                 430

Ala Leu Phe Val Thr Ser Ile Ala Arg His Phe Ile Ile Ser Asn Ala
        435                 440                 445

Gln Glu Asn Tyr Asp Asn Phe Leu Tyr Ala Asp Thr Asp Ser Leu His
        450                 455                 460

Leu Phe His Ser Asp Ser Leu Val Leu Asp Ile Asp Pro Ser Glu Phe
465                 470                 475                 480

Gly Lys Trp Ala His Glu Gly Arg Ala Val Lys Ala Lys Tyr Leu Arg
                485                 490                 495

Ser Lys Leu Tyr Ile Glu Glu Leu Ile Gln Glu Asp Gly Thr Thr His
            500                 505                 510

Leu Asp Val Lys Gly Ala Gly Met Thr Pro Glu Ile Lys Glu Lys Ile
        515                 520                 525

Thr Phe Glu Asn Phe Val Ile Gly Ala Thr Phe Glu Gly Lys Arg Ala
530                 535                 540

Ser Lys Gln Ile Lys Gly Gly Thr Leu Ile Tyr Glu Thr Thr Phe Lys
545                 550                 555                 560

Ile Arg Glu Thr Asp Tyr Leu Val
                565

<210> SEQ ID NO 7
<211> LENGTH: 583
<212> TYPE: PRT
<213> ORGANISM: Artificial Sequence
<220> FEATURE:
<223> OTHER INFORMATION: His-tagged bacteriophage M2Y DNA polymerase

<400> SEQUENCE: 7

Met Ser Arg Lys Met Phe Ser Cys Asp Phe Glu Thr Thr Thr Lys Leu

-continued

```
  1               5                  10                 15
Asp Asp Cys Arg Val Trp Ala Tyr Gly Tyr Met Glu Ile Gly Asn Leu
                20                 25                 30

Asp Asn Tyr Lys Ile Gly Asn Ser Leu Asp Glu Phe Met Gln Trp Val
                35                 40                 45

Met Glu Ile Gln Ala Asp Leu Tyr Phe His Asn Leu Lys Phe Asp Gly
                50                 55                 60

Ala Phe Ile Val Asn Trp Leu Glu Gln His Gly Phe Lys Trp Ser Asn
 65                70                 75                 80

Glu Gly Leu Pro Asn Thr Tyr Asn Thr Ile Ile Ser Lys Met Gly Gln
                85                 90                 95

Trp Tyr Met Ile Asp Ile Cys Phe Gly Tyr Lys Gly Lys Arg Lys Leu
                100                105                110

His Thr Val Ile Tyr Asp Ser Leu Lys Lys Leu Pro Phe Pro Val Lys
                115                120                125

Lys Ile Ala Lys Asp Phe Gln Leu Pro Leu Lys Gly Asp Ile Asp
                130                135                140

Tyr His Thr Glu Arg Pro Val Gly His Glu Ile Thr Pro Glu Glu Tyr
145                150                155                160

Glu Tyr Ile Lys Asn Asp Ile Glu Ile Ile Ala Arg Ala Leu Asp Ile
                165                170                175

Gln Phe Lys Gln Gly Leu Asp Arg Met Thr Ala Gly Ser Asp Ser Leu
                180                185                190

Lys Gly Phe Lys Asp Ile Leu Ser Thr Lys Lys Phe Asn Lys Val Phe
                195                200                205

Pro Lys Leu Ser Leu Pro Met Asp Lys Glu Ile Arg Lys Ala Tyr Arg
                210                215                220

Gly Gly Phe Thr Trp Leu Asn Asp Lys Tyr Lys Glu Lys Glu Ile Gly
225                230                235                240

Glu Gly Met Val Phe Asp Val Asn Ser Leu Tyr Pro Ser Gln Met Tyr
                245                250                255

Ser Arg Pro Leu Pro Tyr Gly Ala Pro Ile Val Phe Gln Gly Lys Tyr
                260                265                270

Glu Lys Asp Glu Gln Tyr Pro Leu Tyr Ile Gln Arg Ile Arg Phe Glu
                275                280                285

Phe Glu Leu Lys Glu Gly Tyr Ile Pro Thr Ile Gln Ile Lys Lys Asn
                290                295                300

Pro Phe Phe Lys Gly Asn Glu Tyr Leu Lys Asn Ser Gly Val Glu Pro
305                310                315                320

Val Glu Leu Tyr Leu Thr Asn Val Asp Leu Glu Leu Ile Gln Glu His
                325                330                335

Tyr Glu Leu Tyr Asn Val Glu Tyr Ile Asp Gly Phe Lys Phe Arg Glu
                340                345                350

Lys Thr Gly Leu Phe Lys Asp Phe Ile Asp Lys Trp Thr Tyr Val Lys
                355                360                365

Thr His Glu Glu Gly Ala Lys Lys Gln Leu Ala Lys Leu Met Leu Asn
                370                375                380

Ser Leu Tyr Gly Lys Phe Ala Ser Asn Pro Asp Val Thr Gly Lys Val
385                390                395                400

Pro Tyr Leu Lys Asp Asp Gly Ser Leu Gly Phe Arg Val Gly Asp Glu
                405                410                415

Glu Tyr Lys Asp Pro Val Tyr Thr Pro Met Gly Val Phe Ile Thr Ala
                420                425                430
```

```
Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
                500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Ala
        530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys Gly His His His
                565                 570                 575

His His His His His His His
            580

<210> SEQ ID NO 8
<211> LENGTH: 45
<212> TYPE: DNA
<213> ORGANISM: Artificial Sequence
<220> FEATURE:
<223> OTHER INFORMATION: oligonucleotide hairpin adapter

<400> SEQUENCE: 8
atctctctct tttcctcctc ctccgttgtt gttgttgaga gagat          45

<210> SEQ ID NO 9
<211> LENGTH: 15
<212> TYPE: DNA
<213> ORGANISM: Artificial Sequence
<220> FEATURE:
<223> OTHER INFORMATION: oligonucleotide primer

<400> SEQUENCE: 9
aacggaggag gagga          15
```

TARGETED ROLLING CIRCLE AMPLIFICATION

CROSS-REFERENCE TO RELATED APPLICATIONS

This application is a non-provisional utility patent application claiming priority to and benefit of the following prior provisional patent application: U.S. Ser. No. 61/799,237, filed Mar. 15, 2013, entitled "TARGETED ROLLING CIRCLE AMPLIFICATION" by Stephen W. Turner et al., which is incorporated herein by reference in its entirety for all purposes.

STATEMENT AS TO RIGHTS TO INVENTIONS MADE UNDER FEDERALLY SPONSORED RESEARCH AND DEVELOPMENT

Not applicable.

FIELD OF THE INVENTION

The invention relates to methods, compositions, and polymerase enzymes for amplifying target nucleic acids.

BACKGROUND OF THE INVENTION

Many techniques in modern biology require nucleic acid amplification as an initial step. As just a few examples, DNA cloning, DNA fingerprinting, sequencing, and molecularly-based disease detection and diagnosis often rely on amplification of the nucleic acid target of interest. The polymerase chain reaction (PCR) is widely used for nucleic acid amplification and has been successfully employed to amplify a variety of nucleic acid targets. However, PCR is not ideal for amplification of all possible targets.

In particular, PCR amplification of targets containing short repeated sequences (e.g., dinucleotides, trinucleotides, etc.) can be hampered by problems such as stutter. A stutter product is a PCR artifact that is one or more repeat units shorter or longer than the original target sequence. Stutter products typically increase in quantity as the length of the target sequence increases, and can introduce uncertainty into attempts to determine copy number of such repeated sequences. Additionally, palindromic sequences and sequences with extreme GC content are difficult and sometimes impossible to amplify.

Methods for amplifying nucleic acid targets, including targets containing repeated sequence elements, are thus desirable. The present invention meets these and other needs by providing, inter alia, methods and compositions for nucleic acid amplification. A complete understanding of the invention will be obtained upon review of the following.

SUMMARY OF THE INVENTION

The present invention provides methods of amplifying nucleic acids, as well as compositions, kits, and systems for amplifying nucleic acids.

A first general class of embodiments provides methods of amplifying a nucleic acid target region. In the methods, a nucleic acid template is provided. The template is a circular nucleic acid having a double-stranded central region that comprises a first polynucleotide sequence and a second polynucleotide sequence complementary to the first polynucleotide sequence. The first and second polynucleotide sequences collectively comprise the target region and a recognition site for a first site-specific endonuclease. The circular nucleic acid also includes two single-stranded hairpin end regions and comprises a first primer binding sequence.

A first primer is bound to the first primer binding sequence, and polymerase-mediated template-directed primer extension of the first primer is performed with a polymerase comprising strand displacement activity, thereby producing a first nucleic acid product that comprises at least two copies of the first polynucleotide sequence and the second polynucleotide sequence, at least one copy of each of which is not base paired to the template. Typically, a copy of the first polynucleotide sequence that is not base paired to the template is base paired to a copy of the second polynucleotide sequence. Typically, the first nucleic acid product comprises at least two copies of the complement of the template, at least one copy of which is not base paired to the template. The first nucleic acid product typically contains more than two copies of the first polynucleotide sequence and the second polynucleotide sequence, for example, at least three copies (at least two copies of each of which are not base paired to the template), at least five copies, at least 10 copies, at least 20 copies, at least 30 copies, at least 40 copies, or at least 50 copies.

The first product is cut with the first endonuclease, and at least one first product hairpin is released. The first product hairpin has at least one single-stranded hairpin end region, a double-stranded region that comprises the target region, a free 5' terminus, and a free 3' terminus. The at least one first product hairpin can be circularized, thereby producing at least one first circular progeny nucleic acid comprising the target region.

The first primer binding sequence can be located in one of the two single-stranded hairpin end regions of the template, or it can be partially or completely within the double-stranded region. In one class of embodiments, the recognition site for the first endonuclease is proximal to the first primer binding sequence.

In one aspect, the site-specific endonuclease is a restriction endonuclease, and circularizing the at least one first product hairpin comprises ligating a first hairpin adapter to the first product hairpin. In another aspect, the site-specific endonuclease is a nicking endonuclease, and circularizing the at least one first product hairpin comprises ligating the 5' terminus of the first product hairpin intramolecularly to the 3' terminus.

The first circular progeny nucleic acid can include a second primer binding sequence, e.g., for determining the sequence of the target region or for performing a second round of amplification. In embodiments in which a second round of amplification is performed, the first circular progeny nucleic acid comprises a second primer binding sequence and a recognition site for a second site-specific endonuclease. A second primer is bound to the second primer binding sequence, and polymerase-mediated template-directed primer extension of the second primer is performed with a polymerase comprising strand displacement activity, thereby producing a second nucleic acid product comprising at least two copies of the first polynucleotide sequence and the second polynucleotide sequence, at least one copy of each of which is not base paired to the first circular progeny nucleic acid. The second product is cut with the second endonuclease, and at least one second product hairpin having at least one single-stranded hairpin end region, a double-stranded region that comprises the target region, a free 5' terminus, and a free 3' terminus is released. The at least one second product hairpin can be circularized if desired, thereby producing at least one second circular progeny nucleic acid.

The first and second primers and primer binding sequences can be the same, or more typically, can be different. In one class of embodiments, the first primer binding sequence and the complement of the second primer binding sequence are in one of the two single-stranded hairpin end regions of the template, and the second primer binding sequence and the complement of the first primer binding sequence are thus in one single-stranded hairpin end region of the first circular progeny nucleic acid. In another class of embodiments, the second primer binding sequence comprises the recognition site for the first endonuclease. In such embodiments, the second primer binding site can be created upon circularization of the first product hairpin.

Different endonucleases can be employed in different rounds of amplification, or the same endonuclease can be employed. Thus, optionally the recognition site for the second endonuclease is identical to the recognition site for the first endonuclease and the first and second endonucleases are the same enzyme.

The various steps (primer binding, primer extension, cutting with endonuclease, ligation, etc.) can be performed sequentially or concurrently. For example, cutting with the endonuclease can be performed after primer extension is complete, or it can be performed concurrently with the primer extension reaction. Similarly, circularization of the product hairpins can be performed after cutting with the endonuclease is complete, or cutting and circularization can be performed concurrently. As another example, primer extension, cutting, and circularization can be performed concurrently. Optionally, when multiple rounds of amplification are performed, the primer extension, cutting, and circularizing steps to produce the first circular progeny nucleic acid and the primer extension, cutting, and circularizing steps to produce the second circular progeny nucleic acid are performed in a single reaction mixture. In embodiments in which cutting is performed concurrently with primer extension and/or circularization, the nucleic acid template and/or the first circular progeny nucleic acid are optionally not subject to being cut by the first endonuclease (for example, they can be protected by methylation or inclusion of nonstandard nucleotides or linkages).

In one aspect, the strand-displacing polymerase is a recombinant Φ29-type polymerase. For example, the polymerase can be a recombinant DNA polymerase comprising an amino acid sequence that is at least 80% identical to SEQ ID NO:1 or at least 80% identical to SEQ ID NO:2.

The methods can be used to accurately and consistently amplify even target regions containing repetitive sequences. Thus, the target region optionally comprises at least five tandem copies of a mononucleotide, dinucleotide, trinucleotide, tetranucleotide, or pentanucleotide repeat sequence, e.g., at least 10, at least 20, at least 30, at least 40, at least 50, at least 60, at least 70, at least 80, at least 90, at least 100, at least 150, at least 200, or at least 250 copies of the repeat sequence. Amplified target can be used in essentially any desired application. For example, at least a portion of the target region in the first circular progeny nucleic acid (or second or any subsequent circular progeny nucleic acid) can be subjected to template-directed sequencing by synthesis. In embodiments where introduction of random mutations rather than accurate amplification is desirable, in one or more rounds of amplification primer extension is performed under mutagenic conditions.

Another general class of embodiments provides methods of amplifying a nucleic acid target region. In the methods, a nucleic acid template is provided. The template is a circular nucleic acid having a double-stranded central region and two single-stranded hairpin end regions. The double-stranded central region comprises the target region and comprises a recognition site for a first restriction endonuclease. The nucleic acid comprises a first primer binding sequence, to which a first primer is bound. Polymerase-mediated template-directed primer extension of the first primer is performed with a polymerase comprising strand displacement activity, thereby producing a first nucleic acid product comprising at least two copies of the complement of the template, at least one copy of which is not base paired to the template. Typically, the first nucleic acid product comprises at least three copies of the template, at least two copies of which are not base paired to the template. The first product is digested with the first restriction endonuclease, and at least one first product hairpin having one single-stranded hairpin end region and a double-stranded region that comprises the target region is released. A first hairpin adapter can be ligated to the first product hairpin, thereby producing at least one first circular progeny nucleic acid.

Optionally, the first primer binding sequence is in one of the two single-stranded hairpin end regions. In one class of embodiments, the recognition site for the first restriction endonuclease is proximal to the first primer binding sequence. In another class of embodiments, the recognition site for the first restriction endonuclease is distal to the first primer binding sequence, and digesting the first product with the first restriction endonuclease and releasing at least one first product hairpin comprises digesting the first product with the first restriction endonuclease, denaturing resulting double-stranded nucleic acid segments, and annealing resulting complementary single-stranded DNA segments, thereby releasing the at least one first product hairpin.

The steps can be repeated to achieve a greater degree of amplification. Thus, in one class of embodiments, the first circular progeny nucleic acid comprises a second primer binding sequence and a recognition site for a second restriction endonuclease. The first and second primer binding sequences can be the same or different, and the recognition sites for the first and second restriction endonucleases (and the first and second restriction endonucleases themselves) can be the same or different. A second primer is bound to the second primer binding sequence, and polymerase-mediated template-directed primer extension of the second primer is performed with a polymerase comprising strand displacement activity, thereby producing a second nucleic acid product comprising at least two copies of the complement of the first copy nucleic acid, at least one copy of which is not base paired to the first circular progeny nucleic acid. The second product is digested with the second restriction endonuclease, and at least one second product hairpin having one single-stranded hairpin end region and a double-stranded region that comprises the target region is released. Optionally, a second hairpin adapter is ligated to the second product hairpin, thereby producing at least one second circular progeny nucleic acid.

In one class of embodiments, the first hairpin adapter comprises the second primer binding sequence. In other embodiments, the second primer binding sequence is formed by ligation of the first hairpin adapter to the first product hairpin. The first product hairpin and the first hairpin adapter can have blunt ends, or the first hairpin adapter can have a single-stranded overhang that is complementary to a single-stranded overhang on the first product hairpin. In one class of embodiments, the cleavage site for the first restriction endonuclease is within the target region.

The various steps (primer binding, primer extension, digestion with the restriction enzyme, ligation, etc.) can be performed sequentially or concurrently. For example, restriction digestion can be performed after primer extension is complete, or it can be performed concurrently with the primer extension reaction. Similarly, ligation of the adapter to the product hairpins can be performed after digestion is complete, or digestion and ligation can be performed concurrently. As another example, primer extension, digestion, and ligation can be performed concurrently. Optionally, when multiple rounds of amplification are performed, the primer extension, digesting, and ligating steps to produce the first circular progeny nucleic acid and the primer extension, digesting, and ligating steps to produce the second circular progeny nucleic acid are performed in a single reaction mixture. In embodiments in which digestion is performed concurrently with primer extension and/or ligation, the nucleic acid template and/or the first circular progeny nucleic acid are optionally not subject to being cleaved by the first restriction endonuclease (for example, they can be protected by methylation or inclusion of nonstandard nucleotides or linkages).

Essentially all of the features noted for the methods above apply to these embodiments as well, as relevant, for example, with respect to the polymerase employed, type of target region, subsequent manipulation (e.g., sequencing) of the amplified target region, performance of primer extension under mutagenic conditions, and/or the like.

Another general class of embodiments provides methods of amplifying a nucleic acid target region. In the methods, a nucleic acid template is provided. The template is a circular nucleic acid having a double-stranded central region and two single-stranded hairpin end regions. The double-stranded central region comprises the target region and comprises a recognition site for a first nicking endonuclease. The nucleic acid comprises a first primer binding sequence, to which a first primer is bound. Polymerase-mediated template-directed primer extension of the first primer is performed with a polymerase comprising strand displacement activity, thereby producing a first nucleic acid product comprising at least two copies of the complement of the template, at least one copy of which is not base paired to the template. Typically, the first nucleic acid product comprises at least three copies of the template, at least two copies of which are not base paired to the template. The first product is nicked with the first nicking endonuclease, and at least one first product hairpin having at least one single-stranded hairpin end region, a double-stranded region that comprises the target region, a free 5' terminus, and a free 3' terminus is released. The 5' terminus of the first product hairpin can be ligated intramolecularly to the 3' terminus, thereby producing at least one first circular progeny nucleic acid.

Optionally, the first primer binding sequence is in one of the two single-stranded hairpin end regions. In one class of embodiments, the recognition site for the first nicking endonuclease is proximal to the first primer binding sequence.

The steps can be repeated to achieve a greater degree of amplification. Thus, in one class of embodiments, the first circular progeny nucleic acid comprises a second primer binding sequence and a recognition site for a second nicking endonuclease. The first and second primer binding sequences can be the same or different, and the recognition sites for the first and second nicking endonucleases (and the first and second nicking endonucleases themselves) can be the same or different. A second primer is bound to the second primer binding sequence, and polymerase-mediated template-directed primer extension of the second primer is performed with a polymerase comprising strand displacement activity, thereby producing a second nucleic acid product comprising at least two copies of the complement of the first copy nucleic acid, at least one copy of which is not base paired to the first circular progeny nucleic acid. The second product is nicked with the second nicking endonuclease, and at least one second product hairpin having at least one single-stranded hairpin end region, a double-stranded region that comprises the target region, a free 5' terminus, and a free 3' terminus is released. The 5' terminus of the second product hairpin can be ligated intramolecularly to the 3' terminus, thereby producing at least one second circular progeny nucleic acid.

The second primer binding sequence is optionally in one of the two single-stranded hairpin end regions, e.g., in the same single-stranded hairpin end region of the first circular progeny nucleic acid as is the complement of the first primer binding sequence. In one class of embodiments, the recognition site for the second nicking endonuclease is proximal to the second primer binding sequence. The second primer binding sequence can formed by ligation of the termini of the first product hairpin. Thus, in one class of embodiments, the second primer binding sequence comprises the recognition site for the first nicking endonuclease.

The various steps (primer binding, primer extension, nicking, ligation, etc.) can be performed sequentially or concurrently. For example, nicking can be performed after primer extension is complete, or it can be performed concurrently with the primer extension reaction. Similarly, ligation of the adapter to the product hairpins can be performed after nicking is complete, or nicking and ligation can be performed concurrently. As another example, primer extension, nicking, and ligation can be performed concurrently. Optionally, when multiple rounds of amplification are performed, the primer extension, nicking, and ligating steps to produce the first circular progeny nucleic acid and the primer extension, nicking, and ligating steps to produce the second circular progeny nucleic acid are performed in a single reaction mixture.

Essentially all of the features noted for the methods above apply to these embodiments as well, as relevant, for example, with respect to the polymerase employed, type of target region, subsequent manipulation (e.g., sequencing) of the amplified target region, performance of primer extension under mutagenic conditions, and/or the like.

Another general class of embodiments provides methods of amplifying a nucleic acid target region. In the methods, a nucleic acid template is provided. The template is a circular nucleic acid having a double-stranded central region and two single-stranded hairpin end regions. The double-stranded central region comprises a first polynucleotide sequence and a second polynucleotide sequence complementary to the first polynucleotide sequence. The first and second polynucleotide sequences collectively comprise the target region, a recognition site for a first restriction endonuclease, and a recognition site for a second restriction endonuclease. The target region is flanked by the recognition sites. The circular nucleic acid comprises a first primer binding sequence, to which a first primer is bound. Optionally, the first primer binding sequence is in one of the two single-stranded hairpin end regions in the template.

Polymerase-mediated template-directed primer extension of the first primer is performed with a polymerase comprising strand displacement activity, thereby producing a first nucleic acid product comprising at least two copies of the first polynucleotide sequence and the second polynucleotide sequence, at least one copy of each of which is not base paired to the template. Typically, a copy of the first polynucleotide sequence that is not base paired to the template is base paired to a copy of the second polynucleotide sequence. Typically, the first nucleic acid product comprises at least two copies of the complement of the template, at least one copy of which is not base paired to the template. The first nucleic acid product typically contains more than two copies of the first polynucleotide sequence and the second polynucleotide sequence, for example, at least three copies (at least two copies of each of which are not base paired to the template), at least five copies, at least 10 copies, at least 20 copies, at least 30 copies, at least 40 copies, or at least 50 copies. The first product is digested with the first and second restriction endonucleases, and at least one first product fragment having a double-stranded region is released.

The product fragment can be circularized if desired, for example, by ligating a first hairpin adapter to one end of the first product fragment and ligating a second hairpin adapter to the other end of the first product fragment, thereby producing at least one first circular progeny nucleic acid. In one class of embodiments, the recognition site for the second restriction endonuclease has the same sequence as the recognition site for the first restriction endonuclease, and the first and second restriction endonucleases are the same enzyme. In this class of embodiments, the same type of hairpin adapter is optionally ligated to both ends of the fragment. Thus, the methods can include ligating a first hairpin adapter to one end of the product fragment and ligating a second hairpin adapter to the other end of the product fragment, wherein the first and second hairpin adapters have the same sequence. In another class of embodiments, the recognition site for the second restriction endonuclease is different from the recognition site for the first restriction endonuclease. Optionally, a first hairpin adapter is ligated to one end of the product fragment and a second hairpin adapter is ligated to the other end of the product fragment, where the first hairpin adapter has a single-stranded overhang that is complementary to a single-stranded overhang on one end of the product fragment, and the second hairpin adapter has a single-stranded overhang that is complementary to a single-stranded overhang on the other end of the product fragment.

The steps can be repeated to achieve a greater degree of amplification. Thus, in one class of embodiments, the first circular progeny nucleic acid comprises a second primer binding sequence, a recognition site for a third restriction endonuclease, and a recognition site for a fourth restriction endonuclease, which recognition sites flank the target region. The first and second primer binding sequences can be the same or different. The recognition sites for the third and fourth restriction endonucleases (and the third and fourth restriction endonucleases themselves) can be the same or different. The same, one of the same, or different enzyme(s) can be used in the second round as in the first round.

A second primer is bound to the second primer binding sequence, and polymerase-mediated template-directed primer extension of the second primer is performed with a polymerase comprising strand displacement activity, thereby producing a second nucleic acid product comprising at least two copies of the first polynucleotide sequence and the second polynucleotide sequence, at least one copy of each of which is not base paired to the first circular progeny nucleic acid. The second product is digested with the third and fourth endonucleases, and at least one second product fragment having a double-stranded region that comprises the target region is released. Optionally, a third hairpin adapter is ligated to one end of the second product fragment and a fourth hairpin adapter is ligated to the other end of the second product fragment, thereby producing at least one second circular progeny nucleic acid.

In one class of embodiments, the first or second hairpin adapter comprises the second primer binding sequence. In other embodiments, the second primer binding sequence is formed by ligation of the first or second hairpin adapter to the first product fragment.

The various steps (primer binding, primer extension, digestion with the restriction enzymes, ligation, etc.) can be performed sequentially or concurrently. For example, restriction digestion can be performed after primer extension is complete, or it can be performed concurrently with the primer extension reaction. Similarly, ligation of adapter(s) to the product fragment can be performed after digestion is complete, or digestion and ligation can be performed concurrently. As another example, primer extension, digestion, and ligation can be performed concurrently. Optionally, when multiple rounds of amplification are performed, the primer extension, digesting, and ligating steps to produce the first circular progeny nucleic acid and the primer extension and digesting steps to produce the second product fragment are performed in a single reaction mixture. A ligating step to produce a second circular progeny nucleic acid can also be performed in the same reaction mixture. In embodiments in which digestion is performed concurrently with primer extension and/or ligation, the nucleic acid template and/or the first circular progeny nucleic acid are optionally not subject to being cleaved by the first and second restriction endonucleases.

In embodiments in which introduction of random mutations is desirable, in one or more rounds of amplification, primer extension is performed under mutagenic conditions. For example, primer extension can be performed in the presence of a low fidelity strand-displacing polymerase, unequal concentrations of nucleotides, at least one mutagenic nucleotide analog, and/or $Mn^{2+}$.

Essentially all of the features noted for the methods above apply to these embodiments as well, as relevant, for example, with respect to the polymerase employed, type of target region, subsequent manipulation (e.g., sequencing) of the amplified target region, and/or the like. For example, in one class of embodiments, the cleavage site for the first and/or second restriction endonuclease (and/or for the third and/or fourth restriction endonuclease) is within the target region.

Yet another general class of embodiments provides methods of amplifying a nucleic acid target region. In the methods, a nucleic acid template is provided. The template is a circular nucleic acid having a double-stranded central region that comprises a first polynucleotide sequence and a second polynucleotide sequence complementary to the first polynucleotide sequence. The first and second polynucleotide sequences collectively comprise the target region and at least one recognition site for at least one first site-specific endonuclease. The circular nucleic acid also includes two single-stranded hairpin end regions and comprises a first primer binding sequence.

A first primer is bound to the first primer binding sequence, and polymerase-mediated template-directed primer extension of the first primer is performed with a polymerase comprising strand displacement activity, thereby producing a first nucleic acid product that comprises at least two copies of the first polynucleotide sequence and the second polynucleotide sequence, at least one copy of each of which is not base paired to the template. Typically, a copy of the first polynucleotide sequence that is not base paired to the template is base paired to a copy of the second polynucleotide sequence. Typically, the first nucleic acid product comprises at least two copies of the complement of the template, at least one copy of which is not base paired to the template. The first nucleic acid product typically contains more than two copies of the first polynucleotide sequence and the second polynucleotide sequence, for example, at least three copies (at least two copies of each of which are not base paired to the template), at least five copies, at least 10 copies, at least 20 copies, at least 30 copies, at least 40 copies, or at least 50 copies.

The first product is cut with the at least one first endonuclease, and at least one first progeny nucleic acid having a double-stranded region that comprises the target region is released. The at least one first endonuclease can be, e.g., a restriction endonuclease, a nicking endonuclease, two restriction endonucleases, two nicking endonucleases, or a restriction endonuclease and a nicking endonuclease. The template can include, e.g., a single endonuclease recognition site or two sites flanking the target region. The first progeny nucleic acid can be, e.g., a product hairpin or a product fragment, with ends depending on the particular endonuclease(s) employed.

The progeny nucleic acid can be used in essentially any desired application. For example, the at least one first progeny nucleic acid can be circularized, thereby producing at least one first circular progeny nucleic acid comprising the target region. The first circular progeny nucleic acid can include a second primer binding sequence, e.g., for determining the sequence of the target region or for performing a second round of amplification. In embodiments in which a second round of amplification is performed, the first circular progeny nucleic acid comprises a second primer binding sequence and a recognition site for at least one second site-specific endonuclease. A second primer is bound to the second primer binding sequence, and polymerase-mediated template-directed primer extension of the second primer is performed with a polymerase comprising strand displacement activity, thereby producing a second nucleic acid product comprising at least two copies of the first polynucleotide sequence and the second polynucleotide sequence, at least one copy of each of which is not base paired to the first circular progeny nucleic acid. The second product is cut with the at least one second endonuclease, and at least one second progeny nucleic acid having a double-stranded region that comprises the target region is released. The at least one second progeny nucleic acid can be circularized if desired, thereby producing at least one second circular progeny nucleic acid.

The at least one second endonuclease can be, e.g., a restriction endonuclease, a nicking endonuclease, two restriction endonucleases, two nicking endonucleases, or a restriction endonuclease and a nicking endonuclease. The particular second endonuclease(s) used and the number of second endonucleases can be selected independently from the first endonuclease(s) and the number of first endonucleases used. The first circular progeny nucleic acid can include, e.g., a single endonuclease recognition site or two sites flanking the target region. The second progeny nucleic acid can be, e.g., a product hairpin or a product fragment, with ends depending on the particular endonuclease(s) employed in the second round and independently of the type of first progeny nucleic acid produced.

In embodiments in which introduction of random mutations is desirable, in one or more rounds of amplification, primer extension is performed under mutagenic conditions. For example, primer extension can be performed in the presence of a low fidelity strand-displacing polymerase, unequal concentrations of nucleotides, at least one mutagenic nucleotide analog, and/or $Mn^{2+}$.

Essentially all of the features noted for the methods above apply to these embodiments as well, as relevant, for example, with respect to the polymerase employed, type of target region, configuration of the template, primer, product, and/or progeny nucleic acid, subsequent manipulation (e.g., sequencing) of the amplified target region, and/or the like.

Compositions, kits, and systems related to, produced by, or of use in the methods are another feature of the invention. For example, one general class of embodiments provides a composition that includes a nucleic acid template that comprises a first primer binding sequence, a first primer that is complementary to the first primer binding sequence, and a polymerase, preferably a polymerase that has strand displacement activity. The template is a circular nucleic acid having a double-stranded central region and two single-stranded hairpin end regions. The double-stranded central region of the template comprises a first polynucleotide sequence and a second polynucleotide sequence complementary to the first polynucleotide sequence. These first and second polynucleotide sequences collectively comprise a target region, and generally also comprise a recognition site for a first site-specific endonuclease. The composition optionally includes the first endonuclease. The composition can also include a first nucleic acid product comprising at least two copies of the first polynucleotide sequence and the second polynucleotide sequence, at least one copy of each of which is not base paired to the template, and/or a first product hairpin having at least one single-stranded hairpin end region, a double-stranded region that comprises the target region, a free 5' terminus, and a free 3' terminus. The composition optionally includes a ligase.

In one class of embodiments, the first endonuclease is a restriction endonuclease. In this class of embodiments, the composition can also include a first hairpin adapter suitable for ligation to the product hairpin. For example, the first product hairpin can include a single-stranded overhang on the end opposite to the single-stranded hairpin end region, and the first hairpin adapter can have a single-stranded overhang that is complementary to the single-stranded overhang on the first product hairpin. Optionally, the nucleic acid template is not subject to cleavage by the first restriction endonuclease; for example, the nucleic acid template can be suitably methylated or include a nonstandard nucleotide or backbone linkage. Similarly, the hairpin adapter can be methylated or otherwise modified, whereby the product of ligating the hairpin adapter to the first product hairpin is not subject to cleavage by the first restriction endonuclease.

The composition can include a first circular progeny nucleic acid that is the product of ligating the hairpin adapter to the first product hairpin. Optionally, the first circular progeny nucleic acid comprises a second primer binding sequence, and can also include a recognition site for a second restriction endonuclease. The second primer binding sequence can be identical to or different from the first primer binding sequence. In one class of embodiments, the first hairpin adapter comprises the second primer binding sequence. In one class of embodiments, the second primer binding sequence comprises the recognition site for the first restriction endonuclease. The recognition site for the second restriction endonuclease can be identical to the recognition site for the first restriction endonuclease and the first and second restriction endonucleases can be the same enzyme, or the first and second restriction endonucleases can be different enzymes having different recognition sites. The composition can also include a second nucleic acid product comprising at least two copies of the first polynucleotide sequence and the second polynucleotide sequence, at least one copy of each of which is not base paired to the first circular progeny nucleic acid, and/or a second product hairpin.

In one class of embodiments, the first endonuclease is a nicking endonuclease. The composition can include a first circular progeny nucleic acid that is the product of intramolecularly ligating the 5' and 3' termini of the first product hairpin to each other. Optionally, the first circular progeny nucleic acid comprises a second primer binding sequence.

The second primer binding sequence can be the same as, or more typically, different from the first primer binding sequence. The first circular progeny nucleic acid optionally includes a recognition site for a second nicking endonuclease. The recognition site for the second nicking endonuclease can be identical to the recognition site for the first nicking endonuclease and the first and second nicking endonucleases can be the same enzyme, or the first and second nicking endonucleases can be different enzymes having different recognition sites. In one class of embodiments, the second primer binding sequence comprises the recognition site for the first nicking endonuclease. The composition can also include a second nucleic acid product comprising at least two copies of the first polynucleotide sequence and the second polynucleotide sequence, at least one copy of each of which is not base paired to the first circular progeny nucleic acid, and/or a second product hairpin.

Essentially all of the features noted for the methods above apply to the compositions as well, as relevant; for example, with respect to the configuration of the nucleic acid template, type of target region, type of polymerase, inclusion of at least one mutagenic nucleotide analog and/or $Mn^{2+}$, and the like.

One general class of embodiments provides a composition that includes a nucleic acid template. The template is a circular nucleic acid having a double-stranded central region and two single-stranded hairpin end regions. The double-stranded central region comprises a first polynucleotide sequence and a second polynucleotide sequence complementary to the first polynucleotide sequence, which first and second polynucleotide sequences collectively comprise a target region, a recognition site for a first restriction endonuclease, and a recognition site for a second restriction endonuclease, which recognition sites flank the target region. The circular nucleic acid template also comprises a first primer binding sequence.

The composition also includes a first primer that is complementary to the first primer binding sequence, a polymerase comprising strand displacement activity, and a first nucleic acid product comprising at least two copies of the first polynucleotide sequence and the second polynucleotide sequence, at least one copy of each of which is not base paired to the template. The composition can also include the first endonuclease, the second endonuclease, and a first product fragment having a double-stranded region that comprises the target region. The composition optionally includes a ligase.

In one class of embodiments, the recognition site for the second restriction endonuclease has the same sequence as the recognition site for the first restriction endonuclease, and the first and second restriction endonucleases are the same enzyme. In another class of embodiments, the recognition site for the second restriction endonuclease is different from the recognition site for the first restriction endonuclease, and the first and second restriction endonucleases are different enzymes.

The composition can also include one or more hairpin adapters suitable for ligating to the first product fragment. For example, the composition can include a first hairpin adapter having a single-stranded overhang that is complementary to a single-stranded overhang on one end of the product fragment and a second hairpin adapter having a single-stranded overhang that is complementary to a single-stranded overhang on the other end of the product fragment. Optionally, the nucleic acid template is not subject to cleavage by the first and second restriction endonucleases; for example, the nucleic acid template can be suitably methylated or include a nonstandard nucleotide or backbone linkage. Similarly, the first and second hairpin adapters can be methylated or otherwise modified, whereby the product of ligating the hairpin adapters to the first product fragment is not subject to cleavage by the first and second restriction endonucleases.

The composition can include a first circular progeny nucleic acid that is the product of ligating the first and second hairpin adapters to the first product fragment. Optionally, the first circular progeny nucleic acid comprises a second primer binding sequence, and can also include a recognition site for a third restriction endonuclease and a recognition site for a fourth restriction endonuclease, which sites flank the target region. The second primer binding sequence can be identical to or different from the first primer binding sequence. In one class of embodiments, the first or second hairpin adapter comprises the second primer binding sequence. In one class of embodiments, the second primer binding sequence comprises the recognition site for the first or second restriction endonuclease.

In one class of embodiments, the recognition site for the third restriction endonuclease has the same sequence as the recognition site for the fourth restriction endonuclease, and the third and fourth restriction endonucleases are the same enzyme. In another class of embodiments, the recognition site for the third restriction endonuclease is different from the recognition site for the fourth restriction endonuclease, and the third and fourth restriction endonucleases are different enzymes. The third and fourth enzymes and sites can be the same as the first and second enzymes and sites, different than the first and second enzymes and sites, or a combination thereof.

The composition can also include a second nucleic acid product comprising at least two copies of the first polynucleotide sequence and the second polynucleotide sequence, at least one copy of each of which is not base paired to the first circular progeny nucleic acid. The composition can also include the second primer, third and fourth restriction enzymes, a second product fragment, third and fourth hairpin adapters, a second circular progeny nucleic acid, and the like.

Essentially all of the features noted for the methods above apply to the compositions as well, as relevant; for example, with respect to the configuration of the nucleic acid template, type of target region, type of polymerase, inclusion of at least one mutagenic nucleotide analog and/or $Mn^{2+}$, and the like.

Figure 1:
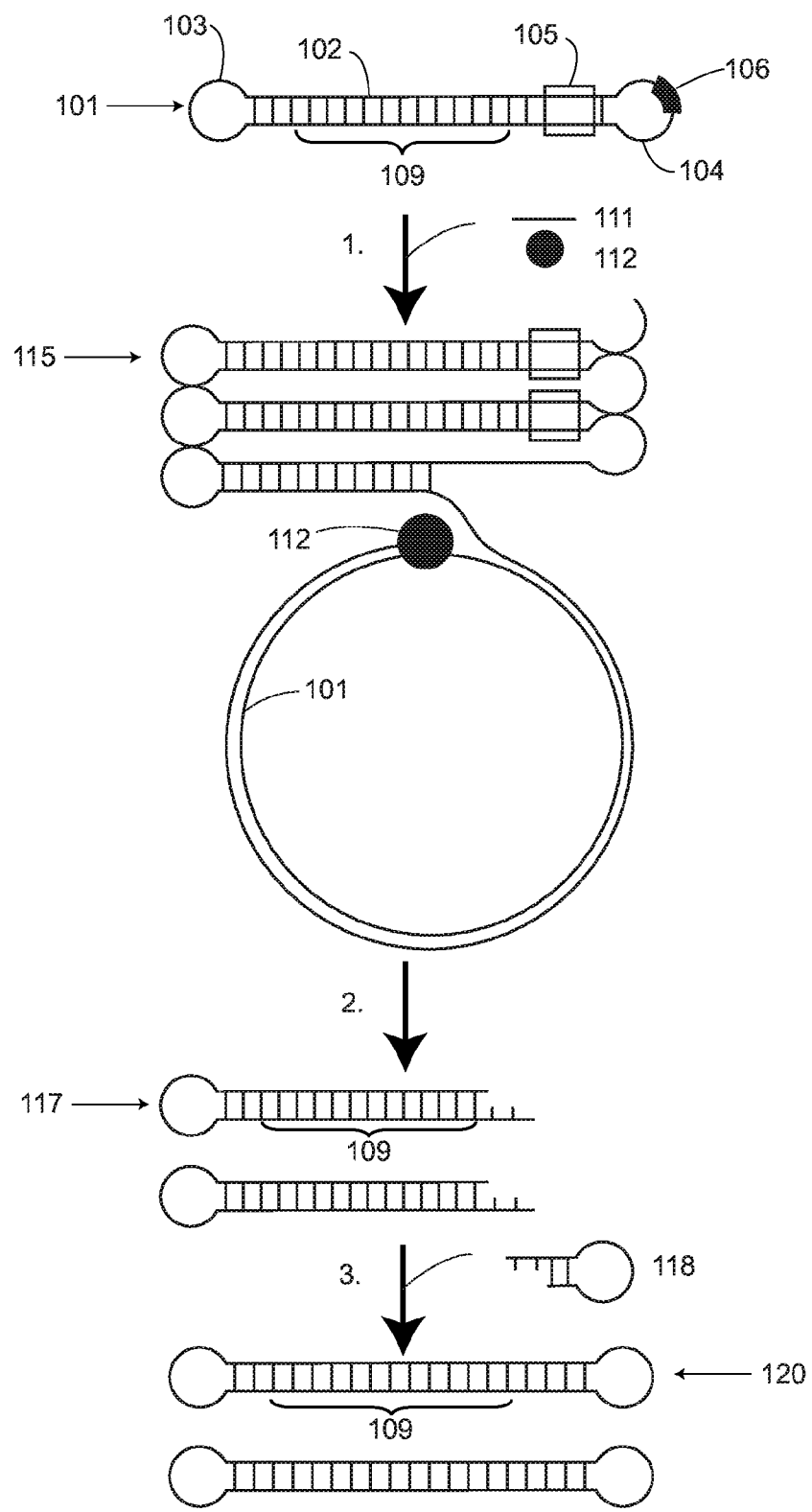
FIG. 1 schematically illustrates an exemplary amplification process in which a restriction site is proximal to the primer binding site.

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins, reference to "a cell" includes mixtures of cells, and the like.

The terms "nucleic acid," "polynucleotide," and "oligonucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides, and/or alternate backbones, e.g., including non-phosphodiester bonds), and the like. A nucleic acid can be e.g., single-stranded or double-stranded. Unless otherwise indicated, a particular nucleic acid sequence of this invention encompasses complementary sequences, in addition to the sequence explicitly indicated.

A "site-specific endonuclease" is an enzyme (e.g., a restriction endonuclease or a nicking endonuclease) that cuts at least one strand of a double-stranded nucleic acid (typically double-stranded DNA) after recognizing a specific site on the nucleic acid.

A "restriction endonuclease" or "restriction enzyme" is an enzyme that cuts a double-stranded nucleic acid (typically double-stranded DNA) after recognizing a specific site on the nucleic acid. Typically, the restriction enzyme cuts both strands of the nucleic acid. Certain restriction enzymes cut the substrate at their recognition site, while for other restriction enzymes the recognition and cleavage sites are different. Restriction endonucleases include, e.g., naturally occurring restriction enzymes, recombinant restriction enzymes, and artificial restriction enzymes (e.g., zinc finger nucleases or TAL effector nucleases). "Digestion" of a double-stranded nucleic acid with a restriction endonuclease involves cutting both strands of the nucleic acid at the enzyme's cleavage site on the nucleic acid.

A "nicking endonuclease" is an enzyme that cuts one strand of a double-stranded nucleic acid (typically double-stranded DNA) after recognizing a specific site on the nucleic acid. Certain nicking endonucleases nick the substrate at their recognition site, while for other nicking endonucleases the recognition and nicking sites are different. Nicking endonucleases include, e.g., naturally occurring nicking endonucleases, recombinant nicking endonucleases, and artificial nicking endonucleases. "Nicking" of a double-stranded nucleic acid with a nicking endonuclease involves cutting only one strand of the nucleic acid at the enzyme's cleavage site on the nucleic acid.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ29 DNA polymerase (e.g., as listed in SEQ ID NO:1); examples include the B103, GA-1, PZA, Φ15, BS32, M2Y (also known as M2), Nf, G1, Cp-1, PRD1, PZE, SF5, Cp-5, Cp-7, PR4, PR5, PR722, L17, and AV-1 DNA polymerases, as well as chimeras thereof. A modified recombinant Φ29-type DNA polymerase includes one or more mutations relative to naturally-occurring wild-type Φ29-type DNA polymerases, for example, one or more mutations that increase stability, increase readlength, alter interaction with and/or incorporation of nucleotide analogs, enhance accuracy, and/or alter another polymerase property, and may include additional alterations or modifications over the wild-type Φ29-type DNA polymerase, such as one or more deletions, insertions, and/or fusions of additional peptide or protein sequences (e.g., for immobilizing the polymerase on a surface or otherwise tagging the polymerase enzyme).

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences. For example, residue K221 of wild-type M2Y polymerase (SEQ ID NO:2) is identified as position Y224 relative to wild-type Φ29 polymerase (SEQ ID NO:1); see, e.g., the alignment shown in FIG. 43 of US patent application publication 2012/0034602 Similarly, residue L138 of wild-type M2Y polymerase (SEQ ID NO:2) is identified as position V141 relative to wild-type Φ29 polymerase (SEQ ID NO:1), and an L138K substitution in the M2Y polymerase is thus identified as a V141K substitution relative to SEQ ID NO:1. When referring to Φ29-type DNA polymerases, amino acid positions herein are generally identified relative to SEQ ID NO:1 unless explicitly indicated otherwise.

A "nucleotide analog" is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into an oligonucleotide, the resulting residue in the oligonucleotide can be the same as, or different from, an A, G, C, T, or U residue (that is, any non-standard moiety of the analog can be incorporated into the oligonucleotide, or it can be cleaved off during incorporation of the analog into the oligonucleotide).

Where a range of values is provided, it is understood that each intervening value between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

A variety of additional terms are defined or otherwise characterized herein.

DETAILED DESCRIPTION

Accurate determination of copy number of repeated sequences is of interest in a variety of fields. For example, in forensics, differences in copy number at various short tandem repeat loci are used for human identification. In medicine, copy number of microsatellite repeats is implicated in numerous diseases. For example, trinucleotide repeat disorders such as Huntington's disease and fragile X syndrome are caused by expansion of trinucleotide repeats in certain genes past a normal threshold.

A variety of techniques for determining copy number of such sequences have been described in the art. However, such techniques typically involve an initial amplification step to provide enough of the region of interest containing the repeats for the copy number to be detected and/or to reduce the complexity of the sample by increasing the prevalence of the region of interest. Although PCR is an effective means of amplifying many sequences, problems such as trans reannealing and polymerase stutter can introduce artifacts when the target region includes repeat sequences, complicating or confounding attempts to accurately determine how many repeats were initially present.

Strand displacement synthesis, in contrast, is a high fidelity mode of replication that tends to preserve the repeat count of homonucleotides, dinucleotides, trinucleotides, tetranucleotides, pentanucleotides, and other repeat sequences. Amplification with a strand-displacing polymerase is thus an effective means of amplifying a desired region of a nucleic acid of interest (a "target region"), whether the region includes repeated sequence elements or not. Methods for amplifying essentially any desired nucleic acid through target-directed rolling circle amplification with a strand-displacing polymerase are detailed hereinbelow.

Targeted Rolling Circle Amplification

In one aspect, the invention provides methods for amplifying a nucleic acid target region. A suitable nucleic acid template that includes the target region can be produced using techniques known in the art. Preferred nucleic acid templates include circular nucleic acids, particularly a circular nucleic acid having a double-stranded central region and two single-stranded hairpin end regions (that is, loops connecting the two complementary strands of the double-stranded region). The double-stranded central region typically comprises the target region. As will be appreciated, the term circular, when referring to the strand configuration, merely denotes a strand of a nucleic acid that includes no terminal nucleotides, and does not necessarily denote any geometric configuration.

Production of such circular nucleic acids is detailed, e.g., in U.S. Pat. No. 8,153,375 "Compositions and Methods for Nucleic Acid Sequencing" and in Travers et al. (2010) Nucl. Acids Res. 38(15):e159, each of which is incorporated herein by reference in its entirety for all purposes. For example, double-stranded DNA fragments can be ligated to stem-loop adapters. Each fragment can be ligated to two different adapters, such that the resulting hairpin end regions are different, or each fragment can be ligated to two adapters of the same type, such that the resulting hairpin end regions are the same. Where the double-stranded fragments are produced from a complex nucleic acid sample (e.g., genomic DNA, a mixture of cDNAs, etc.) including both target and non-target fragments, some members of the resulting population of circular nucleic acids may include non-target sequences. Optionally, the mixture is enriched for those nucleic acids containing the desired target sequence, such that a higher percentage of the resulting nucleic acids contain the desired target region, e.g., as described in U.S. patent application 61/789,354 "Compositions and Methods for Selection of Nucleic Acids" by Pham et al. filed Mar. 15, 2013, U.S. patent application Ser. No. 13/427,725 "Isolation of Polymerase-Nucleic Acid Complexes," U.S. patent application 61/721,339 "Compositions and Methods for Selection of Nucleic Acids," and/or U.S. patent application Ser. No. 14/069,067 "Compositions and Methods for Selection of Nucleic Acids," each of which is incorporated herein by reference in its entirety for all purposes.

The target region can be derived from essentially any desired source, e.g., a whole genome, a collection of chromosomes, a single chromosome, or one or more regions from one or more chromosomes. It can be derived from cloned DNA (e.g., BACs, YACs, PACs, etc.), RNA (e.g., mRNA, tRNA, rRNA, ribozymes, etc.), cDNA, or a combination thereof. The sample from which the target is derived can be a metagenomic sample, e.g., an environmental or intestinal sample. Nucleic acids can be collected from various sources including, but not limited to, whole blood, semen, saliva, tears, urine, fecal material, sweat, buccal cells, skin, and hair. The nucleic acids can be obtained from the same individual, which can be a human or other species (e.g., plant, bacteria, fungi, algae, archaea, etc.), or from different individuals of the same species, or different individuals of different species. Methods for generating a nucleic acid sample, e.g., from one of the sources listed above, is known and routine to those of ordinary skill in the art. Typically it involves cell lysis, stabilization and protection of the nucleic acids (e.g., from nuclease digestion), isolation of the nucleic acids from other components (e.g., proteins, carbohydrates, lipids, etc.) of the original sample, and optional fragmentation, e.g., by chemical, enzymatic, or mechanical means. A variety of commercial kits for purification of nucleic acids are available.

As noted above, strand displacement synthesis can accurately copy even target regions containing repeat sequences. Thus, in one aspect, the target region comprises at least five tandem copies of a mononucleotide (i.e., homonucleotide), dinucleotide, trinucleotide, tetranucleotide, or pentanucleotide repeat sequence, e.g., at least 10, at least 20, at least 30, at least 40, at least 50, at least 60, at least 70, at least 80, at least 90, at least 100, at least 150, at least 200, or at least 250 copies of the repeat sequence. Exemplary repeat sequences of interest include, but are not limited to, polyA tracts (AAAA . . . ), TC, AT, and GT dinucleotide repeats (TCTC . . . , ATAT . . . , and GTGT . . . ), CGG, CAG, and CTG trinucleotide repeats (CGGCGG . . . , CAGCAG . . . , and CTGCTG . . . ), TTTA and GAAA tetranucleotide repeats (TTTATTTA . . . and GAAAGAAA . . . ), and ATTCT and TTTTA pentanucleotide repeats. Strand displacement synthesis can also be useful for other types of target regions that are difficult to amplify by PCR. Thus, for example, the target region can comprise a palindrome and/or a region having a high GC content.

The template nucleic acid includes a primer binding sequence. The primer binding site is optionally located in one of the two single-stranded hairpin end regions. Alternatively, both of the hairpin end regions can include the primer binding sequence (e.g., in embodiments in which the two hairpin end regions have the same sequence), or a primer binding site can be located either partially in an end region and extending into the double-stranded region or entirely in the double-stranded region. The primer binding sequence can be provided by one (or both) of the stem-loop adapters initially used to produce the template, found within the target region or in sequences adjacent to the target region and originating from the same source (e.g., flanking the target region in a double-stranded genomic fragment or other fragment used to produce the template), or created by the union of the target region (or its flanking sequence) and one of the adapters initially used to produce the template.

A primer is provided, from which a nascent nucleic acid strand will be produced that is complementary to the template strand. The primer is usually a short oligonucleotide all or part of which is complementary to a portion of the template nucleic acid (i.e., complementary to the primer binding sequence). Selection of suitable primer binding sequences and production of primers is well known in the art. Primers useful in the methods of the invention can comprise naturally occurring DNA or RNA oligonucleotides. The primers of the invention can also be synthetic analogs. The primers may have alternative backbones and/or have other modifications, such as inclusion of heteroatoms, attachment of labels such as dyes, or substitution with functional groups which will still allow for base pairing and for recognition by the enzyme. Primers can be selected to recognize tighter binding primer sequences, e.g., GC-rich sequences, and can include within their structure non-natural nucleotides or nucleotide analogs, e.g., peptide nucleic acids (PNAs) or locked nucleic acids (LNAs) that can demonstrate higher affinity pairing with the template. Primers can contain degenerate positions (positions at which more than one base will be found in different instances of the oligonucleotide), as well as regions that are not complementary to the template DNA, so long as those non-complementary regions do not prevent the initiation of synthesis.

The primer is bound to the primer binding sequence. As noted, the primer binding sequence is optionally located in one of the single-stranded hairpin end regions of the circular nucleic acid template. In such embodiments, the double-stranded portion of the template need not be denatured to permit binding of the primer to the template. In embodiments in which the primer binding sequence is partially or completely within the double-stranded region, the target can be denatured, if necessary, to permit binding of the primer, or a primer comprising modified bases that enhance hybridization (e.g. PNA (peptide nucleic acid) nucleotides, LNA (locked nucleic acid) nucleotides, O-methyl-modified nucleotides, and other modified nucleotides known in the art that have a greater affinity to a complementary base than does a canonical nucleotide) can be employed to allow the primer to bind to the double-stranded sequence even without prior denaturation, e.g., by strand invasion. Similarly, known recombination enzymes can also be present to facilitate strand invasion, e.g., E. coli RecA and RecT proteins, yeast Rad 51 and Rad52 proteins, human splicing factor PSF, protein β from phage lambda, and other enzymes including helicases and single-stranded DNA binding proteins.

The primer is extended in the presence of a polymerase, preferably a strand-displacing polymerase, that incorporates nucleotides and/or nucleotide analogs to produce a product strand that is complementary to the template strand. Suitable polymerases are described hereinbelow. As synthesis progresses, the polymerase's activity displaces one complementary strand of the template's double-stranded region from the other strand, and synthesis of the nascent product strand continues. Upon completion of one full cycle around the template, a double-stranded sequence containing the original circular template strand and the newly synthesized strand results. The polymerase can continue extension, now displacing one end of the nascent strand as it extends the other end. The polymerase can continue around the template multiple times, producing a long product that is a concatamer of copies of the complement of the template strand, the most recent of which is base-pared to the template.

The product typically contains at least two copies of the complement of the template (and thus at least two copies of each strand of the double-stranded central region), e.g., at least three copies, at least five copies, at least 10 copies, at least 20 copies, at least 30 copies, at least 40 copies, or at least 50 copies. It will be evident that the number of copies is related to the read length and inversely correlated with the length of the target region and the total size of the template.

Self-complementary portions of the nascent product strand typically hybridize to each other as they are displaced by the polymerase, producing a long chain of concatenated hairpin structures. This concatenated product can be resolved in various ways. For example, the concatenated product can be resolved to produce individual product hairpins, each containing a copy of the target region, by treatment with a site-specific endonuclease, e.g., a restriction endonuclease or a nicking endonuclease. The product hairpins can then be circularized, as described in greater detail below. As another example, the concatenated product can be resolved to produce individual product fragments, each containing a copy of the target region, by treatment with a pair of site-specific endonucleases, e.g., a pair of restriction endonucleases, a pair of nicking endonucleases, or a restriction endonuclease and a nicking endonuclease, whose cut sites flank the target region or with a single site-specific endonuclease with cut sites flanking the target region. The product fragments can then be circularized, as described in greater detail below. As yet another example, the concatenated product can be resolved by treatment with a site-specific recombinase, as described in greater detail below.

In embodiments in which the template includes two primer binding sequences (e.g., one in each of two identical hairpin end regions), it will be evident that two primers can bind to the template and two polymerase molecules can proceed around the template, each displacing the other's nascent product strand, to produce two long concatameric products from the template. Each of these concatameric products can be treated as detailed below.

Release of Product Hairpins with Restriction Endonucleases

In one class of embodiments, the double-stranded portion of the template nucleic acid includes a restriction endonuclease recognition site. The double-stranded portions of the concatenated hairpins formed by the displaced product strand thus also contain the restriction site, and digestion of the product with the restriction enzyme thus releases at least one product hairpin. Typically, the digestion releases two or more product hairpins, up to the number of complete copies of the complement that were displaced by the polymerase, subject to placement of the restriction site as described below. Again subject to placement of the restriction site, the digestion can either immediately release the product hairpins, or denaturation to separate one strand of the stem of one hairpin from the other strand of the stem of an adjacent hairpin followed by annealing step in which the self complementary portions of individual molecules hybridize can release the product hairpins.

The product hairpins released after the restriction digestion generally include a double-stranded region that comprises the target region, and also include free 5' and 3' termini (typically, a free 5' phosphate group and a free 3' hydroxyl group). The product hairpins can be blunt ended or can have a 5' or 3' single-stranded overhang, depending on the cleavage pattern of the particular restriction enzyme employed.

The product hairpins can be employed in essentially any desired application, e.g., sequence determination, copy number determination, subsequent molecular cloning steps, mutagenesis, or the like. In one exemplary class of embodiments, a hairpin adapter is ligated to the free termini of each of the product hairpins to produce a circular progeny nucleic acid. Similar to the circular nucleic acid template, the circular progeny nucleic acid has a double-stranded central region comprising the target region and has two single-stranded hairpin end regions. The loop of one end region is complementary to that of one of the template's, and the other is derived from the hairpin adapter. The circular progeny nucleic acid optionally also includes one or more primer binding site and/or restriction site.

The hairpin adapter includes two complementary nucleic acid segments separated by a stretch of non-complementary nucleotides. The resulting structure includes a double-stranded stem formed by the complementary segments and a single-stranded loop. The stem can be blunt ended, or it can include a 5' single-stranded overhang or a 3' single-stranded overhang. It will be evident that where the adapter is to ligate to a blunt ended nucleic acid (e.g., a product hairpin produced by digestion with a restriction endonuclease that leaves blunt ends, or a product produced by digestion with a restriction endonuclease that leaves a single-stranded overhang followed by polishing with a polymerase to fill in a 5' overhang or remove a 3' overhang), the adapter is preferably blunt ended. Where the adapter is to ligate to a nucleic acid having an overhang, the adapter preferably has a complementary overhang. Accordingly, in one class of embodiments, the hairpin adapter has a single-stranded overhang that is complementary to a single-stranded overhang on the product hairpin. Suitable hairpins are readily designed and synthesized using conventional nucleic acid synthesis techniques. The adapter can be present during the restriction digestion or it can be added subsequently to the reaction mixture. The adapter is typically provided in excess, e.g., to speed the reaction and to discourage re-ligation between the product hairpin and the loop region removed from it by the restriction enzyme. Although hairpin adapters provide a convenient technique for circularizing the product hairpin, any of the other linking oligonucleotides or techniques described in U.S. Pat. No. 8,153,375 can be employed instead or in addition. Anti-ligators (alligators) are optionally employed to reduce or prevent off-target ligation events, as described in U.S. patent application Ser. No. 14/069,067.

As noted above, placement of the restriction site affects how the product hairpins are released. In one class of embodiments, the recognition site for the restriction enzyme is proximal to the primer binding sequence (that is, the recognition site is at the same end of the double-stranded target region as is the primer binding sequence). Preferred restriction enzymes include those having a cleavage site either near or within the recognition site; the cleavage site for the restriction endonuclease is thus also proximal to the primer binding sequence.

The amplification process for a template in which the restriction site is proximal to the primer binding site is schematically illustrated in FIG. 1. As shown, nucleic acid template 101 is a circular nucleic acid having double-stranded central region 102 and single-stranded end regions 103 and 104. Double-stranded region 102 includes target region 109. Single-stranded end region 104 includes primer binding sequence 106. Recognition site 105 for a restriction enzyme is located between target region 109 and primer binding sequence 106. The cleavage site for the restriction enzyme is most conveniently within or near the recognition site, as illustrated.

As illustrated in step 1, template 101 is complexed with primer 111, which binds to primer binding sequence 106, and strand-displacing polymerase 112 in the presence of the four standard nucleotides and/or analogs thereof. Polymerase 112 extends the primer. As synthesis continues, the polymerase displaces one complementary strand of double-stranded region 102 from the other. Upon completing one full cycle around the template, a double-stranded sequence including original template 101 and the newly synthesized strand results. Synthesis continues around template 101 multiple times as polymerase 112 continues to displace the newly synthesized nascent strand, producing product 115 containing multiple copies of the complement of the template. Self-complementary portions of nascent product strand 115 hybridize to each other as they are displaced by the polymerase, producing long concatenated hairpin structures. Since they are copies of template 101, the double-stranded portions of the concatenated hairpins formed by the displaced product strand also contain restriction site 105. Digestion of product 115 with the restriction enzyme thus releases at least one product hairpin 117 as shown in step 2. Typically, digestion releases a number of product hairpins equal to the number of complete copies of the complement that were displaced by the polymerase.

Hairpin adapter 118 having a single-stranded overhang complementary to a single-stranded overhang on product hairpin 117 is provided and ligated to the product hairpins in step 3, producing circular progeny nucleic acid 120. (It will be evident that where the product hairpin has or is modified to have blunt ends, a blunt ended hairpin adapter is provided.)

In another class of embodiments, the recognition site for the restriction enzyme is distal to the primer binding sequence (that is, the recognition site is at the opposite end of the double-stranded target region from the primer binding sequence). Preferred restriction enzymes include those having a cleavage site either within or near the recognition site; the cleavage site for the restriction endonuclease is thus also distal to the primer binding sequence.

Figure 2:
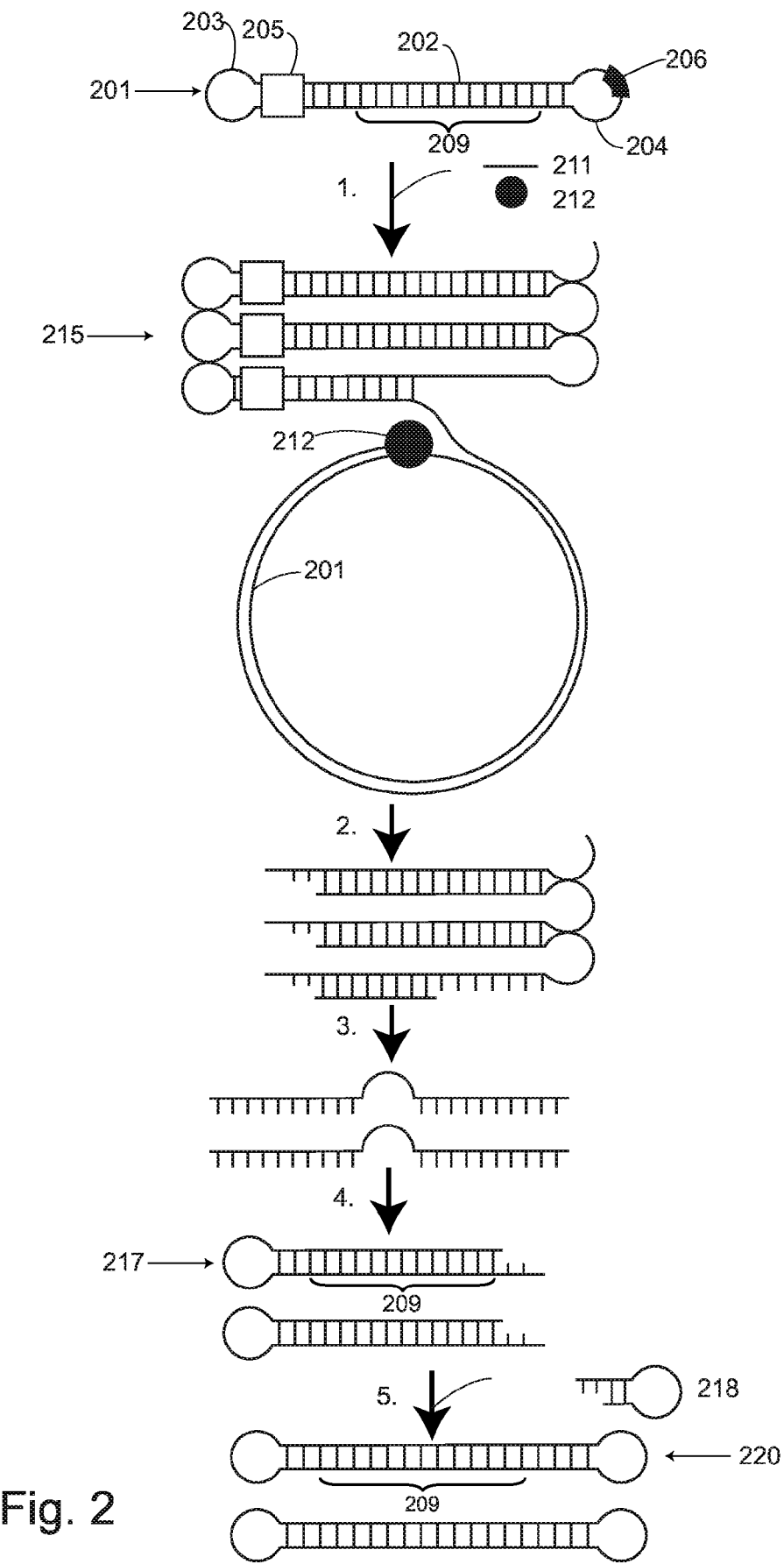
FIG. 2 schematically illustrates an exemplary amplification process in which a restriction site is distal to the primer binding site.

The amplification process for a template in which the restriction site is distal to the primer binding site is schematically illustrated in FIG. 2. As shown, nucleic acid template 201 is a circular nucleic acid having double-stranded central region 202 and single-stranded end regions 203 and 204. Double-stranded region 202 includes target region 209. Single-stranded end region 204 includes primer binding sequence 206. Recognition site 205 for a restriction enzyme is located at the opposite end of target region 209 from primer binding sequence 206. The cleavage site for the restriction enzyme is most conveniently within or near the recognition site, as illustrated.

As illustrated in step 1, template 201 is complexed with primer 211, which binds to primer binding sequence 206, and strand-displacing polymerase 212 in the presence of the four standard nucleotides and/or analogs thereof. Polymerase 212 extends the primer. As synthesis continues, the polymerase displaces one complementary strand of double-stranded region 202 from the other. Upon completing one full cycle around the template, a double-stranded sequence including original template 201 and the newly synthesized strand results. Synthesis continues around template 201 multiple times as polymerase 212 continues to displace the newly synthesized nascent strand, producing product 215 containing multiple copies of the complement of the template. Self-complementary portions of nascent product strand 215 hybridize to each other as they are displaced by the polymerase, producing long concatenated hairpin structures. Since they are copies of template 201, the double-stranded portions of the concatenated hairpins formed by the displaced product strand also contain restriction site 205.

As shown in step 2, digestion of product 215 with the restriction enzyme results in a daisy chain in which one strand of the stem of one molecule is hybridized to the other strand of the stem of an adjacent molecule. In step 3, the cleavage products are denatured, e.g., by increasing the temperature of the reaction mixture. As shown in step 4, annealing (e.g., by decreasing the temperature the reaction mixture) results in hybridization of the self-complementary portions of individual molecules to produce product hairpins 217. Typically, digestion followed by melting and annealing releases a number of product hairpins that is one less than the number of complete copies of the complement displaced by the polymerase.

Hairpin adapter 218 having a single-stranded overhang complementary to a single-stranded overhang on product hairpin 217 is provided and ligated to the product hairpins in step 5, producing circular progeny nucleic acid 220. (It will be evident that where the product hairpin has or is modified to have blunt ends, a blunt ended hairpin adapter is provided.)

After the ligation reaction joining the hairpin adapter to the product hairpin to form the circular progeny nucleic acid has been performed, an exonuclease or combination of exonucleases (e.g., ExoIII and ExoVII) can be added to degrade any nucleic acids that have a free terminal nucleotide, for example, incomplete copies of the template that were unable to form a product hairpin and ligate to the adapter, or nucleic acids including non-target sequences that were cleaved by the restriction enzyme and were unable to ligate to the adapter. As noted above, where the template was produced from a complex nucleic acid sample, some members of the resulting population of circular nucleic acids may include non-target sequences which may have also been amplified in the previous steps. To remove such non-target molecules, one or more additional endonucleases that do not cleave the template or the circular progeny nucleic acid comprising the target region can be added during the original digestion, during the ligation reaction, or after the ligation reaction. If added during the original digestion or the ligation reaction, the overhang(s) left by the additional endonuclease(s) should be distinct from that left by the endonuclease used to free the product hairpins to prevent ligation of the adapter to the overhangs created by the additional endonucleases. If the additional endonucleases are added after the ligation reaction and subsequent removal of the adapter and ligase enzyme, the overhang could be complementary to the adapter (or not). In either case, additional terminal nucleotides will be exposed that are susceptible to exonuclease degradation, allowing the removal of non-target nucleic acids by exonuclease treatment.

As noted, the double-stranded central region of the template includes a recognition site for a restriction endonuclease. This recognition site and/or the cleavage site (if distinct from the recognition site) can be located within the target region or in sequences adjacent to the target region and originating from the same source (e.g., flanking the target region in a double-stranded genomic fragment or other fragment used to produce the template). As another example, the recognition site and/or the cleavage site (if distinct from the recognition site) can be created by the union of the target region (or its flanking sequence) and one of the stem-loop adapters initially used to produce the template. This facilitates the use of a rare cutter enzyme (i.e., a restriction endonuclease with a recognition site that occurs rarely, e.g., a seven or eight base pair recognition site) to free the product hairpins from the concatameric product strand. Any non-target fragments that were present and were copied are unlikely to include the rare cutter's recognition site; these non-target copies will thus be unable to ligate to the hairpin adapter and are optionally removed by exonuclease digestion as detailed above. The cut pattern of the rare cutter on the template optionally includes an overhang derived from the target region or its flanking sequence, providing additional specificity since a hairpin adapter complementary to this overhang is unlikely to ligate to off-target molecules. A variety of suitable rare cutters are known in the art, e.g., NotI, AbsI, AscI, BbvCI, CciNI, FseI, MreI, PalAI, RigI, SdaI, and SgsI.

As another example, the recognition site (and/or cleavage site, if distinct from the recognition site) can be located near the end of the double-stranded region in sequence originally contributed by one of the stem-loop adapters used to produce the circular template (e.g., by ligation with a double-stranded genomic or other fragment containing the target region). Designing the recognition site into the original stem-loop adapter allows for greater control over placement of the recognition site and greater choice among enzymes to use (including, e.g., rare cutters), since essentially any restriction enzyme whose recognition site is not present in the target region (or elsewhere in the double-stranded central region of the template) can be employed.

Combination of such locations will be evident. For example, the recognition site can be located entirely in sequence originally contributed by one of the stem-loop adapters used to produce the circular template, partially in sequence originally contributed by one of the stem-loop adapters used to produce the circular template and partially in the target region, or entirely in the target region. Similarly, on each of the two strands, the enzyme can cut a site that is in sequence originally contributed by one of the stem-loop adapters used to produce the circular template, partially in sequence originally contributed by one of the stem-loop adapters used to produce the circular template and partially in the target region, or entirely in the target region.

A large number of suitable restriction endonucleases are well known in the art, and many are available, e.g., from New England Biolabs and other commercial vendors. Examples include, but are not limited to, type II restriction endonucleases, e.g., type HP restriction endonucleases that recognize and cleave within a palindromic or discontinuous palindromic sequence (e.g., EcoRI, EcoRV, BamHI, SmaI, and TspRI), type IIS restriction endonucleases, and artificial restriction enzymes such as zinc finger DNA-binding protein nucleases (ZFNs), such as those commercially available from Sangamo BioSciences (Richmond, Calif.). ZFNs can be engineered so that their zinc finger domains bind specifically to a particular nucleotide sequence of interest, thereby directing the nuclease activity to that sequence. For more information on ZFNs, see U.S. Patent Publication Nos. 2009/0305419 and 2011/0287512, incorporated herein by reference in their entireties for all purposes.

As noted above, where the template was produced from a complex nucleic acid sample, some members of the resulting population of circular nucleic acids may include non-target sequences which may have also been amplified in the previous steps. Use of a type IIS restriction endonuclease to free the product hairpins from the concatameric product can assist in selecting target rather than non-target sequences for circularization during production of the circular progeny nucleic acid. A type IIS restriction enzyme cuts at a site that is not within its recognition sequence, so can provide overhangs that are random (in the sense that sequence of the overhang is not determined by that of the recognition sequence). In a population of fragments generated by digestion of a complex sample with a type IIS enzyme, the overhangs on different fragments will be different depending on what sequence was adjacent to the recognition site in the nucleic acid from which each fragment was generated; a mixture of overhangs whose sequence is not dependent on the sequence of the enzyme's recognition site is thus generated. Where the sequence around a target region is known, the overhang generated by a type IIS restriction enzyme that cuts in this sequence is thus also known. This knowledge allows the design of an adapter specific for the overhang generated adjacent to the target region. Typically, cleavage by type IIS restriction enzymes generates a three to four base overhang having a random sequence. Some preferred type IIS restriction enzymes generate longer random overhangs of five bases or more (e.g., HgaI), which provides an even more stringent selection for target sequences since a given "five-mer" will occur less frequently on average than will a shorter sequence, and the complementary adapter will therefore be ligated to fewer non-target fragments. Table 1 provides some examples of type IIS restriction enzymes, including their recognition sequence, cut site, and overhang produced. Others are known in the art, including, but not limited to, BsaI, BfuAI, FokI, BaeI, and AcuI.

TABLE 1

Exemplary Type IIs Restriction Enzymes

| RE | Sequence | Cut site | Overhang |
|---|---|---|---|
| BsmAI | GTCTC | G T C T C N/N N N N<br>C A G A G N N N N N/ | 5'-NNNN |
| SfaNI | GCATC | G C A T C N N N N N/N N N N<br>C G T A G N N N N N N N N N/ | 5'-NNNN |
| BsaI | GGTCTC | G G T C T C N/N N N N<br>C C A G A G N N N N N/ | 5'-NNNN |
| BsmBI | CGTCTC | C G T C T C N/N N N N<br>G C A G A G N N N N N/ | 5'-NNNN |
| BspMI | ACCTGC | A C C T G C N N N N/N N N N<br>T G G A C C N N N N N N N N/ | 5'-NNNN |
| SapI | GCTCTTC | G C T C T T C N/N N N<br>C G A G A A G N N N N/ | 5'-NNN |
| HgaI | GACGC | G A C G C N N N N N/N N N N N<br>C T G C G N N N N N N N N N N/ | 5'-NNNNN |

Since the type IIS restriction enzymes create random overhangs, any particular overhang sequence is only created at a small portion of the total cut sites. Where the overhang adjacent to the region of interest is known, an adapter can be used that will anneal and be ligated to product hairpins containing the target region. Few non-target nucleic acids will have an overhang complementary to the adapter and so will not be circularized. Such nucleic acids having a free end can be removed by exonuclease digestion as detailed above. In embodiments in which a primer sequence is also provided in the hairpin adapter, non-target nucleic acids unable to be ligated to the adapter will not be able to serve as templates in a next step (e.g., a successive round of amplification, nucleic acid sequencing, etc.). As described above, the recognition site for the type IIS enzyme is optionally found in sequence flanking the target region from its original source, is created by the junction of the target region and a stem-loop adapter used to produce the template, or, most conveniently, is provided in the stem of the stem-loop adapter used to produce the template. Preferably, the cleavage site for the type IIS enzyme is within the target region, e.g., just inside the target region such that the target region is regenerated by ligation of the hairpin adapter. For additional details on enrichment of desired targets using rare cutting enzymes, type HS enzymes, product circularization, and/or exonuclease digestion, see U.S. patent application 61/789,354 "Compositions and Methods for Selection of Nucleic Acids" filed Mar. 15, 2013 and U.S. patent application Ser. No. 14/069,067, each of which is incorporated herein by reference in its entirety for all purposes.

From each template, the methods generally produce at least one product hairpin and circular progeny nucleic acid, depending on the number of copies of the complement of the template in the product concatamer and its configuration as noted above. For example, for each template molecule, at least three, at least five, at least 10, at least 20, at least 30, at least 40, or at least 50 product hairpins and therefore circular progeny nucleic acids can be produced. For some applications, the degree of amplification achieved by a single round of amplification is sufficient. Where additional copies of the target sequence are desired, however, the circular progeny nucleic acid produced by the first round of amplification can be employed as the template in a second round of amplification.

Accordingly, in one class of embodiments, the circular progeny nucleic acid comprises a primer binding sequence, and the primer binding and primer extension steps detailed above are repeated to produce additional copies of the target region. The circular progeny nucleic acid can also comprise a recognition site for a restriction endonuclease, and the restriction digest can also be repeated. Similarly, a suitable hairpin adapter can be ligated to the resulting product hairpins to circularize them.

The primer binding sequence included in the circular progeny nucleic acid can be the same as that in the original template. In such embodiments, the same primer is optionally employed in both rounds of amplification. In other embodiments, the circular progeny nucleic acid includes a primer binding sequence different from that of the template, and a different primer is employed in the second round of amplification. The hairpin adapter used to produce the circular progeny nucleic acid can, e.g., include the primer binding sequence, or the single-stranded hairpin end region of the template distal from the restriction site can include the complement of the primer binding sequence such that the copy includes the primer binding sequence. As another example, the primer binding sequence can be formed by ligation of the hairpin adapter to the product hairpin. Like the template nucleic acid, the circular progeny nucleic acid optionally includes two or more primer binding sequences, e.g., one in each hairpin end region.

Similarly, the restriction enzyme recognition site included in the circular progeny nucleic acid can be the same as that in the original template. The same restriction enzyme or an isochizomer can be used. The hairpin adapter employed can be the same as or different from that used in the first round of amplification. In other embodiments, the circular progeny nucleic acid includes a different recognition site for a different restriction endonuclease, and that enzyme is employed in the second round. In embodiments in which the restriction enzyme employed in the second round of amplification leaves a different type of overhang (e.g., blunt, 5' single-stranded, or 3' single-stranded) or different sequence overhang, a different hairpin adapter suitable for that overhang will also be used in the second round when the product hairpins are circularized.

Rounds of amplification can be repeated as needed to achieve the desired degree of amplification of the target region, using circular progeny nucleic acids produced in the previous round(s) as template and employing suitable primer(s), restriction enzyme(s), adapter(s), etc. Essentially all of the features noted above for the first round of amplification are applicable to the second round, or any successive round(s), as well, as applicable. For example, the restriction site in the circular progeny nucleic acid can be proximal or distal to the primer binding sequence as detailed above for the first round of amplification. The hairpin adapter employed in the second round optionally includes a primer binding sequence and/or contains or introduces a restriction recognition site to the ligation product. Exonuclease treatment can be employed to remove incomplete products and/or off-target nucleic acids that are not circularized.

The various steps (primer binding, primer extension, restriction digestion, ligation, etc.) can be performed sequentially or concurrently. That is, each step can be completed, and any enzyme used in that step, excess adapter, cut off loops, incomplete products, etc. are optionally removed, before the reagents to initiate the next step are added, or various steps can be performed in a single reaction mixture containing all the necessary reagents. For example, digestion with the restriction endonuclease can be performed after primer extension is complete, or it can be performed as the primer is still being extended, e.g., to cleave the product hairpins as more are being synthesized. Performing the restriction digestion concurrently with the primer extension reaction can be advantageous, since sufficient time to ensure that the digestion is complete can be allotted while reducing the overall time required to complete the amplification process. In addition, restriction can reduce the topological complexity of the product strand.

Similarly, ligation of the hairpin adapter to the product hairpins can be performed after the restriction digest is complete, or the digestion and ligation reactions can be performed concurrently. Performing the digestion and ligation concurrently can reduce the overall time required to complete the amplification process, and, in embodiments where the restriction enzyme leaves a single-stranded overhang, ligation of the adapter to the product hairpin can prevent polishing of the end by the polymerase.

Optionally, the primer extension, restriction digestion, and ligation steps are performed concurrently, further decreasing the time required to complete the amplification process as well as realizing other benefits noted above.

In embodiments in which the restriction enzyme is present while primer extension or ligation is occurring, nucleic acids other than the concatameric product are optionally protected from cleavage by the restriction endonuclease. For example, in embodiments in which primer extension and restriction digestion are performed in the same reaction mixture, the template can be protected from cleavage by the restriction enzyme. For example, a methylation-sensitive restriction endonuclease and an appropriately methylated template that is not subject to cleavage by the enzyme (e.g., a template appropriately methylated at the enzyme's recognition site) can be employed. Similarly, in embodiments in which restriction digestion and ligation are performed in the same reaction mixture, the circular progeny nucleic acid can be protected from cleavage by the restriction enzyme by using a methylation-sensitive restriction enzyme and a methylated hairpin adapter such that the circular progeny nucleic acid is not cleaved by the enzyme. Where primer extension, restriction, and ligation are all performed the same mixture, the template and hairpin adapter can both be appropriately methylated and a methylation-sensitive restriction enzyme employed. A variety of suitable methylation-sensitive enzymes are well known in the art. As another example, the template and/or hairpin adapter can incorporate one or more mispaired bases, nucleotide analogs, and/or backbone modifications at the recognition or cleavage site that do not interfere with activity of the polymerase but that result in the restriction enzyme being unable to recognize or unable to cut that site, e.g., glucopyranosyloxymethyluracil (also known as base J) or 8-oxoguanine (8-hydroxyguanine or 8-oxo-G).

Performing the steps concurrently also permits multiple rounds of amplification to be performed in the same reaction mixture. Thus, in one class of embodiments, the primer extension, digesting, and ligating steps to produce a first circular progeny nucleic acid and the primer extension, digesting, and ligating steps to produce a second circular progeny nucleic acid using the first progeny nucleic acid as a template are performed in a single reaction mixture. Performing all the steps for two, three, or even more rounds of amplification concurrently in the same reaction mixture allows exponential amplification of the target region to occur without need for thermal cycling (in embodiments in which the primer binding site is proximal to the restriction site). Primer(s), polymerase, adapter(s), and other reagents can be replenished at intervals as needed to maintain cycling, or the reagents can be initially supplied in sufficient quantity to achieve the desired degree of amplification without addition of more reagents.

The template and/or resulting circular progeny nucleic acids can optionally be protected from cleavage by the restriction enzyme(s), e.g., as noted above. It will also be appreciated by a skilled practitioner that even without the benefit of protection from digestion, strands of DNA that are susceptible to cutting will be re-ligated, and will thus cycle between cut and mended states. By suitable selection of concentration of ligase and endonuclease, the fraction of the time that a molecule spends in the cut state can be adjusted. Since the purposes of the cut state and mended state are different, in many embodiments such cycling can be tolerated. For example, when a hairpin adapter is cleaved off a circular progeny nucleic acid, the adapter (or another copy of the adapter) can be re-ligated back on. Generally, the template and/or resulting circular progeny nucleic acid can be cut and mended repeatedly, and as long as it is able to serve as an uninterrupted template on average at least more than once per molecule, exponential population growth will still proceed. Preferably, the template and/or resulting circular progeny nucleic acid will allow uninterrupted synthesis three time or more or even more preferably five times or more, before the polymerase encounters the cleavage site in the cut state and polymerization is terminated (either irreversibly or for a protracted period).

The same primer is optionally employed in different rounds of amplification. Where different primers are used for different rounds of amplification performed concurrently, the primers are preferably not complementary to each other to avoid problems introduced by hybridization of the primers to each other. This can be achieved, for example, by targeting the primers to different parts of the hairpin loop in one (or both) of the single-stranded end regions. Another way to ensure that the primers are not complementary to each other is to use an asymmetric circular nucleic acid structure in which the hairpin loops at the two ends of the molecule are different from each other, and to design one of the primers to target the first end and the second primer to target the other end. In this way complete design freedom can be achieved to avoid complementarity between the primers. Another way to avoid self-complementarity is to use a single primer sequence and arrange an asymmetric circular nucleic acid structure such that the single primer targets the first end in even rounds of amplification and the second end in odd rounds of amplification. A related way of applying a single primer is to make one (or both) of the hairpin regions contain a palindrome. In this way the same primer will be able to complement with either sense of the hairpin end region's sequence. The palindrome will tend to make the hairpin collapse onto itself, but by selection of a suitably short primer sequence, the structure will oscillate between the open and closed state and will still be available for priming at a reduced reaction rate. However, once primed, the structure will be locked in place by the addition of nucleotides and subsequent steps will not be influenced. A combination of the above tactics can be used; for example, two primer sequences can be partly palindromic and partly targeting different regions of the hairpin.

Optionally, initiation of the second or later round of primer extension is coupled to ligation of the hairpin adapter to the product hairpin, such that extension of the primer while it is bound only to the hairpin adapter is avoided. For example, ligase can be pre-bound to the hairpin adapter to prevent polymerization from proceeding through the stem of the hairpin until ligation of the adapter to the product hairpin releases the ligase and permits polymerization to proceed. As another example, the primer binding site can be protected by secondary structure formation until ligation is complete. As one example of this, the hairpin adapter can be bistable, with the primer binding site completely or partially unavailable in a stem until ligation of the adapter to the product hairpin triggers a shift to a conformation in which the primer binding site is exposed in the single-stranded loop region of the hairpin. As another example, the primer binding site for the second (or subsequent) round of amplification can be formed by ligation of the hairpin adapter to the product hairpin. That is, the primer binding site spans (e.g., is centered on or nearly centered on) the junction of the adapter and the product hairpin. Invasion of the primer into the primer binding site such that thermal cycling is unnecessary can be assisted as noted above, e.g., by providing a primer (e.g., of 30 nucleotides or more) complexed with RecA or another recombinase agent as described in EP 2428588 "Recombinase Polymerase Amplification"; auxiliary enzymes are optionally also provided. Exemplary recombinases are commercially available, e.g., from TwistDx Ltd.

By performing two or more rounds of amplification, essentially any desired number of copies of the target region can be produced. For example, for each template molecule originally provided, at least 400, at least 900, at least 1600, or at least 2500 product hairpins and therefore circular progeny nucleic acids can be produced from two cycles of amplification.

When extension of primers bound to the concatameric product strand begins before restriction digestion releases the product hairpins from the concatamer, a hyperbranched structure can result. Such structures can be readily resolved by restriction digestion, e.g., after the primer extension step is complete or during extension.

As will be apparent to those of skill in the art, in any of these reactions comprising multiple different enzymes acting simultaneously, the reaction conditions must support the activity of all enzymes present. As such, care must be taken when choosing various nucleases and ligases to ensure their reaction conditions are compatible with each other and/or with the polymerase, as applicable. Where selected enzymes are not compatible, a staged approach can be implemented in which reaction conditions are adjusted to accommodate different stages in the reaction. Suitable reaction conditions for polymerases, endonucleases, and ligases are well known in the art.

At any desired point (e.g., after each step of the methods, after one or more selected steps of the methods, or after production of the circular progeny nucleic acid is complete), enzyme(s), excess adapters, incomplete products, unneeded cleavage products, and/or adapter-dimers formed during the reaction can be removed by subsequent purification. Size-selection methods are especially preferred. Optionally, the sample is subjected to size-selection strategies to isolate nucleic acids having a size consistent with the known size of the desired nucleic acid (e.g., the product hairpin or the circular progeny nucleic acid). A variety of size-selection techniques are known in the art, and many products are commercially available. Such methods include, but are not limited to, bead-, gel-, chromatography-, and density-based methods, e.g., SPRI (solid phase reversible immobilization) bead-based methods such as AMPure® bead-based methods (Beckman Coulter, Brea, Calif.).

Release of Product Fragments with Restriction Endonucleases

Although the previous embodiments have been described with reference to a template having a single restriction site on one side of the target region, it will be evident that the template optionally also includes a recognition site (for the same or different enzyme) on the opposite side of the target region, such that digestion of the concatameric product with both enzymes releases double-stranded fragments including the target region. Thus, in one class of embodiments, the double-stranded portion of the template nucleic acid includes two restriction endonuclease recognition (and cleavage) sites that flank the target region. The double-stranded portions of the concatenated hairpins formed by the displaced product strand thus also contain both restriction sites. The two recognition sites can have the same sequence and a single enzyme can be employed, or the two sites can have different sequences and be cut by different enzymes. Digestion of the product with the restriction enzyme(s) thus releases at least one product fragment. Typically, the digestion releases two or more product fragments, up to the number of complete copies of the complement that were displaced by the polymerase.

The product fragments released after the restriction digestion include a double-stranded region that comprises the target region. The product fragments can be blunt ended, have 5' single-stranded overhangs, have 3' single-stranded overhangs, or any combination thereof, depending on the cleavage pattern of the particular restriction enzyme(s) employed.

The product fragments can be employed in essentially any desired application, e.g., sequence determination, copy number determination, subsequent molecular cloning steps, mutagenesis, or the like. For example, if desired, a hairpin adapter can be ligated to each end of the fragment to produce a circular progeny nucleic acid. The same type of adapter or different types of adapters can be ligated to the two ends, depending, e.g., on the type of ends left on the fragment by the enzyme(s) employed. Similar to the circular nucleic acid template, the circular progeny nucleic acid has a double-stranded central region comprising the target region and has two single-stranded hairpin end regions. The loops of the end regions are derived from the hairpin adapter(s). The circular progeny nucleic acid optionally also includes one or more primer binding site and/or restriction site.

A suitable hairpin adapter includes two complementary nucleic acid segments separated by a stretch of non-complementary nucleotides. The resulting structure includes a double-stranded stem formed by the complementary segments and a single-stranded loop. The stem can be blunt ended, or it can include a 5' single-stranded overhang or a 3' single-stranded overhang. It will be evident that where the adapter is to ligate to a blunt end of the fragment (e.g., a product fragment produced by digestion with a restriction endonuclease that leaves blunt ends, or a product produced by digestion with a restriction endonuclease that leaves a single-stranded overhang followed by polishing with a polymerase to fill in a 5' overhang or remove a 3' overhang), the adapter is preferably blunt ended. Where the adapter is to ligate to a fragment having an overhang, the adapter preferably has a complementary overhang, e.g., a single-stranded overhang that is complementary to a single-stranded overhang on the product fragment.

In embodiments in which both ends of the product fragment have the same overhang or both are blunt ended, a single type of hairpin adapter can be employed. As another example, different types of hairpin adapters can be employed and randomly ligated to the ends of the fragment. As another example, where two enzymes leaving the same ends are employed but different adapters are desired to be ligated to the two ends of the fragment, digestion can be performed with one enzyme and an adapter can be ligated to that end, and then digestion can be performed with the other enzyme and another adapter can be ligated to that end. In embodiments in which the two ends of the product fragment have different types of overhangs, different sequences in the overhangs, or the like, two different adapters can be employed. As one example, a first hairpin adapter having a single-stranded overhang that is complementary to a single-stranded overhang on one end of a product fragment and a second hairpin adapter having a single-stranded overhang that is complementary to a single-stranded overhang on the other end of the product fragment can be employed. As another example, a first hairpin adapter having a blunt end to ligate to a blunt end on a product fragment and a second hairpin adapter having a single-stranded overhang that is complementary to a single-stranded overhang on the other end of the product fragment can be employed.

Suitable hairpins are readily designed and synthesized using conventional nucleic acid synthesis techniques. The adapter(s) can be present during the restriction digestion or can be added subsequently to the reaction mixture. The adapter(s) are typically provided in excess, e.g., to speed the reaction and to discourage re-ligation between the product fragment and the loop regions removed from it by the restriction enzyme(s). Although hairpin adapters provide a convenient technique for circularizing the product fragment, any of the other linking oligonucleotides or techniques described in U.S. Pat. No. 8,153,375 can be employed instead or in addition. Anti-ligators (alligators) are optionally employed to reduce or prevent off-target ligation events, as described in U.S. patent application Ser. No. 14/069,067.

Figure 4:
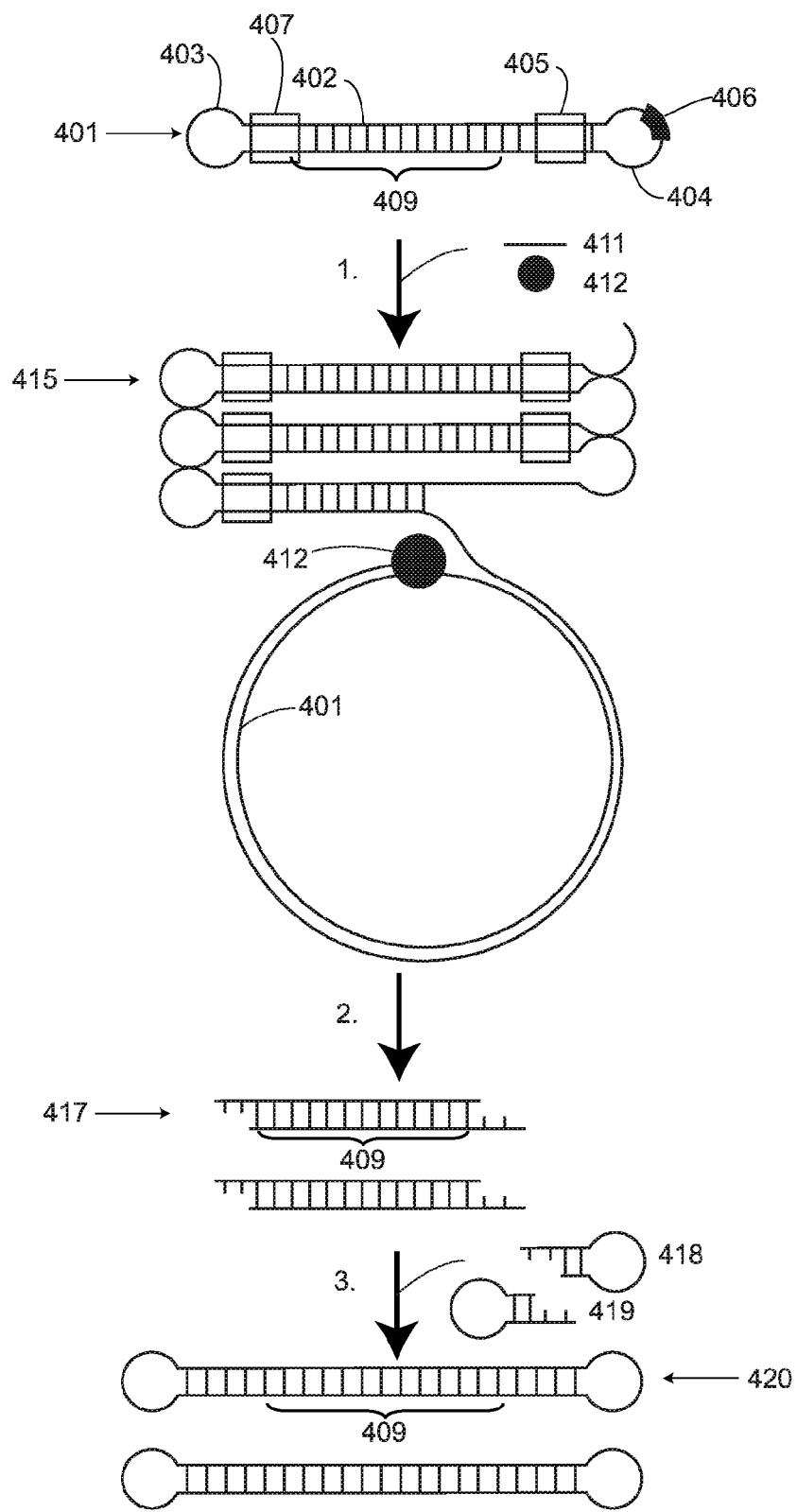
FIG. 4 schematically illustrates an exemplary amplification process in which restriction sites flank the target region.

The amplification process for a template in which there is a restriction site on each side of the target region is schematically illustrated in FIG. 4. As shown, nucleic acid template 401 is a circular nucleic acid having double-stranded central region 402 and single-stranded end regions 403 and 404. Double-stranded region 402 includes target region 409. Single-stranded end region 404 includes primer binding sequence 406. Target region 409 is located between recognition sites 405 and 407 for restriction enzymes (the same enzyme or different enzymes). The cleavage site for each of the restriction enzymes is most conveniently within or near the recognition site, as illustrated.

As illustrated in step 1, template 401 is complexed with primer 411, which binds to primer binding sequence 406, and strand-displacing polymerase 412 in the presence of the four standard nucleotides and/or analogs thereof. Polymerase 412 extends the primer. As synthesis continues, the polymerase displaces one complementary strand of double-stranded region 402 from the other. Upon completing one full cycle around the template, a double-stranded sequence including original template 401 and the newly synthesized strand results. Synthesis continues around template 401 multiple times as polymerase 412 continues to displace the newly synthesized nascent strand, producing product 415 containing multiple copies of the complement of the template. Self-complementary portions of nascent product strand 415 hybridize to each other as they are displaced by the polymerase, producing long concatenated hairpin structures. Since they are copies of template 401, the double-stranded portions of the concatenated hairpins formed by the displaced product strand also contain restriction sites 405 and 407. Digestion of product 415 with the restriction enzyme(s) thus releases at least one product fragment 417 as shown in step 2. Typically, digestion releases a number of product fragments equal to the number of complete copies of the complement that were displaced by the polymerase.

Hairpin adapters 418 and 419 having single-stranded overhangs complementary to the single-stranded overhangs on product fragment 417 are optionally provided and ligated to the product fragments in step 3, producing circular progeny nucleic acid 420. (It will be evident that where the product fragment has or is modified to have a blunt end, a blunt ended hairpin adapter is provided.)

As described for the embodiments above, after the ligation reaction joining the hairpin adapters to the product fragment to form the circular progeny nucleic acid has been performed, an exonuclease or combination of exonucleases (e.g., ExoIII and ExoVII) can be added to degrade any nucleic acids that have a free terminal nucleotide, for example, incomplete copies of the template that were unable to ligate to the adapter, or nucleic acids including non-target sequences that were cleaved by the restriction enzyme and were unable to ligate to the adapter. As noted above, where the template was produced from a complex nucleic acid sample, some members of the resulting population of circular nucleic acids may include non-target sequences which may have also been amplified in the previous steps. To remove such non-target molecules, one or more additional endonucleases that do not cleave the template or the circular progeny nucleic acid comprising the target region can be added during the original digestion, during the ligation reaction, or after the ligation reaction. If added during the original digestion or the ligation reaction, the overhang(s) left by the additional endonuclease(s) should be distinct from that left by the endonuclease used to free the product fragments to prevent ligation of the adapter to the overhangs created by the additional endonucleases. If the additional endonucleases are added after the ligation reaction and subsequent removal of the adapter and ligase enzyme, the overhang could be complementary to the adapter (or not). In either case, additional terminal nucleotides will be exposed that are susceptible to exonuclease degradation, allowing the removal of non-target nucleic acids by exonuclease treatment.

As noted, the double-stranded central region of the template includes a pair of recognition sites for at least one restriction endonuclease. Either or both of the two recognition sites (and/or of the cleavage sites, if distinct from the recognition sites) can be located within the target region or in sequences adjacent to the target region and originating from the same source (e.g., flanking the target region in a double-stranded genomic fragment or other fragment used to produce the template). As another example, either or both of the recognition sites (and/or of the cleavage sites, if distinct from the recognition site) can be created by the union of the target region (or its flanking sequence) and one of the stem-loop adapters initially used to produce the template. This facilitates the use of a rare cutter enzyme or a pair or rare cutters to free the product fragments from the concatameric product strand. Any non-target fragments that were present and were copied are unlikely to include the rare cutter's recognition site; these non-target copies will thus be unable to ligate to the hairpin adapter and are optionally removed by exonuclease digestion as detailed above. The cut pattern of the rare cutter on the template optionally includes an overhang derived from the target region or its flanking sequence, providing additional specificity since a hairpin adapter complementary to this overhang is unlikely to ligate to off-target molecules. A variety of suitable rare cutters are known in the art, as noted above.

As another example, either or both of the recognition sites (and/or of the cleavage sites, if distinct from the recognition sites) can be located near the end of the double-stranded region in sequence originally contributed by one of the stem-loop adapters used to produce the circular template (e.g., by ligation with a double-stranded genomic or other fragment containing the target region). Designing the recognition site into the original stem-loop adapter allows for greater control over placement of the recognition site and greater choice among enzymes to use (including, e.g., rare cutters), since essentially any restriction enzyme whose recognition site is not present in the target region (or elsewhere in the double-stranded central region of the template) can be employed.

Combination of such locations will be evident. For example, for each enzyme used, the recognition site can be located entirely in sequence originally contributed by one of the stem-loop adapters used to produce the circular template, partially in sequence originally contributed by one of the stem-loop adapters used to produce the circular template and partially in the target region, or entirely in the target region. Similarly, on each of the two strands, each enzyme can cut a site that is in sequence originally contributed by one of the stem-loop adapters used to produce the circular template, partially in sequence originally contributed by one of the stem-loop adapters used to produce the circular template and partially in the target region, or entirely in the target region.

A large number of suitable restriction endonucleases are well known in the art, as noted above. Also as noted above, where the template was produced from a complex nucleic acid sample, some members of the resulting population of circular nucleic acids may include non-target sequences which may have also been amplified in the previous steps. Use of a type IIS restriction endonuclease (alone or with another type of site-specific endonuclease) or a pair of type IIS restriction endonucleases to free the product fragments from the concatameric product can assist in selecting target rather than non-target sequences for circularization during production of the circular progeny nucleic acid. As detailed for the embodiments above, a hairpin adapter or pair of adapters specific for the overhang(s) generated adjacent to the target region can be designed when the sequence around the target region is known. Since the type IIS restriction enzymes create random overhangs, any particular overhang sequence is only created at a small portion of the total cut sites. Where the overhang(s) adjacent to the region of interest is known, adapter(s) can be used that will anneal and be ligated to product fragment containing the target region. Few non-target nucleic acids will have overhang(s) complementary to the adapter(s) and so will not be circularized. Such nucleic acids having a free end can be removed by exonuclease digestion as detailed above. In embodiments in which a primer sequence is also provided in the hairpin adapter, non-target nucleic acids unable to be ligated to the adapter will not be able to serve as templates in a next step (e.g., a successive round of amplification, nucleic acid sequencing, etc.). As described above, the recognition site for the type IIS enzyme is optionally found in sequence flanking the target region from its original source, is created by the junction of the target region and a stem-loop adapter used to produce the template, or, most conveniently, is provided in the stem of the stem-loop adapter used to produce the template. Preferably, the cleavage site for the type IIS enzyme is within the target region, e.g., just inside the target region such that the target region is regenerated by ligation of the hairpin adapter. For additional details on enrichment of desired targets using rare cutting enzymes, type IIS enzymes, product circularization, and/or exonuclease digestion, see U.S. patent application 61/789, 354 "Compositions and Methods for Selection of Nucleic Acids" filed Mar. 15, 2013 and U.S. patent application Ser. No. 14/069,067.

From each template, the methods generally produce at least one product fragment and optional circular progeny nucleic acid, depending on the number of copies of the complement of the template in the product concatamer. For example, for each template molecule, at least three, at least five, at least 10, at least 20, at least 30, at least 40, or at least 50 product fragments and therefore circular progeny nucleic acids can be produced. For some applications, the degree of amplification achieved by a single round of amplification is sufficient. Where additional copies of the target sequence are desired, however, the circular progeny nucleic acid produced by the first round of amplification can be employed as the template in a second round of amplification.

Accordingly, in one class of embodiments, the circular progeny nucleic acid comprises a primer binding sequence, and the primer binding and primer extension steps detailed above are repeated to produce additional copies of the target region. The circular progeny nucleic acid can also comprise a pair of recognition sites for a restriction endonuclease or endonucleases, and the restriction digest can also be repeated. Similarly, a suitable hairpin adapter or adapters can be ligated to the resulting product fragments to circularize them if desired.

The primer binding sequence included in the circular progeny nucleic acid can be the same as that in the original template. In such embodiments, the same primer is optionally employed in both rounds of amplification. In other embodiments, the circular progeny nucleic acid includes a primer binding sequence different from that of the template, and a different primer is employed in the second round of amplification. For example, a hairpin adapter used to produce the circular progeny nucleic acid can contribute all or part of the primer binding sequence. As another example, the primer binding sequence can be formed by ligation of one of the hairpin adapters to the product fragment. Like the template nucleic acid, the circular progeny nucleic acid optionally includes two or more primer binding sequences, e.g., one in each hairpin end region.

Similarly, the restriction enzyme recognition sites included in the circular progeny nucleic acid can be the same as those in the original template. The same restriction enzyme(s) or an isochizomer can be used. The hairpin adapter(s) employed can be the same as or different from the adapter(s) used in the first round of amplification. In other embodiments, the circular progeny nucleic acid includes different recognition sites for different restriction endonucleases, and those enzymes are employed in the second round. In embodiments in which the restriction enzyme(s) employed in the second round of amplification leave a different type of overhang (e.g., blunt, 5' single-stranded, or 3' single-stranded) or different sequence overhang than those in the first round, a different hairpin adapter or adapters suitable for those overhangs will also be used in the second round in embodiments in which the product fragments are circularized.

It will be evident that one enzyme or a pair of enzymes can be employed in the first round, and one enzyme or a pair of enzymes can be employed in the second round, chosen independently from those used in the first round. Employing a different enzyme or pair of enzymes in the second round (e.g., different rare cutters and/or type IIS enzymes) can provide additional enrichment for the desired target region, in the same manner as detailed for the first round above.

Rounds of amplification can be repeated as needed to achieve the desired degree of amplification of the target region, using circular progeny nucleic acids produced in the previous round(s) as template and employing suitable primer(s), restriction enzyme(s), adapter(s), etc. Essentially all of the features noted above for the first round of amplification are applicable to the second round, or any successive round(s), as well, as applicable. For example, a hairpin adapter employed in the second round optionally includes a primer binding sequence and/or contains or introduces a restriction recognition site to the ligation product. Exonuclease treatment can be employed to remove incomplete products and/or off-target nucleic acids that are not circularized.

As described for the embodiments above, the various steps (primer binding, primer extension, restriction digestion, ligation, etc.) can be performed sequentially or concurrently. That is, each step can be completed, and any enzyme used in that step, excess adapter, cut off loops, incomplete products, etc. are optionally removed, before the reagents to initiate the next step are added, or various steps can be performed in a single reaction mixture containing all the necessary reagents. For example, restriction digestion can be performed after primer extension is complete, or it can be performed as the primer is still being extended, e.g., to cleave the product fragments as more are being synthesized. Similarly, ligation of the hairpin adapter(s) to the product fragment can be performed after the restriction digest is complete, or the digestion and ligation reactions can be performed concurrently. Optionally, the primer extension, restriction digestion, and ligation steps are performed concurrently.

In embodiments in which the restriction enzyme(s) are present while primer extension or ligation is occurring, nucleic acids other than the concatameric product are optionally protected from cleavage. For example, in embodiments in which primer extension and restriction digestion are performed in the same reaction mixture, the template can be protected from cleavage by the restriction enzyme(s). For example, a methylation-sensitive restriction endonuclease and an appropriately methylated template that is not subject to cleavage by the enzyme (e.g., a template appropriately methylated at the enzyme's recognition site) can be employed. Similarly, in embodiments in which restriction digestion and ligation are performed in the same reaction mixture, the circular progeny nucleic acid can be protected from cleavage by the restriction enzyme(s) by using methylation-sensitive restriction enzyme(s) and methylated hairpin adapter(s) such that the circular progeny nucleic acid is not cleaved by the enzyme(s). Where primer extension, restriction, and ligation are all performed the same mixture, the template and hairpin adapter(s) can both be appropriately methylated and methylation-sensitive restriction enzyme(s) employed. A variety of suitable methylation-sensitive enzymes are well known in the art. As another example, the template and/or hairpin adapter(s) can incorporate one or more nucleotide analogs, mispaired bases, and/or backbone modifications at the recognition or cleavage site that do not interfere with activity of the polymerase but that result in the restriction enzyme being unable to recognize or unable to cut that site, e.g., glucopyranosyloxymethyluracil (also known as base J) or 8-oxoguanine (8-hydroxyguanine or 8-oxo-G).

Performing the steps concurrently also permits multiple rounds of amplification to be performed in the same reaction mixture. Thus, in one class of embodiments, the primer extension, digesting, and ligating steps to produce a first circular progeny nucleic acid and the primer extension and digesting steps to produce a second product fragment using the first progeny nucleic acid as a template are performed in a single reaction mixture. In embodiments in which the second product fragment is circularized, this circularization can also be performed in the same mixture. Performing all the steps for two, three, or even more rounds of amplification concurrently in the same reaction mixture allows exponential amplification of the target region to occur without need for thermal cycling. Primer(s), polymerase, adapter(s), and other reagents can be replenished at intervals as needed to maintain cycling, or the reagents can be initially supplied in sufficient quantity to achieve the desired degree of amplification without addition of more reagents. The template and/or resulting circular progeny nucleic acids can optionally be protected from cleavage by the restriction enzyme(s), e.g., as noted above, although, as detailed for the embodiments above, some cleavage and re-ligation can be tolerated. Where different primers are used for different rounds of amplification performed concurrently, the primers are preferably not complementary to each other to avoid problems introduced by hybridization of the primers to each other, as detailed above.

Optionally, initiation of the second or later round of primer extension is coupled to ligation the hairpin adapter(s) to the product fragment, such that extension of the primer while it is bound only to the hairpin adapter is avoided. For example, ligase can be pre-bound to the hairpin adapter to prevent polymerization from proceeding through the stem of the hairpin until ligation of the adapter to the product fragment releases the ligase and permits polymerization to proceed. As another example, the primer binding site can be protected by secondary structure formation until ligation is complete, e.g., using a bistable hairpin adapter as described above. As another example, the primer binding site for the second (or subsequent) round of amplification can be formed by ligation of one of the hairpin adapters (or both, when two primer binding sites are to be provided in the circular progeny nucleic acid) to the product fragment. That is, the primer binding site spans (e.g., is centered on or nearly centered on) the junction of the adapter and the product fragment. Invasion of the primer into the primer binding site can be assisted as noted above, e.g., by RecA or another recombinase agent.

Essentially all of the features noted for the methods above apply to these embodiments as well, as relevant, for example, with respect to the polymerase employed, type of target region, subsequent manipulation (e.g., sequencing) of the amplified target region, number of copies of the target region produced, resolution of hyperbranched structures, selection of reaction conditions, inclusion of purification steps, and/or the like.

Release of Product Hairpins with Nicking Endonucleases

In one class of embodiments, the double-stranded portion of the template nucleic acid includes a recognition site for a nicking endonuclease. The double-stranded portions of the concatenated hairpins formed by the displaced product strand thus also contain the recognition site, and nicking of the product with the nicking enzyme thus releases at least one product hairpin. Typically, cutting the product with the nicking enzyme releases two or more product hairpins, up to the number of complete copies of the complement that were displaced by the polymerase.

The product hairpins released through the nicking reaction generally include free 5' and 3' termini (typically, a free 5' phosphate group and a free 3' hydroxyl group) and a double-stranded region that comprises the target region. A single-stranded hairpin end region connects the two strands of the double-stranded region at one end of the hairpin. At the other end of the hairpin, a single-stranded extension can (at least transiently) form a short stem-loop structure.

The product hairpins can be employed in essentially any desired application, e.g., sequence determination, copy number determination, subsequent molecular cloning steps, mutagenesis, or the like. For example, the 5' terminus of each of the first product hairpins is optionally intramolecularly ligated to the 3' terminus to produce a circular progeny nucleic acid. Similar to the circular nucleic acid template, the circular progeny nucleic acid has a double-stranded central region comprising the target region and has two single-stranded hairpin end regions. The loop of one end region is complementary to that of one of the template's, and the loop of the other end region is complementary to the template's other end region. The circular progeny nucleic acid optionally also includes one or more primer binding site and/or enzyme recognition site.

Placement of the nick site can affect how the product hairpins are released. In one class of embodiments, the recognition site for the nicking enzyme is proximal to the primer binding sequence (that is, the recognition site is at the same end of the double-stranded target region as is the primer binding sequence). Preferred nicking enzymes include those having a cut site either near or within the recognition site; the nicking site for the nicking endonuclease is thus also proximal to the primer binding sequence.

Figure 3:
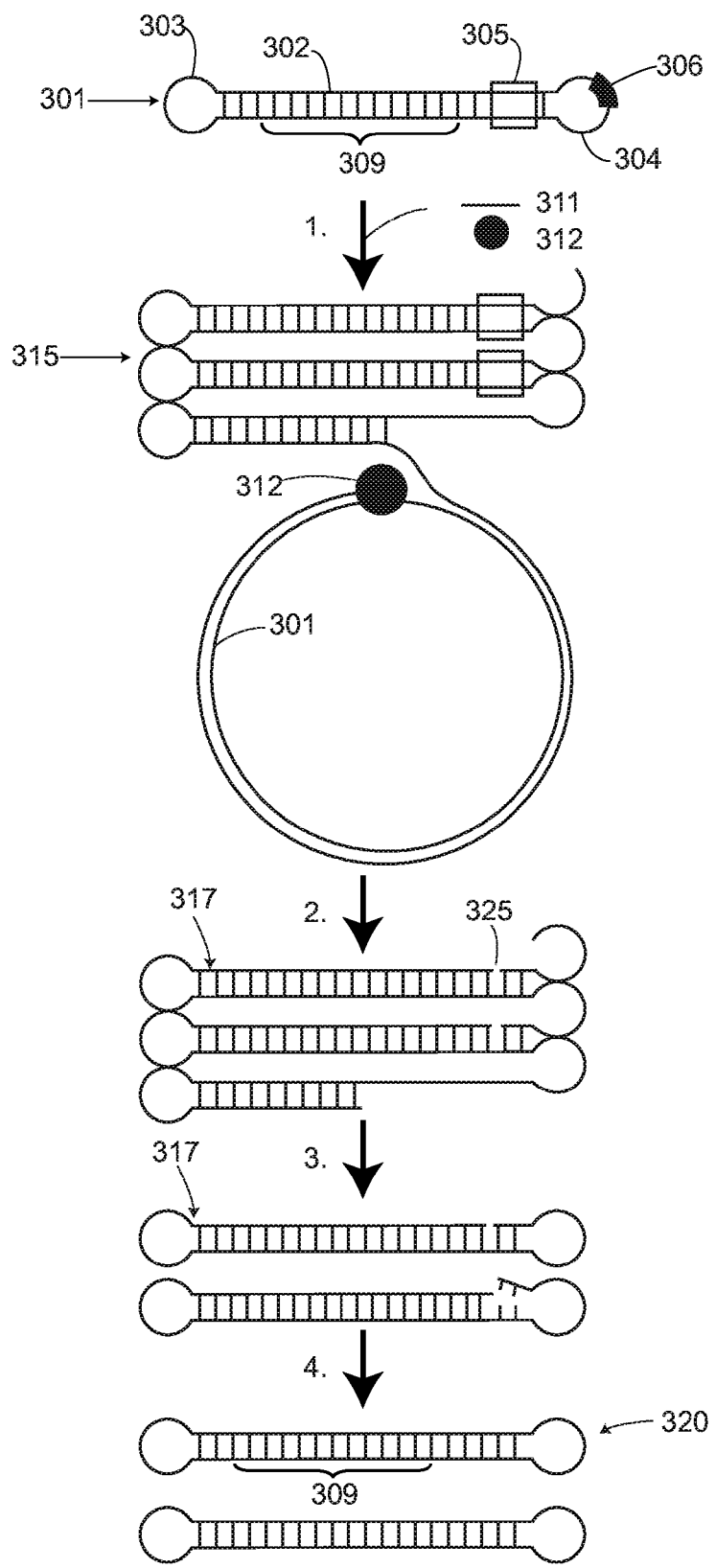
FIG. 3 schematically illustrates an exemplary amplification process in which a nicking site is proximal to the primer binding site.

The amplification process for a template in which the nick is proximal to the primer binding site is schematically illustrated in FIG. 3. As shown, nucleic acid template 301 is a circular nucleic acid having double-stranded central region 302 and single-stranded end regions 303 and 304. Double-stranded region 302 includes target region 309. Single-stranded end region 304 includes primer binding sequence 306. Recognition site 305 for a nicking endonuclease is located between target region 309 and primer binding sequence 306. The cut site for the nicking enzyme is most conveniently within or near the recognition site, as illustrated.

As illustrated in step 1, template 301 is complexed with primer 311, which binds to primer binding sequence 306, and strand-displacing polymerase 312 in the presence of the four standard nucleotides and/or analogs thereof. Polymerase 312 extends the primer. As synthesis continues, the polymerase displaces one complementary strand of double-stranded region 302 from the other. Upon completing one full cycle around the template, a double-stranded sequence including original template 301 and the newly synthesized strand results. Synthesis continues around template 301 multiple times as polymerase 312 continues to displace the newly synthesized nascent strand, producing product 315 containing multiple copies of the complement of the template. Self-complementary portions of nascent product strand 315 hybridize to each other as they are displaced by the polymerase, producing long concatenated hairpin structures. Since they are copies of template 301, the double-stranded portions of the concatenated hairpins formed by the displaced product strand also contain recognition site 305. Cutting of product 315 with the nicking endonuclease to produce nick 325 thus releases at least one product hairpin 317 as shown in step 2. Typically, nicking releases a number of product hairpins equal to the number of complete copies of the complement that were displaced by the polymerase.

As illustrated, adjacent product hairpins are initially daisy chained together through a short complementary region (between the nick and the nearby hairpin end region). Preferably, the length and/or sequence of this region and/or the reaction temperature are selected or adjusted such that the association between adjacent product hairpins is not stable, and the product hairpins dissociate from each other after the nick is formed. If necessary, however, the temperature of the reaction can be temporarily increased to favor dissociation and release of the product hairpins. For example, the short complementary region can be about 2 to 8 nucleotides in length for unstable association at room temperature, about 8 to 17 nucleotides in length for unstable association at an elevated constant temperature or for a reduced rate of dissociation at room temperature, or about 17 to 30 nucleotides in length in embodiments in which product hairpins are dissociated from their neighbors by a heating and reannealing step.

Intramolecular hybridization of this region is thermodynamically favored over hybridization between adjacent hairpins. The single-stranded extension can thus form a stem-loop structure, as shown in step 3, placing the 5' and 3' termini adjacent to each other at least transiently. Intramolecular ligation of the 5' and 3' termini produces circular progeny nucleic acid 320, as shown in step 4.

In another class of embodiments, the recognition site for the nicking endonuclease is distal to the primer binding sequence (that is, the recognition site is at the opposite end of the double-stranded target region from the primer binding sequence). Preferred nicking enzymes include those having a cleavage site either within or near the recognition site; the cut site for the nicking endonuclease is thus also distal to the primer binding sequence. In this class of embodiments, adjacent product hairpins tend to remain associated since they are hybridized to each other over most of the length of the double-stranded central region. The product hairpins can be separated, e.g., by increasing the temperature of the reaction mixture. Annealing (e.g., by decreasing the temperature the reaction mixture) results in hybridization of the self-complementary portions of individual molecules to produce product hairpins.

After the ligation reaction to form the circular progeny nucleic acid has been performed, an exonuclease or combination of exonucleases (e.g., ExoIII and ExoVII) can be added to degrade any nucleic acids that have a free terminal nucleotide, for example, incomplete copies of the template that were unable to form a product hairpin, or concatamers (e.g., including non-target sequences) that were not nicked by the nicking enzyme and were unable to circularize. As noted above, where the template was produced from a complex nucleic acid sample, some members of the resulting population of circular nucleic acids may include non-target sequences which may have also been amplified in the previous steps. To remove such non-target molecules, one or more additional endonucleases that do not cleave the template or the circular progeny nucleic acid comprising the target region can be added, e.g., after the ligation reaction, to expose additional terminal nucleotides that are susceptible to exonuclease degradation, allowing the removal of non-target nucleic acids by exonuclease treatment as detailed above.

As noted, the double-stranded central region of the template includes a recognition site for a nicking endonuclease. This recognition site and/or the nick site (if distinct from the recognition site) can be located within the target region or in sequences adjacent to the target region and originating from the same source (e.g., flanking the target region in a double-stranded genomic fragment or other fragment used to produce the template). As another example, the recognition site can be created by the union of the target region (or its flanking sequence) and one of the stem-loop adapters initially used to produce the template. This facilitates the use of a nicking enzyme with a recognition site that occurs rarely (e.g., a seven or eight base pair recognition site) to free the product hairpins from the concatameric product strand. Any non-target fragments that were present and were copied are unlikely to include the rare recognition site; these non-target copies will thus be unable to circularize and are optionally removed by exonuclease digestion as detailed above.

As another example, the recognition site (and/or cut site, if distinct from the recognition site) for the nicking enzyme can be located near the end of the double-stranded region in sequence originally contributed by one of the stem-loop adapters used to produce the circular template (e.g., by ligation with a double-stranded genomic or other fragment containing the target region). Designing the recognition site into the original stem-loop adapter allows for greater control over placement of the recognition site and greater choice among enzymes to use, since essentially any nicking endonuclease whose recognition site is not present in the target region (or elsewhere in the double-stranded central region of the template) can be employed.

A number of suitable nicking endonucleases are well known in the art, and many are available from commercial vendors. Table 2 provides some examples of nicking endonucleases commercially available, e.g., from New England Biolabs, including their recognition sequence and cut site.

TABLE 2

Exemplary Nicking Endonucleases

| Nicking Endonuclease | Cut site |
|---|---|
| Nt.BspQI | G C T C T T C N/<br>C G A G C C G N |
| Nt.BstNBI | G A G T C N N N N/N<br>C T C A G N N N N N |
| Nb.BsrDI | G C A A T G N N<br>C G T T A C/N N |
| Nb.BtsI | G C A G T G N N<br>C G T C A C/N N |
| Nt.AlwI | G G A T C N N N N/N<br>C C T A G N N N N N |
| Nb.BbvCI | C C T C A G C<br>G G A G T/C G |
| Nt.BbvCI | C C/T C A G C<br>G G A G T C G |
| Nb.BsmI | G A A T G C N<br>C T T A C/G N |

From each template, the methods generally produce at least one product hairpin and circular progeny nucleic acid, depending on the number of copies of the complement of the template in the product concatamer and its configuration as noted above. For example, for each template molecule, at least three, at least five, at least 10, at least 20, at least 30, at least 40, or at least 50 product hairpins and therefore circular progeny nucleic acids can be produced. For some applications, the degree of amplification achieved by a single round of amplification is sufficient. Where additional copies of the target sequence are desired, however, the circular progeny nucleic acid produced by the first round of amplification can be employed as the template in a second round of amplification.

Accordingly, in one class of embodiments, the circular progeny nucleic acid comprises a primer binding sequence, and the primer binding and primer extension steps detailed above are repeated to produce additional copies of the target region. The circular progeny nucleic acid can also comprise a recognition site for a nicking endonuclease, and the nicking reaction can also be repeated. Similarly, the resulting product hairpins can be circularized by ligation.

The same primer can be employed in both rounds of amplification. Preferably, however, the circular progeny nucleic acid includes a primer binding sequence different from that of the template, and a different primer is employed in the second round of amplification. In one class of embodiments, a first primer is employed in the first round of amplification and a second primer is employed in the second round, the first primer binding sequence and the complement of the second primer binding sequence are in one of the two single-stranded hairpin end regions of the template, and the second primer binding sequence and the complement of the first primer binding sequence are thus in one single-stranded hairpin end region of the first circular progeny nucleic acid. Like the template nucleic acid, the circular progeny nucleic acid optionally includes two or more primer binding sequences.

The recognition site for the nicking enzyme included in the circular progeny nucleic acid can be the same as that in the original template, and the same nicking enzyme or can be used. In other embodiments, the circular progeny nucleic acid includes a different recognition site for a different nicking endonuclease, and that enzyme is employed in the second round.

Rounds of amplification can be repeated as needed to achieve the desired degree of amplification of the target region, using circular progeny nucleic acids produced in the previous round(s) as template and employing suitable primer(s), nicking enzyme(s), adapter(s), etc. Essentially all of the features noted above for the first round of amplification are applicable to the second round, or any successive round(s), as well, as applicable. For example, the recognition site in the circular progeny nucleic acid can be proximal or distal to the primer binding sequence as detailed above for the first round of amplification. Exonuclease treatment can be employed to remove incomplete products and/or off-target nucleic acids that are not circularized.

The various steps (primer binding, primer extension, nicking, ligation, etc.) can be performed sequentially or concurrently. That is, each step can be completed, and any enzyme used in that step, incomplete products, etc. are optionally removed, before the reagents to initiate the next step are added, or various steps can be performed in a single reaction mixture containing all the necessary reagents with advantages similar to those described above for the embodiments employing restriction enzymes. For example, nicking can be performed after primer extension is complete, or it can be performed as the primer is still being extended, e.g., to release the product hairpins as more are being synthesized. Similarly, ligation of the product hairpins can be performed after the nicking reaction is complete, or the nicking and ligation reactions can be performed concurrently. Optionally, the primer extension, nicking, and ligation steps are performed concurrently, decreasing the time required to complete the amplification process.

In embodiments in which primer extension and nicking are performed in the same reaction mixture, the template can be protected from nicking by the enzyme. For example, a methylation-sensitive nicking endonuclease and an appropriately methylated template that is not subject to being cut by the enzyme (e.g., a template appropriately methylated at the enzyme's recognition site) can be employed, or the template can incorporate one or more mispaired bases, nucleotide analogs and/or backbone modifications at the recognition or cleavage site that do not interfere with activity of the polymerase but that result in the nicking enzyme being unable to recognize or unable to cut that site, e.g., glucopyranosyloxymethyluracil (also known as base J) or 8-oxoguanine (8-hydroxyguanine or 8-oxo-G).

Performing the steps concurrently also permits multiple rounds of amplification to be performed in the same reaction mixture. Thus, in one class of embodiments, the primer extension, nicking, and ligating steps to produce a first circular progeny nucleic acid and the primer extension, nicking, and ligating steps to produce a second circular progeny nucleic acid using the first progeny nucleic acid as a template are performed in a single reaction mixture. Performing all the steps for two, three, or even more rounds of amplification concurrently in the same reaction mixture allows exponential amplification of the target region to occur without need for thermal cycling (e.g., in embodiments in which the primer binding site is proximal to the nick site and the product hairpins dissociate readily after nicking). Primer(s), polymerase, and other reagents can be replenished at intervals as needed to maintain cycling, or the reagents can be initially supplied in sufficient quantity to achieve the desired degree of amplification without addition of more reagents.

The template and/or resulting circular progeny nucleic acids can optionally be protected from nicking by the endonuclease, e.g., as noted above. It will also be appreciated by a skilled practitioner that even without the benefit of protection from nicking, strands of DNA that are susceptible to cutting will be re-ligated, and will thus cycle between cut and mended states. By suitable selection of concentration of ligase and endonuclease, the fraction of the time that a molecule spends in the cut state can be adjusted. Since the purposes of the cut state and mended state are different, in many embodiments such cycling can be tolerated. For example, when single-stranded nicking near a hairpin loop results in release of a product hairpin from the concatameric nascent product strand, this will be an irreversible reaction due to the increased positional entropy of the departed fragment. The gap that remains in the product hairpin afterward will be ligated, and this site can then be nicked and mended repeatedly and as long as the circular progeny nucleic acid is able to serve as an uninterrupted template on average at least more than once per molecule, exponential population growth will still proceed. Preferably, the template and/or circular progeny nucleic acid will allow uninterrupted synthesis three time or more or even more preferably five times or more, before the polymerase encounters the nicking site in the cut state and the polymerization is terminated (either irreversibly or for a protracted period).

Where different primers are used for different rounds of amplification performed concurrently, the primers are preferably not complementary to each other to avoid problems introduced by hybridization of the primers to each other, as detailed above.

Optionally, initiation of the second or later round of primer extension is coupled to ligation of the product hairpin, such that only already circularized product hairpins serve as templates. For example, the primer binding site for the second (or subsequent) round of amplification can be formed by the intramolecular ligation of the product hairpin. That is, the primer binding site spans (e.g., is centered on or nearly centered on) the nick site. Since the nick site is typically near or within the recognition site, the primer binding sequence can thus include the recognition site for the nicking endonuclease. Invasion of the primer into the primer binding site such that thermal cycling is unnecessary can be assisted as noted above, e.g., by providing a primer (e.g., of 30 nucleotides or more) complexed with RecA or another recombinase agent (optionally with auxiliary enzymes) as described in EP 2428588 "Recombinase Polymerase Amplification." Exemplary recombinases are available, e.g., from TwistDx Limited.

Optionally, the primer used in the second or later round of extension includes a 5' "tail" (an extension functionally equivalent to the extension at the end of a product hairpin as described above), such that, if primer extension begins before the product hairpin has been circularized, the resulting linear double-stranded product can be denatured and each of the two strands can be circularized by intramolecular ligation. The sequence of the 5' tail should be chosen such that it contains a portion homologous to the complement of the product hairpin from the nick site to the nearby end of the double-stranded region. Mismatched bases within the binding footprint of the endonuclease or the ligase should be avoided, as these might interfere with the efficacy of later steps. The 5' end of the primer should be prepared so as to be competent for ligation. For example, if the ligase to be used requires a 5' phosphate, then the oligonucleotide should be phosphorylated at the 5' terminus. Several different ligases and options for deployment of ligases are known in the art that call for different treatment of the 5' ends, and one of ordinary skill will know how to select a 5' end that will allow ligation.

By performing two or more rounds of amplification, essentially any desired number of copies of the target region can be produced. For example, for each template molecule originally provided, at least 400, at least 900, at least 1600, or at least 2500 product hairpins and therefore circular progeny nucleic acids can be produced from two cycles of amplification.

When extension of primers bound to the concatameric product strand begins before restriction digestion releases the product hairpins from the concatamer, a hyperbranched structure can result. Such structures can be readily resolved by restriction digestion, e.g., after the primer extension step is complete or during extension.

As will be apparent to those of skill in the art, in any of these reactions comprising multiple different enzymes acting simultaneously, the reaction conditions must support the activity of all enzymes present. As such, care must be taken when choosing various nucleases and ligases to ensure their reaction conditions are compatible with each other and/or with the polymerase, as applicable. Where selected enzymes are not compatible, a staged approach can be implemented in which reaction conditions are adjusted to accommodate different stages in the reaction. Suitable reaction conditions for polymerases, endonucleases, and ligases are well known in the art.

At any desired point (e.g., after each step of the methods, after one or more selected steps of the methods, or after production of the circular progeny nucleic acid is complete), enzyme(s), incomplete products, and/or inappropriately ligated nucleic acids can be removed by subsequent purification. Size-selection methods are especially preferred. Optionally, the sample is subjected to size-selection strategies to isolate nucleic acids having a size consistent with the known size of the desired nucleic acid (e.g., the product hairpin or the circular progeny nucleic acid). A variety of size-selection techniques are known in the art, and many products are commercially available. Such methods include, but are not limited to, bead-, gel-, chromatography-, and density-based methods, e.g., SPRI (solid phase reversible immobilization) bead-based methods such as AMPure® bead-based methods (Beckman Coulter, Brea, Calif.).

Although the previous embodiments have been described with reference to a template having a single nicking site on one side of the target region, it will be evident that the template optionally also includes a recognition site (for the same or different nicking enzyme or for a restriction enzyme) on the opposite side of the target region.

It will be evident that one round of amplification can employ a nicking endonuclease and intramolecular ligation to produce the circular progeny nucleic acid, while a previous and/or a subsequent round employs a restriction endonuclease and ligation to a hairpin adapter as described above. When nicking and restriction endonucleases are employed in different rounds, the rounds can be performed sequentially or concurrently, as desired.

Similarly, all of the methods described herein can be employed in combination with each other, as desired. For example, to produce a circular progeny nucleic acid, one round of amplification can employ a restriction endonuclease and ligation of a resulting product hairpin to a hairpin adapter; a pair of restriction enzymes (or sites for a single enzyme flanking the target region) and ligation of two hairpin adapters to the resulting product fragment; a restriction enzyme and a nicking enzyme whose sites flank the target region, with ligation of a hairpin adapter to one end and ligation of the single-stranded extension created by the nicking enzyme at the other end; a pair of nicking enzymes (or sites for a single nicking enzyme flanking the target region) and ligation of the single-stranded extensions at both ends; or a nicking enzyme and intramolecular ligation of the resulting product hairpin. A subsequent round of amplification can then employ any of the techniques described herein, e.g., a restriction endonuclease or a nicking endonuclease to release product hairpins or a pair of restriction enzymes, a restriction enzyme and a nicking enzyme, or a pair of nicking enzymes to release product fragments (optionally with circularization of the product hairpin or fragment), using the same or different enzyme(s) employed in the first round. Three of these combinations have been described in detail above (releasing product hairpins with a single restriction enzyme in both rounds, releasing product fragments via a pair of restriction enzyme sites flanking the target in both rounds, and releasing product hairpins with a single nicking enzyme in both rounds). From these examples, one of skill will readily be able to select appropriate enzymes and configure the template, primer(s), adapter(s), etc. for the particular combination to be employed.

Release of Product Hairpins or Fragments with Recombinases

Although the previous embodiments have described resolution of the concatameric product with endonucleases, it will be evident that other techniques for resolving the concatamer can be employed. For example, where an endonuclease recognition site and an endonuclease are employed in any of the embodiments described herein, a recombinase recognition site and a site-specific recombinase can instead be employed. Similarly, a transposase and transposase site can be employed. Generally, an enzyme or other agent that breaks a phosphodiester bond in a polynucleotide chain, preferably at a preselected location (e.g., within or near a sequence-specific recognition site for the enzyme or agent) can be employed to resolve the concatamer.

Thus, in one class of embodiments, the double-stranded portion of the template nucleic acid includes at least one recombinase recognition site, for example, a single recombinase recognition site (e.g., proximal to the primer binding site) or a pair of recombinase recognition sites flanking the target region. A variety of suitable recombinases and corresponding recognition sites are known in the art. Examples include, but are not limited to, Cre-lox (Cre recombinase and loxP sites; see, e.g., Huovinen et al. (2011) "Enhanced error-prone RCA mutagenesis by concatamer resolution" Plasmid 66(1):47-51), Flp-FRT (flippase recombinase and FLP recombinase target sequences; see, e.g., Lacroix et al. (2011) "FLP/FRT-mediated conditional mutagenesis in pre-erythrocytic stages of *Plasmodium berghei*" Nature Protocols 6:1412-1428), and zinc finger recombinases (see, e.g., Gaj et al. (2013) "A comprehensive approach to zinc-finger recombinase customization enables genomic targeting in human cells" Nucleic Acids Res. 41:3937-46). Exemplary transposases and corresponding sites are similarly known in the art, e.g., Tn5 (Epicentre® Biotechnologies).

Depending on the particular recombinase system employed and the location and orientation of the recombinase recognition site(s), various strategies for product release can be employed, as will be evident to one of skill. For example, where a pair of recombinase recognition sites (e.g., loxP sites in the same orientation) flank the target region, treatment with the recombinase (e.g., Cre) can produce circular products comprising the target region (and optionally elements such as an origin of replication, selectable marker, etc. such that the circular product is a functional plasmid). As another example, a single recombinase recognition site can be provided proximal to the primer binding site. An oligonucleotide cassette that includes the recombinase recognition site is provided in excess. The cassette can comprise, e.g., two complementary oligonucleotides (with or without overhangs) or a single self-complementary oligonucleotide. Treatment with the recombinase releases product hairpins (in embodiments in which the oligonucleotide cassette has free termini at the appropriate end) or recircularized products (in embodiments in which the oligonucleotide cassette has a hairpin loop at the appropriate end). One of skill will readily be able to select an appropriate enzyme and configure the template, primer(s), oligonucleotide cassette(s), etc. for the particular system to be employed.

Essentially all of the features noted for the methods above apply to these embodiments as well, as relevant, for example, with respect to the polymerase employed, type of target region, additional rounds of amplification, subsequent manipulation (e.g., sequencing) of the amplified target region, number of copies of the target region produced, resolution of hyperbranched structures, selection of reaction conditions, inclusion of purification steps, and/or the like.

Applications

Copies of the target region produced by the methods can be used in essentially any desired application, including but not limited to, nucleic acid sequencing (e.g., template-directed sequencing by synthesis of the target region), molecular cloning, mutagenesis, and SNP detection. The circular progeny nucleic acids produced by the methods are particularly useful in determination of the target region's nucleic acid sequence in real time using the single molecule sequencing techniques described, e.g., in U.S. Pat. Nos. 7,056,661, 7,052,847, 7,033,764 and 7,056,676, the full disclosures of which are incorporated herein by reference in their entirety for all purposes, e.g., to produce redundant sequence information from single molecules as detailed in U.S. Pat. No. 8,153,375. A binding site for the primer to be employed during sequence determination (which can be the same as or different than the primer(s) employed during amplification) can be included in the circular progeny nucleic acid.

Additional details on synthesis, isolation, hybridization, and manipulation of nucleic acids (e.g., to produce primers, adapters, templates, and the like or for subsequent manipulation of progeny nucleic acids) are available in the art. See, e.g., Berger and Kimmel, *Guide to Molecular Cloning Techniques, Methods in Enzymology volume* 152 Academic Press, Inc., San Diego, Calif.; Kaufman et al. (2003) Handbook of Molecular and Cellular Methods in Biology and Medicine Second Edition Ceske (ed) CRC Press; Sambrook et al., *Molecular Cloning—A Laboratory Manual* (3rd Ed.), Vol. 1-3, Cold Spring Harbor Laboratory, Cold Spring Harbor, N.Y., 2000; *Current Protocols in Molecular Biology*, F. M. Ausubel et al., eds., Current Protocols, a joint venture between Greene Publishing Associates, Inc. and John Wiley & Sons, Inc., (supplemented through 2013); and Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York).

Amplification of Repetitive Sequences

As noted, strand-displacing polymerases can amplify even targets including short tandem repeated sequences without changing the copy number. Accordingly, in one aspect the invention provides methods of amplifying such targets. In the methods, a nucleic acid template comprising the target region is provided. The template can initially be, e.g., single-stranded, double-stranded, or partially single-stranded and partially double-stranded. At least one primer complementary to a portion of the template is provided, bound to a strand of the template, and extended by a strand-displacing polymerase. Cycles of primer binding and extension can be repeated to achieve the desired degree of amplification of the target region.

The template can be a circular nucleic acid template, e.g., configured as described above, and rolling circle amplification can be performed as detailed above. As another example, the template can be a double-stranded linear template. A pair of primers flanking the target region to be amplified is provided. One primer is complementary to each strand of the template. The template is denatured, typically by increasing the temperature of the reaction mixture, and the primers are bound to the template, e.g., upon reduction of the reaction temperature. The primers are extended. The process can be repeated, using the double-stranded products from one cycle as templates in the next cycle. See, e.g., U.S. Pat. No. 4,965,188. Where the strand-displacing polymerase loses activity upon heating of the reaction mixture, fresh polymerase can be added, e.g., after the reaction temperature is reduced in each cycle. Addition of fresh polymerase is optionally automated.

The target region optionally includes at least five tandem copies of a mononucleotide (i.e., homonucleotide), dinucleotide, trinucleotide, tetranucleotide, or pentanucleotide repeat sequence, e.g., at least 10, at least 20, at least 30, at least 40, at least 50, at least 60, at least 70, at least 80, at least 90, at least 100, at least 150, at least 200, or at least 250 copies of the repeat sequence. Even targets containing large numbers of tandem repeats can be accurately amplified by a high fidelity, error correcting, and highly processive strand-displacing polymerase, for example, by a Φ29-type or a recombinant Φ29-type polymerase.

Random Mutagenesis

Although highly accurate amplification is desirable for many applications (for example, amplification of templates for nucleic acid sequencing), in other applications the introduction of mutations (e.g., targeted or random mutations) is desirable. For example, a random mutagenesis procedure can be used to introduce mutations into enzymes to alter their function. PCR-based amplification methods are commonly used for random mutagenesis, but the exponential nature of product amplification tends to over-represent mutations created in early cycles and under-represent mutations created in late cycles. Rolling circle amplification avoids these issues by repeatedly using the original template to produce copies. This method has been used to mutagenize plasmids (see, e.g., Fujii et al. (2004) "One-step random mutagenesis by error-prone rolling circle amplification" Nucl. Acids Res. 32 (19): e145 and Huovinen et al. (2011) "Enhanced error-prone RCA mutagenesis by concatamer resolution" Plasmid 66(1):47-51). However, rolling circle mutagenesis of an entire plasmid is not ideal, since cloning and expression vectors contain important elements such as origins of replication and antibiotic resistance genes that must be maintained for function but some of the resulting mutant plasmids will include undesired mutations in such essential elements. In one aspect, the invention provides methods that overcome these difficulties by facilitating random mutagenesis of a target region.

To introduce one or more mutations at random sites within a target region, rolling circle amplification of the target region can be performed using any of the methods described herein. In one or more round of amplification, polymerase-mediated template-directed primer extension is performed under mutagenic conditions, resulting in misincorporation errors in the concatameric product. The concatameric product is resolved as detailed above, e.g., to release product hairpins or product fragments that are optionally ligated into a cloning or expression vector or employed in essentially any other application where random nucleotide changes are desirable.

Figure 6:
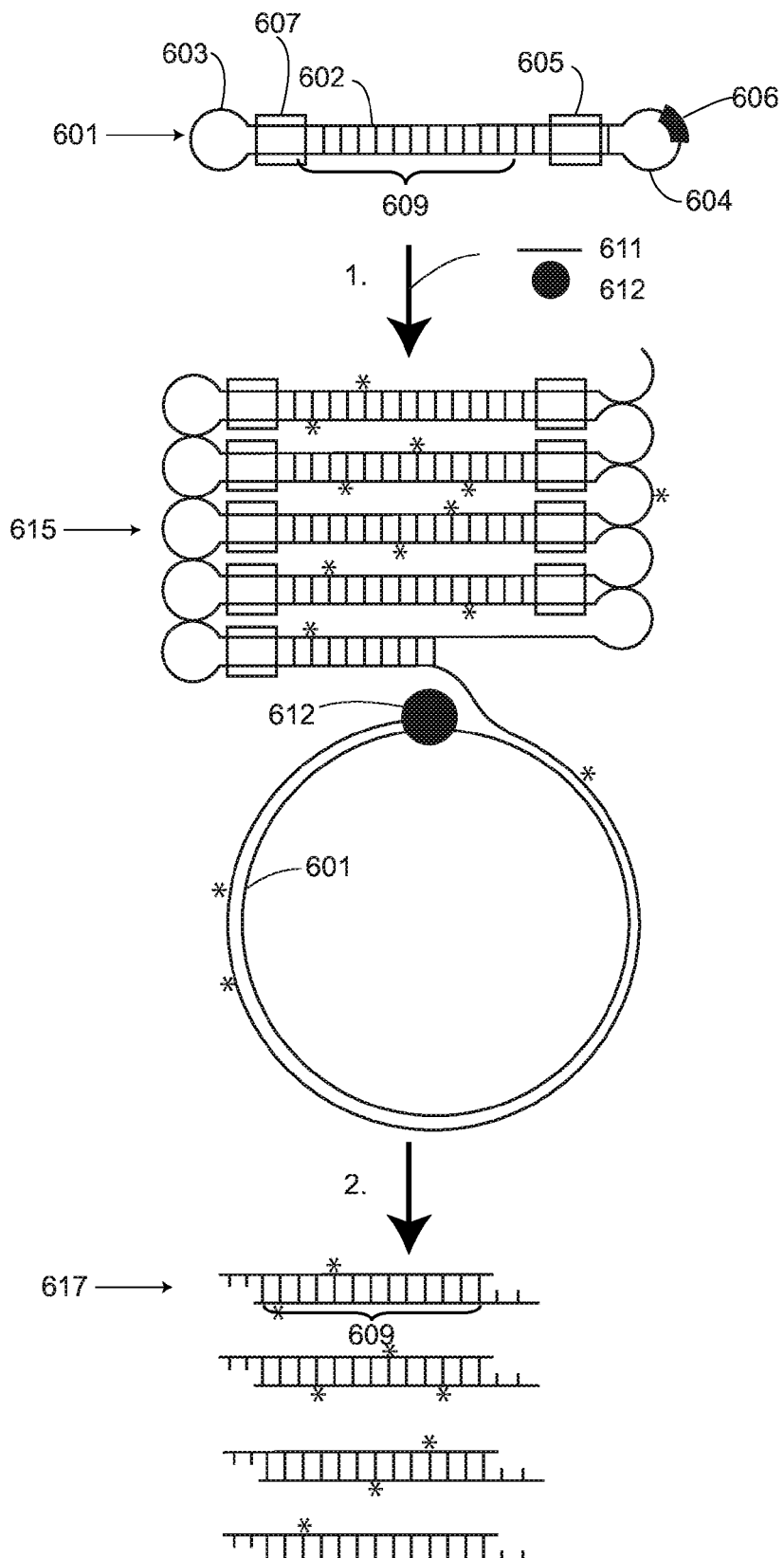
FIG. 6 schematically illustrates an exemplary amplification process in which random mutations are introduced into the target region.

The mutagenesis process for a template in which there is a restriction site on each side of the target region is schematically illustrated in FIG. 6. As shown, nucleic acid template 601 is a circular nucleic acid having double-stranded central region 602 and single-stranded end regions 603 and 604. Double-stranded region 602 includes target region 609. Single-stranded end region 604 includes primer binding sequence 606. Target region 609 is located between recognition sites 605 and 607 for restriction enzymes (the same enzyme or different enzymes).

As illustrated in step 1, template 601 is complexed with primer 611, which binds to primer binding sequence 606, and strand-displacing polymerase 612 in the presence of the four standard nucleotides and/or analogs thereof. Polymerase 612 extends the primer under mutagenic conditions, resulting in misincorporation errors (indicted by stars). As synthesis continues, the polymerase displaces one complementary strand of double-stranded region 602 from the other. Upon completing one full cycle around the template, a double-stranded sequence including original template 601 and the newly synthesized strand results. Synthesis continues around template 601 multiple times as polymerase 612 continues to displace the newly synthesized nascent strand, producing product 615 containing multiple copies of the complement of the template. Self-complementary portions of nascent product strand 615 hybridize to each other as they are displaced by the polymerase, producing long concatenated hairpin structures. Since they are copies of template 601, the double-stranded portions of the concatenated hairpins formed by the displaced product strand also contain restriction sites 605 and 607. Digestion of product 615 with the restriction enzyme(s) thus releases at least one product fragment 617 including mutations at one or more random sites as shown in step 2. Product fragment 617 can be ligated into a cloning vector or other vector and introduced into a host cell, circularized and employed as a template in another round of rolling circle amplification as detailed herein, replicated to "fix" the mutations (e.g., producing a double-stranded nucleic acid both strands of which bear complementary mutated bases), and/or employed in essentially any other desired application.

Any of a variety of mutagenic conditions can be employed during primer extension. For example, primer extension can be performed in a manganese-doped extension buffer. See, e.g., Fujii et al. (2004) "One-step random mutagenesis by error-prone rolling circle amplification" Nucl. Acids Res. 32 (19): e145 and Fujii et al. (2006) "Error-prone rolling circle amplification: the simplest random mutagenesis protocol" Nature Protocols 1:2493-2497. As another example, a low fidelity polymerase can be employed, e.g., a wild-type polymerase inherently having low fidelity, or a polymerase bearing mutations that decrease fidelity. A variety of suitable polymerases are available in the art, including, but not limited to, a Φ29 polymerase lacking 3'-5' exonuclease activity and/or including a mutation such as H61R. As another example, unequal nucleotide concentrations can be employed. As yet another example, at least one mutagenic nucleotide analog that base pairs with two or more different bases can be employed. A variety of suitable mutagenic nucleotide analogs are known in the art, including, but not limited to, 8-Oxo-dGTP, dPTP, 5Br-dUTP, 2OH-dATP, and dITP. It will be evident that combinations of such components (e.g., various mutagenic analogs, $Mn^{2+}$, and/or the like), as well as factors such as template concentration or the like, can be employed in achieving the desired mutagenic conditions.

Primer extension conditions can be varied to adjust mutation frequency as desired. For example, mutation rate can be varied from 1 to 20 nucleotide changes per kb or more (e.g., 1-5 mutations per kb) or to produce an average of at least one nucleotide change per copy of the target region (e.g., 1-5, 1-10, 1-20, 1-30, or more).

Compositions, Systems, and Kits

Compositions, kits, and systems related to, produced by, or of use in the methods are another feature of the invention. For example, one general class of embodiments provides a composition that includes a nucleic acid template, which template is a circular nucleic acid having a double-stranded central region and two single-stranded hairpin end regions and comprising a first primer binding sequence, a first primer that is complementary to the first primer binding sequence, and a polymerase, preferably a polymerase that has strand displacement activity. The double-stranded central region of the template comprises a first polynucleotide sequence and a second polynucleotide sequence complementary to the first polynucleotide sequence. These first and second polynucleotide sequences collectively comprise a target region, and generally also comprise a recognition site for a first site-specific endonuclease. The composition optionally includes the first endonuclease. The composition can also include a first nucleic acid product comprising at least two copies of the first polynucleotide sequence and the second polynucleotide sequence, at least one copy of each of which is not base paired to the template, and/or a first product hairpin having at least one single-stranded hairpin end region, a double-stranded region that comprises the target region, a free 5' terminus, and a free 3' terminus. The composition optionally includes a ligase. The composition can also include one or more nucleotides and/or nucleotide analogs, buffer, salts, metal ions, and the like as known in the art.

In one class of embodiments, the first endonuclease is a restriction endonuclease. In this class of embodiments, the composition can also include a first hairpin adapter suitable for ligation to the product hairpin. For example, the first product hairpin can include a single-stranded overhang on the end opposite to the single-stranded hairpin end region, and the first hairpin adapter can have a single-stranded overhang that is complementary to the single-stranded overhang on the first product hairpin. Optionally, the nucleic acid template is not subject to cleavage by the first restriction endonuclease; for example, the nucleic acid template can be suitably methylated or include a nonstandard nucleotide or backbone linkage. Similarly, the hairpin adapter can be methylated or otherwise modified, whereby the product of ligating the hairpin adapter to the first product hairpin is not subject to cleavage by the first restriction endonuclease.

The composition can include a first circular progeny nucleic acid that is the product of ligating the hairpin adapter to the first product hairpin. Optionally, the first circular progeny nucleic acid comprises a second primer binding sequence, and can also include a recognition site for a second endonuclease, e.g., a nicking endonuclease or a second restriction endonuclease. The second primer binding sequence can be identical to or different from the first primer binding sequence. In one class of embodiments, the first hairpin adapter comprises the second primer binding sequence. As described above, the binding site for the second primer can be formed by ligation of the adapter to the product hairpin. Accordingly, in one class of embodiments, the second primer binding sequence comprises the recognition site for the first restriction endonuclease. The recognition site for the second restriction endonuclease can be identical to the recognition site for the first restriction endonuclease and the first and second restriction endonucleases can be the same enzyme, or the first and second restriction endonucleases can be different enzymes having different recognition sites.

The composition can also include the second primer, second endonuclease, a second hairpin adapter, a second nucleic acid product comprising at least two copies of the first polynucleotide sequence and the second polynucleotide sequence, at least one copy of each of which is not base paired to the first circular progeny nucleic acid, a second product hairpin, and/or a second circular progeny nucleic acid.

In one class of embodiments, the first endonuclease is a nicking endonuclease. The composition can include a first circular progeny nucleic acid that is the product of intramolecularly ligating the 5' and 3' termini of the first product hairpin to each other. Optionally, the first circular progeny nucleic acid comprises a second primer binding sequence. The second primer binding sequence can be the same as, or more typically, different from the first primer binding sequence. The first circular progeny nucleic acid optionally includes a recognition site for a second endonuclease, e.g., a restriction enzyme or a second nicking endonuclease. The recognition site for the second nicking endonuclease can be identical to the recognition site for the first nicking endonuclease and the first and second nicking endonucleases can be the same enzyme, or the first and second nicking endonucleases can be different enzymes having different recognition sites. As described above, the binding site for the second primer can be formed by ligation of the product hairpin. Accordingly, in one class of embodiments, the second primer binding sequence comprises the recognition site for the first nicking endonuclease.

The composition can also include the second primer, second endonuclease, a second nucleic acid product comprising at least two copies of the first polynucleotide sequence and the second polynucleotide sequence, at least one copy of each of which is not base paired to the first circular progeny nucleic acid, a second product hairpin, and/or a second circular progeny nucleic acid.

The polymerase included in the composition can be any of those described herein. For example, in one class of embodiments, the polymerase is a recombinant Φ29-type polymerase, e.g., a recombinant DNA polymerase comprising an amino acid sequence that is at least 80% identical to SEQ ID NO:1 or at least 80% identical to SEQ ID NO:2.

Essentially all of the features noted for the methods above apply to the composition embodiments as well, as relevant; for example, with respect to the configuration of the nucleic acid template, type of target region, inclusion of an exonuclease and/or additional endonucleases, inclusion of at least one mutagenic nucleotide analog and/or $Mn^{2+}$, and the like.

One general class of embodiments provides a composition that includes a nucleic acid template. The template is a circular nucleic acid having a double-stranded central region and two single-stranded hairpin end regions. The double-stranded central region comprises a first polynucleotide sequence and a second polynucleotide sequence complementary to the first polynucleotide sequence, which first and second polynucleotide sequences collectively comprise a target region, a recognition site for a first restriction endonuclease, and a recognition site for a second restriction endonuclease, which recognition sites flank the target region. The circular nucleic acid template also comprises a first primer binding sequence.

The composition also includes a first primer that is complementary to the first primer binding sequence, a polymerase comprising strand displacement activity, and a first nucleic acid product comprising at least two copies of the first polynucleotide sequence and the second polynucleotide sequence, at least one copy of each of which is not base paired to the template. The composition can also include the first endonuclease, the second endonuclease, and a first product fragment having a double-stranded region that comprises the target region. The composition optionally includes a ligase.

In one class of embodiments, the recognition site for the second restriction endonuclease has the same sequence as the recognition site for the first restriction endonuclease, and the first and second restriction endonucleases are the same enzyme. In another class of embodiments, the recognition site for the second restriction endonuclease is different from the recognition site for the first restriction endonuclease, and the first and second restriction endonucleases are different enzymes.

The composition can also include one or more hairpin adapters suitable for ligating to the first product fragment. For example, the composition can include a first hairpin adapter having a single-stranded overhang that is complementary to a single-stranded overhang on one end of the product fragment and a second hairpin adapter having a single-stranded overhang that is complementary to a single-stranded overhang on the other end of the product fragment. Optionally, the nucleic acid template is not subject to cleavage by the first and second restriction endonucleases; for example, the nucleic acid template can be suitably methylated or include a nonstandard nucleotide or backbone linkage. Similarly, the first and second hairpin adapters can be methylated or otherwise modified, whereby the product of ligating the hairpin adapters to the first product fragment is not subject to cleavage by the first and second restriction endonucleases.

The composition can include a first circular progeny nucleic acid that is the product of ligating the first and second hairpin adapters to the first product fragment. Optionally, the first circular progeny nucleic acid comprises a second primer binding sequence, and can also include a recognition site for a third restriction endonuclease and a recognition site for a fourth restriction endonuclease, which sites flank the target region. The second primer binding sequence can be identical to or different from the first primer binding sequence. In one class of embodiments, the first or second hairpin adapter comprises the second primer binding sequence. In one class of embodiments, the second primer binding sequence comprises the recognition site for the first or second restriction endonuclease.

In one class of embodiments, the recognition site for the third restriction endonuclease has the same sequence as the recognition site for the fourth restriction endonuclease, and the third and fourth restriction endonucleases are the same enzyme. In another class of embodiments, the recognition site for the third restriction endonuclease is different from the recognition site for the fourth restriction endonuclease, and the third and fourth restriction endonucleases are different enzymes. The third and fourth enzymes and sites can be the same as the first and second enzymes and sites, different than the first and second enzymes and sites, or a combination thereof.

The composition can also include a second nucleic acid product comprising at least two copies of the first polynucleotide sequence and the second polynucleotide sequence, at least one copy of each of which is not base paired to the first circular progeny nucleic acid. The composition can also include the second primer, third and fourth restriction enzymes, a second product fragment, third and fourth hairpin adapters, a second circular progeny nucleic acid, and the like. The composition can also include one or more nucleotides and/or nucleotide analogs, buffer, salts, metal ions, and the like as known in the art.

Essentially all of the features noted for the methods above apply to the compositions as well, as relevant; for example, with respect to the configuration of the nucleic acid template, type of target region, type of polymerase, inclusion of at least one mutagenic nucleotide analog and/or $Mn^{2+}$, and the like.

Another general class of embodiments provides a composition that includes a strand-displacing polymerase, e.g., one of the Φ29-type polymerases described herein, e.g., a recombinant Φ29 or M2Y polymerase bearing one or more mutation and/or exogenous feature (e.g., a C-terminal polyhistidine tag). Optionally, the polymerase is at least 70% identical to wild-type Φ29 polymerase (SEQ ID NO:1), for example, at least 80%, at least 85%, at least 90%, at least 95%, at least 98%, or even at least 99% identical to wild-type Φ29 polymerase (SEQ ID NO:1). As another example, the polymerase is optionally at least 70% identical to wild-type M2Y polymerase (SEQ ID NO:2), for example, at least 80%, at least 85%, at least 90%, at least 95%, at least 98%, or even at least 99% identical to wild-type M2Y polymerase (SEQ ID NO:2).

The composition can also include a template, e.g., a circular nucleic acid template as described above, a primer, an endonuclease, a ligase, a concatameric nucleic acid product, a hairpin adapter, a product hairpin, and/or a progeny nucleic acid. The composition can also include one or more nucleotides and/or nucleotide analogs, buffer, salts, metal ions, and the like as known in the art. Essentially all of the features noted for the methods above apply to the composition embodiments as well, as relevant; for example, with respect to the configuration of the nucleic acid template, type of target region, type of endonuclease, inclusion of an exonuclease and/or additional endonucleases, inclusion of at least one mutagenic nucleotide analog and/or $Mn^{2+}$, and the like.

The present invention also features kits that facilitate performance of the methods of the invention. The kits include useful reagents such as a strand-displacing polymerase as described herein, one or more adapter (e.g., a pair of stem-loop adapters for constructing a circular template nucleic acid, a hairpin adapter for ligating to a product hairpin or product fragment, etc.), one or more primer (e.g., for extension during amplification of the target or for subsequent sequencing of the target), a ligase, an endonuclease (e.g., a restriction or nicking endonuclease), an exonuclease, and/or the like. Depending upon the desired application, the kits of the invention optionally include additional reagents, such as one or more nucleotides or nucleotide analogs, a control template, and other reagents, such as buffer solutions and/or salt solutions, including, e.g., divalent metal ions. Such kits also typically include instructions for use of the compounds and other reagents in accordance with the desired application methods, e.g., nucleic acid amplification, sequencing, and the like.

In one aspect, the invention includes systems, e.g., systems used to practice the methods herein and/or comprising the compositions described herein, optionally in high-throughput mode. The system can include, e.g., a fluid handling element, a fluid containing element, a heat source and/or heat sink for achieving and maintaining a desired reaction temperature, and/or a robotic element that moves other components of the system from place to place as needed (e.g., a multiwell plate handling element).

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or heating and cooling elements). The computer can also receive data from other components of the system, e.g., from a detector, and can interpret the data, provide it to a user in a human readable format, or use that data to initiate further operations, in accordance with any programming by the user.

Strand-Displacing Polymerases

As noted, preferred polymerases for use in the methods and compositions of the invention exhibit strand displacement activity. A variety of strand-displacing polymerase enzymes are known in the art and are readily available. For example, Φ29 DNA polymerase is available from e.g., Epicentre, and Bst polymerase is available from New England Biolabs.

In one aspect, the strand-displacing polymerase is a Φ29-type DNA polymerase. For example, the polymerase can be homologous to a wild-type or an exonuclease deficient Φ29 DNA polymerase, e.g., as described in U.S. Pat. No. 5,001,050, 5,198,543, or 5,576,204. Similarly, the polymerase can be homologous to another Φ29-type DNA polymerase, such as B103, GA-1, PZA, Φ15, BS32, M2Y (also known as M2), Nf, G1, Cp-1, PRD1, PZE, SF5, Cp-5, Cp-7, PR4, PR5, PR722, L17, AV-1, Φ21, or the like. For nomenclature, see also, Meijer et al. (2001) "Φ29 Family of Phages" Microbiology and Molecular Biology Reviews, 65(2):261-287. See, e.g., SEQ ID NO:1 for the amino acid sequence of wild-type Φ29 polymerase, SEQ ID NO:2 for the amino acid sequence of wild-type M2Y polymerase, SEQ ID NO:3 for the amino acid sequence of wild-type B103 polymerase, SEQ ID NO:4 for the amino acid sequence of wild-type GA-1 polymerase, SEQ ID NO:5 for the amino acid sequence of wild-type AV-1 polymerase, and SEQ ID NO:6 for the amino acid sequence of wild-type CP-1 polymerase (Table 5). Optionally, the polymerase is at least 70% identical to wild-type Φ29 polymerase (SEQ ID NO:1), for example, at least 80%, at least 85%, at least 90%, at least 95%, at least 98%, or even at least 99% identical to wild-type Φ29 polymerase (SEQ ID NO:1). As another example, the polymerase is optionally at least 70% identical to wild-type M2Y polymerase (SEQ ID NO:2), for example, at least 80%, at least 85%, at least 90%, at least 95%, at least 98%, or even at least 99% identical to wild-type M2Y polymerase (SEQ ID NO:2).

A wild-type Φ29-type DNA polymerase can be employed in the methods and compositions of the invention or can be used as a starting point for mutation to produce polymerases suitable for use in the methods and compositions. For example, appropriate mutations to improve stability, increase readlength, and/or alter another desirable property as described herein can be introduced into the polymerase.

In addition to wild-type polymerases, chimeric polymerases made from a mosaic of different sources can be used. For example, Φ29-type polymerases made by taking sequences from more than one parental polymerase into account can be employed in the methods and compositions or used as a starting point for mutation to produce polymerases suitable for use in the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2Y polymerase, a B103 polymerase, and a GA-1 polymerase, can be generated. Appropriate mutations to increase readlength, improve thermostability, or the like as described herein can be introduced into the chimeras.

Available DNA polymerase enzymes have also been modified in any of a variety of ways, e.g., to reduce or eliminate exonuclease activities (many native DNA polymerases have a proof-reading exonuclease function), to simplify production by making protease digested enzyme fragments such as the Klenow fragment recombinant, etc. Polymerases have also been modified to increase readlength and stability (e.g., U.S. patent application 61/708,469 filed Oct. 1, 2012 by Satwik Kamtekar et al. and entitled "Recombinant Polymerases with Increased Readlength and Stability for Single-Molecule Sequencing" and U.S. patent application Ser. No. 14/042,255 filed Sep. 30, 2013 by Satwik Kamtekar et al. and entitled "Recombinant Polymerases with Increased Readlength and Stability for Single-Molecule Sequencing"), to confer improvements in specificity, processivity, and retention time of labeled nucleotides in polymerase-DNA-nucleotide complexes (e.g., WO 2007/076057 "Polymerases for Nucleotide Analogue Incorporation" by Hanzel et al. and WO 2008/051530 "Polymerase Enzymes and Reagents for Enhanced Nucleic Acid Sequencing" by Rank et al.), to alter branching fraction and translocation (e.g., US patent application publication 2010-0075332 by Pranav Patel et al. entitled "Engineering Polymerases and Reaction Conditions for Modified Incorporation Properties"), to increase photostability (e.g., US patent application publication 2010-0093555 "Enzymes Resistant to Photodamage" by Keith Bjornson et al. and U.S. patent application Ser. No. 13/756,113 filed Jan. 31, 2013 by Satwik Kamtekar et al. and entitled "Recombinant Polymerases with Increased Phototolerance"), to slow one or more catalytic steps during the polymerase kinetic cycle, increase closed complex stability, decrease branching fraction, alter cofactor selectivity, and increase yield, thermostability, accuracy, speed, and readlength (e.g., US patent application publication 2010-0112645 "Generation of Modified Polymerases for Improved Accuracy in Single Molecule Sequencing" by Sonya Clark et al., US patent application publication 2011-0189659 "Generation of Modified Polymerases for Improved Accuracy in Single Molecule Sequencing" by Sonya Clark et al., and US patent application publication 2012-0034602 "Recombinant Polymerases For Improved Single Molecule Sequencing" by Robin Emig et al.), and to improve surface-immobilized enzyme activities (e.g., WO 2007/075987 Active Surface Coupled Polymerases by Hanzel et al. and WO 2007/075873 Protein Engineering Strategies to Optimize Activity of Surface Attached Proteins by Hanzel et al.). Any of these available polymerases can be employed in or modified to be suitable for use in the methods and compositions of the invention.

Φ29-type polymerases described in U.S. patent application 61/708,469 filed Oct. 1, 2012 by Satwik Kamtekar et al. and entitled "Recombinant Polymerases with Increased Readlength and Stability for Single-Molecule Sequencing," U.S. patent application Ser. No. 14/042,255 filed Sep. 30, 2013 by Satwik Kamtekar et al. and entitled "Recombinant Polymerases with Increased Readlength and Stability for Single-Molecule Sequencing," and US patent application publication 2013-0217007 entitled "Recombinant Polymerases with Increased Phototolerance" (each of which is incorporated herein by reference in its entirety) as suitable for use in whole genome amplification can be employed in the methods and compositions of the invention. As described in U.S. patent applications Ser. No. 61/708,469 and 14/042,255, mutations that enhance stability of the polymerase, of a binary complex including the polymerase and a primer and template, and/or of a ternary complex including the polymerase, a primer and template, and a nucleotide or nucleotide analog can be employed. Exemplary thermal inactivation assays for assessing polymerase stability or stability of a binary complex including the polymerase, a gapped duplex DNA substrate bearing a fluorophore and a quencher, and a cognate nucleotide triphosphate or nucleotide analog are described in U.S. patent applications Ser. No. 61/708,469 and 14/042,255. An exemplary thermal inactivation assay in which the stability of a ternary complex including the polymerase, a gapped duplex DNA substrate, and a cognate nucleotide or nucleotide analog is assessed is described in US patent application publication 2012-0034602. Various mutations that can be introduced into a polymerase to increase polymerase, binary complex, and/or ternary complex stability are also described in U.S. patent applications 61/708,469 and Ser. No. 14/042,255 and US patent application publication 2012-0034602. Employing a polymerase having higher stability can, e.g., permit amplification to be performed at a higher temperature, which can be advantageous for targets including regions of secondary structure.

As a few examples, a polymerase for use in the methods and compositions (e.g., a Φ29-type polymerase) optionally includes one or more mutations that enhance stability (e.g., polymerase stability, binary complex stability, and/or ternary complex stability). Thus, the polymerase can include, e.g., one or more substitutions that increase binary complex stability, e.g., D570E, Y148I, and/or K131E, where identification of positions is relative to SEQ ID NO:1. The polymerase can include one or more substitutions that increase stability and/or yield of the free polymerase, e.g., Y224K, E239G, and/or F526L, providing combinations such as K131E, Y148I, Y224K, and D570E, where identification of positions is relative to SEQ ID NO:1. The polymerase can be derived from an M2Y parental polymerase, optionally a C-terminal H is 10 tagged M2Y polymerase, to enhance stability. The polymerase can include a substitution that can enhance its ability to read through sites of DNA damage, e.g., L253A, providing combinations such as K131E, Y148I, Y224K, L253A, and D570E, where identification of positions is relative to SEQ ID NO:1. Further exemplary polymerase mutations and/or combinations thereof are provided in Tables 3 and 4 hereinbelow. The noted mutation(s) can be introduced into a wild-type or mutant Φ29 polymerase, a wild-type or mutant M2Y polymerase, or another Φ29-type polymerase as noted herein. Optionally, the resulting modified recombinant polymerase is at least 70% identical to wild-type Φ29 polymerase (SEQ ID NO:1), for example, at least 80%, at least 85%, at least 90%, at least 95%, at least 98%, or even at least 99% identical to wild-type Φ29 polymerase (SEQ ID NO:1). As another example, the resulting modified recombinant polymerase is optionally at least 70% identical to wild-type M2Y polymerase (SEQ ID NO:2), for example, at least 80%, at least 85%, at least 90%, at least 95%, at least 98%, or even at least 99% identical to wild-type M2Y polymerase (SEQ ID NO:2). Such polymerases can be employed, e.g., in the amplification methods and compositions described herein.

The polymerase optionally includes one or more features exogenous or heterologous to the polymerase. For example, the recombinant polymerase optionally includes one or more tags, e.g., purification, substrate binding, or other tags, such as a polyhistidine tag, a His10 tag, a His6 tag, an alanine tag, an Ala10 tag, an Ala16 tag, a biotin tag, a biotin ligase recognition sequence or other biotin attachment site (e.g., a BiTag or a Btag or variant thereof, e.g., BtagV1-11), a GST tag, an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a plurality of polyhistidine tags, a plurality of His10 tags, a plurality of His6 tags, a plurality of alanine tags, a plurality of Ala10 tags, a plurality of Ala16 tags, a plurality of biotin tags, a plurality of GST tags, a plurality of BiTags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, an antibody or antibody domain, antibody fragment, antigen, receptor, receptor domain, receptor fragment, maltose binding protein, ligand, one or more protease site (e.g., Factor Xa, enterokinase, or thrombin site), a dye, an acceptor, a quencher, a DNA binding domain (e.g., a helix-hairpin-helix domain from topoisomerase V), a domain that binds modified bases (e.g., an MeCpG binding protein 2 domain, an 06-alkylguanine DNA alkyl transferase domain, a thymine dioxygenase JBP1 catalytic domain, or an SRA domain, e.g., from UHRF1), a sliding clamp domain or the like to increase affinity for DNA (e.g., an HSV UL42 domain), or combination thereof. See, e.g., US patent application publication 2012-0034602 for sequences of a number of suitable tags and linkers, including BtagV1-11; see also U.S. patent applications Ser. No. 61/708,469 and 14/042,255 for sequences of additional exogenous features. The feature "topo V fusion" indicates that the polymerase includes a fusion as described in de Vega et al. (2010) "Improvement of tp29 DNA polymerase amplification performance by fusion of DNA binding motifs" Proc Natl Acad Sci USA 107:16506-16511. The one or more exogenous or heterologous features can find use not only for purification purposes, immobilization of the polymerase to a substrate, and the like, but can also be useful for altering one or more properties of the polymerase (e.g., addition of an exogenous feature at the C-terminus (e.g., a His10 or other polyhistidine tag), can decrease exonuclease activity and/or increase binary and/or ternary complex stability).

The one or more exogenous or heterologous features can be included internal to the polymerase, at the N-terminal region of the polymerase, at the C-terminal region of the polymerase, or at a combination thereof (e.g., at both the N-terminal and C-terminal regions of the polymerase). Where the polymerase includes an exogenous or heterologous feature at both the N-terminal and C-terminal regions, the exogenous or heterologous features can be the same (e.g., a polyhistidine tag, e.g., a His10 tag, at both the N- and C-terminal regions) or different (e.g., a biotin ligase recognition sequence at the N-terminal region and a polyhistidine tag, e.g., His10 tag, at the C-terminal region). Optionally, a terminal region (e.g., the N- or C-terminal region) of a polymerase of the invention can comprise two or more exogenous or heterologous features which can be the same or different (e.g., a biotin ligase recognition sequence and a polyhistidine tag at the N-terminal region, a biotin ligase recognition sequence, a polyhistidine tag, and a Factor Xa recognition site at the N-terminal region, and the like). As a few examples, the polymerase can include a polyhistidine tag at the C-terminal region, a biotin ligase recognition sequence at the N-terminal region and a polyhistidine tag at the C-terminal region, a biotin ligase recognition sequence and a polyhistidine tag at the N-terminal region, a biotin ligase recognition sequence and a polyhistidine tag at the N-terminal region and a polyhistidine tag at the C-terminal region, two biotin ligase recognition sequences at the C-terminal region (e.g., two tandem sequences, e.g., tandem Btags), or a polyhistidine tag and a biotin ligase recognition sequence at the C-terminal region.

For convenience, an exogenous or heterologous feature will often be expressed as a fusion domain of the overall polymerase protein, e.g., as a conventional in-frame fusion of a polypeptide sequence with the active polymerase enzyme (e.g., a polyhistidine tag fused in frame to an active polymerase enzyme sequence). However, features such as tags can be added chemically to the polymerase, e.g., by using an available amino acid residue of the enzyme or by incorporating an amino acid into the protein that provides a suitable attachment site for the coupling domain. Suitable residues of the enzyme can include, e.g., histidine, cysteine, or serine residues (providing for N, S, or O linked coupling reactions). Optionally, one or more cysteines present in the parental polymerase (e.g., up to all of the cysteines present on the polymerase's surface) can be replaced with a different amino acid; either a single reactive surface cysteine can be left unsubstituted or a single reactive surface cysteine can be introduced in place of another residue, for convenient addition of a feature, e.g., for surface immobilization through thiol labeling (e.g., addition of maleimide biotin, or maleimide and an alkyne for click labeling). Unnatural amino acids that comprise unique reactive sites can also be added to the enzyme, e.g., by expressing the enzyme in a system that comprises an orthogonal tRNA and an orthogonal synthetase that loads the unnatural amino acid in response to a selector codon.

A list of exemplary polymerase mutation combinations, and optional corresponding exogenous or heterologous features at the N- and/or C-terminal region of the polymerase, is provided in Tables 3 and 4. Although the mutations and/or exogenous features listed in Tables 3 and 4 can be introduced into an otherwise wild-type Φ29 or M2Y polymerase, the mutations, combinations of mutations, and features shown in Tables 3 and 4 are not limited to use in a Φ29 or M2Y polymerase. For example, essentially any of these mutations, any combination of these mutations, and/or any combination of these mutations with the other mutations disclosed or referenced herein can be introduced into a polymerase (e.g., a Φ29-type polymerase) to produce a modified recombinant polymerase in accordance with the invention. Such a polymerase is optionally at least 70% identical to wild-type Φ29 polymerase (SEQ ID NO:1) or wild-type M2Y polymerase (SEQ ID NO:2), for example, at least 80%, at least 85%, at least 90%, at least 95%, at least 98%, or even at least 99% identical to wild-type Φ29 polymerase (SEQ ID NO:1) or wild-type M2Y polymerase (SEQ ID NO:2).

Positions of amino acid substitutions are identified relative to a wild-type Φ29 DNA polymerase (SEQ ID NO:1) for the recombinant polymerases in Table 3 and relative to a wild-type M2Y DNA polymerase (SEQ ID NO:2) for the recombinant polymerases in Table 4. Polymerases of the invention (including those provided in Tables 3 and 4) can include any exogenous or heterologous feature (or combination of such features), e.g., at the N- and/or C-terminal region. For example, it will be understood that polymerase mutants in Tables 3 and 4 that do not include, e.g., a C-terminal His10 tag can be modified to include a polyhistidine tag at the C-terminal region, alone or in combination with any of the exogenous or heterologous features described herein. Similarly, some or all of the exogenous features listed in Tables 3 and 4 can be omitted, or substituted or combined with any of the other exogenous features described herein, and still result in a polymerase of the invention. As will be appreciated, the numbering of amino acid residues is with respect to a particular reference polymerase, such as the wild-type sequence of the Φ29 polymerase (SEQ ID NO:1) or M2Y polymerase (SEQ ID NO:2); actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

TABLE 3

Exemplary mutations and/or exogenous features introduced into a Φ29 DNA polymerase. Positions are identified relative to SEQ ID NO: 1.

| N-terminal region feature(s) | Mutations | C-terminal region feature(s) |
|---|---|---|
|  |  | His10 |
|  | K131E | His10 |
|  | Y148I | His10 |
|  | Y224K | His10 |
|  | D570E | His10 |
|  | K131E Y148I Y224K D570E | His10 |
|  | L253A | His10 |
| BtagV7 His10 | V250I L253A |  |
| BtagV7 His10 | Y224K F526L |  |
| BtagV7 His10 | F526L |  |
| BtagV7 His10 | Y224K E239G A484E E515K F526L |  |
| BtagV7 His10 | Y224K E239G A484E F526L |  |
| BtagV7 His10 | Y224K E239G F526L |  |
| BtagV7 His10 | Y224K E239G E515K F526L |  |
| BtagV7 His10 | Y224K E239G A484E K512Y E515K F526L |  |
| BtagV7 His10 | Y224K E239G K512Y E515K F526L |  |
| Btag His10 | F309S |  |
| Btag His10 | F309S Y310H |  |
| Btag His10 | F309H |  |
| Btag His10 | F309R |  |
| Btag His10 | T368F |  |
| Btag His10 | Q171E E175R |  |
| Btag His10 | V276E W277K H284Y |  |
| Btag His10 | G217P |  |
| Btag His10 | Y343R |  |
| Btag His10 | V222I |  |
| Btag His10 | T368G |  |
| Btag His10 | T368Y |  |
|  |  | 576GTGSGA 696-802 topoV fusion |
|  |  | 576GTGSGA 696-751 topoV fusion |
|  | L253H A437G K135Q |  |

TABLE 4

Exemplary mutations and/or exogenous features introduced into an M2Y DNA polymerase. Positions are identified relative to SEQ ID NO: 2.

| Mutations | C-terminal region feature(s) |
|---|---|
|  | His10 |
| E236G | His10 |
| V247I | His10 |
| A434G | His10 |
| S253A | His10 |
| D507K | His10 |
| E512Q | His10 |
| K128E | His10 |
| Y145I | His10 |
| K128E Y145I | His10 |

TABLE 5

Amino acid sequence of exemplary wild-type Φ29-type polymerases and of an M2Y polymerase bearing a C-terminal His10 tag.

Φ29 SEQ ID NO: 1
MKHMPRKMYSCDFETTTKVEDCRVWAYGYMNIEDHSEYKIG
NSLDEFMAWVLKVQADLYFHNLKFDGAFIINWLERNGFKWS
ADGLPNTYNTIISRMGQWYMIDICLGYKGKRKIHTVIYDSL
KKLPFFPVKKIAKDFKLTVLKGDIDYHKERPVGYKITPEEYA
YIKNDIQIIAEALLIQFKQGLDRMTAGSDSLKGFKDIITTK
KFKKVFPTLSLGLDKEVRYAYRGGFTWLNDRFKEKEIGEGM
VFDVNSLYPAQMYSRLLPYGEPIVFEGKYVWDEDYPLHIQH
IRCEFELKEGYIPTIQIKRSRFYKGNEYLKSSGGEIADLWL
SNVDLELMKEHYDLYNVEYISGLKFKATTGLFKDFIDKWTY
IKTTSEGAIKQLAKLMLNSLYGKFASNPDVTGKVPYLKENG
ALGFRLGEEETKDPVYTPMGVFITAWARYTTITAAQACYDR
IIYCDTDSIHLTGTEIPDVIKDIVDPKKLGYWAHESTFKRA
KYLRQKTYIQDIYMKEVDGKLVEGSPDDYTDIKFSVKCAGM
TDKIKKEVTFENFKVGFSRKMKPKPVQVPGGVVLVDDTFTI
K

M2Y SEQ ID NO: 2
MSRKMFSCDFETTTKLDDCRVWAYGYMEIGNLDNYKIGNSL
DEFMQWVMEIQADLYFHNLKFDGAFIVNWLEQHGFKWSNEG
LPNTYNTIISKMGQWYMIDICFGYKGKRKLHTVIYDSLKKL
PFPVKKIAKDFQLPLLKGDIDYHTERPVGHEITPEEYEYIK
NDIEIIARALDIQFKQGLDRMTAGSDSLKGFKDILSTKKFN
KVFPKLSLPMDKEIRKAYRGGFTWLNDKYKEKEIGEGMVFD
VNSLYPSQMYSRPLPYGAPIVFQGKYEKDEQYPLYIQRIRF
EFELKEGYIPTIQIKKNPFFKGNEYLKNSGVEPVELYLTNV
DLELIQEHYELYNVEYIDGKFREKTGLFKDFIDKWTYVKT
HEEGAKKQLAKLMLNSLYGKFASNPDVTGKVPYLKDDGSLG
FRVGDEEYKDPVYTPMGVFITAWARFTTITAAQACYDRIIY
CDTDSIHLTGTEVPEIIKDIVDPKKLGYWAHESTFKRAKYL
RQKTYIQDIYVKEVDGKLKECSPDEATTTKFSVKCAGMTDT
IKKKVTFDNFAVGFSSMGKPKPVQVNGGVVLVDSVFTIK

B103 SEQ ID NO: 3
MPRKMFSCDFETTTKLDDCRVWAYGYMEIGNLDNYKIGNSL
DEFMQWVMEIQADLYFHNLKFDGAFIVNWLEHHGFKWSNEG
LPNTYNTIISKMGQWYMIDICFGYKGKRKLHTVIYDSLKKL
PFPVKKIAKDFQLPLLKGDIDYHAERPVGHEITPEEYEYIK
NDIEIIARALDIQFKQGLDRMTAGSDSLKGFKDILSTKKFN
KVFPKLSLPMDKEIRRAYRGGFTWLNDKYKEKEIGEGMVFD
VNSLYPSQMYSRPLPYGAPIVFQGKYEKDEQYPLYIQRIRF
EFELKEGYIPTIQIKKNPFFKGNEYLKNSGAEPVELYLTNV
DLELIQEHYEMYNVEYIDGKFREKTGLFKEFIDKWTYVKT
HEKGAKKQLAKLMFDSLYGKFASNPDVTGKVPYLKEDGSLG
FRVGDEEYKDPVYTPMGVFITAWARFTTITAAQACYDRIIY
CDTDSIHLTGTEVPEIIKDIVDPKKLGYWAHESTFKRAKYL
RQKTYIQDIYAKEVDGKLIECSPDEATTTKFSVKCAGMTDT
IKKKVTFDNFRVGFSSTGKPKPVQVNGGVVLVDSVFTIK

GA-1 SEQ ID NO: 4
MARSVYVCDFETTTDPEDCRLWAWGWMDIYNTDKWSYGEDI
DSFMEWALNSNSDIYFHNLKFDGSFILPWWLRNGYVHTEED
RTNTPKEFTTTISGMGQWYAVDVCINTRGKNKNHVVFYDSL
KKLPFKVEQIAKGFGLPVLKGDIDYKKYRPVGYMDDNEIE
YLKHDLLIVALALRSMFDNDFTSMTVGSDALNTYKEMLGVK
QWEKYFPVLSLKVNSEIRKAYKGGFTWVNPKYQGETVYGGM
VFDVNSMYPAMMKNKLLPYGEPVMFKGEYKKNVEYPLYIQQ

TABLE 5-continued

Amino acid sequence of exemplary wild-type
φ29-type polymerases and of an M2Y
polymerase bearing a C-terminal His10 tag.

|  |  |
|---|---|
| | VRCELKKDKIPCIQIKGNARFGQNEYLSTSGDEYVDLYVTN<br>VDWELIKKHYDIFEEEFIGGFMFKGFIGFFDEYIDRFMEIK<br>NSPDSSAEQSLQAKLMLNSLYGKFATNPDITGKVPYLDENG<br>VLKFRKGELKERDPVYTPMGCFITAYARENILSNAQKLYPR<br>FIYADTDSIHVEGLGEVDAIKDVIDPKKLGYWDHEATFQRA<br>RYVRQKTYFIETTWKENDKGKLVVCEPQDATKVKPKIACAG<br>MSDAIKERIRFNEFKIGYSTHGSLKPKNVLGGVVLMDYPFA<br>IK |
| AV-1<br>SEQ ID<br>NO: 5 | MVRQSTIASPARGGVRRSHKKVPSFCADFETTTDEDDCRVW<br>SWGIIQVGKLQNYVDGISLDGFMSHISERASHIYFHNLAFD<br>GTFILDWLLKHGYRWTKENPGVKEFTSLISRMGKYYSITVV<br>FETGFRVEFRDSFKKLPMSVSAIAKAFNLHDQKLEIDYEKP<br>RPIGYIPTEQEKRYQRNDVAIVAQALEVQFAEKMTKLTAGS<br>DSLATYKKMTGKLFIRRFPILSPEIDTEIRKAYRGGFTYAD<br>PRYAKKLNGKGSVYDVNSLYPSVMRTALLPYGEPIYSEGAP<br>RTNRPLYIASITFTAKLKPNHIPCIQIKKNLSFNPTQYLEE<br>VKEPTTVVATNIDIELWKKHYDFKIYSWNGTFEFRGSHGFF<br>DTYVDHFMEIKKNSTGGLRQIAKLHLNSLYGKFATNPDITG<br>KHPTLKDNRVSLVMNEPETRDPVYTPMGVFITAYARKKTIS<br>AAQDNYETFAYADTDSLHLIGPTTPPDSLWVDPVELGAWKH<br>ESSFTKSVYIRAKQYAEEIGGKLDVHIAGMPRNVAATLTLE<br>DMLHGGTWNGKLIPVRVPGGTVLKDTTFTLKID |
| CP-1<br>SEQ ID<br>NO: 6 | MTCYYAGDFETTTNEEETEVWLSCFAKVIDYDKLDTFKVNT<br>SLEDFLKSLYLDLDKTYTETGEDEFIIFFHNLKFDGSFLLS<br>FFLNNDIECTYFINDMGVWYSITLEFPDFTLTFRDSLKILN<br>FSIATMAGLFKMPIAKGTTPLLKHKPEVIKPEWIDYIHVDV<br>AILARGIFAMYYEENFTKYTSASEALTEFKRIFRKSKRKFR<br>DFFPILDEKVDDFCRKHIVGAGRLPTLKHRGRTLNQLIDIY<br>DINSMYPATMLQNALPIGIPKRYKGKPKEIKEDHYYIYHIK<br>ADFDLKRGYLPTIQIKKKLDALRIGVRTSDYVTTSKNEVID<br>LYLTNFDLDLFLKHYDATIMYVETLEFQTESDLFDDYITTY<br>RYKKENAQSPAEKQKAKIMLNSLYGKFGAKIISVKKLAYLD<br>DKGILRFKNDDEEEVQPVYAPVALFVTSIARHFIISNAQEN<br>YDNFLYADTDSLHLFHSDSLVLDIDPSEFGKWAHEGRAVKA<br>KYLRSKLYIEELIQEDGTTHLDVKGAGMTPEIKEKITFENF<br>VIGATFEGKRASKQIKGGTLIYETTFKIRETDYLV |
| M2Y.His10<br>SEQ ID<br>NO: 7 | MSRKMFSCDFETTTKLDDCRVWAYGYMEIGNLDNYKIGNSL<br>DEFMQWVMEIQADLYEHNLKEDGAFIVNWLEQHGEKWSNEG<br>LPNTYNTIISKMGQWYMIDICFGYKGKRKLHTVIYDSLKKL<br>PFPVKKIAKDFQLPLLKGDIDYHTERPVGHEITPEEYEYIK<br>NDIEIIARALDIQFKQGLDRMTAGSDSLKGEKDILSTKKEN<br>KVFPKLSLPMDKEIRKAYRGGFTWLNDKYKEKEIGEGMVED<br>VNSLYPSQMYSRPLPYGAPIVPQGKYEKDEQYPLYIQRIRF<br>EFELKEGYIPTIQIKKNPFFKGNEYLKNSGVEPVELYLTNV<br>DLELIQEHYELYNVEYIDGEKFREKTGLEKDFIDKWTYVKT<br>HEEGAKKQLAKLMLNSLYGKFASNPDVTGKVPYLKDDGSLG<br>FRVGDEEYKDPVYTPMGVFITAWARFTTITAAQACYDRIIY<br>CDTDSIHLTGTEVPEIIKDIVDPKKLGYWAHESTFKRAKYL<br>RQKTYIQDIYVKEVDGKLKECSPDEATTTKESVKCAGMTDT<br>IKKKVTEDNFAVGESSMGKPKPVQVNGGVVLVDSVFTIKGH<br>HHHHHHHHHH |

Mutating Polymerases

In general, any available mutagenesis procedure can be used for making polymerase mutants. Such mutagenesis procedures optionally include selection of mutant nucleic acids and polypeptides for one or more activity of interest (e.g., increased thermostability, increased readlength, increased accuracy, and/or the like). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified in the references above.

Additional information on mutation formats is found in: Sambrook et al., *Molecular Cloning—A Laboratory Manual* (3rd Ed.), Vol. 1-3, Cold Spring Harbor Laboratory, Cold Spring Harbor, N.Y., 2000; *Current Protocols in Molecular Biology*, F. M. Ausubel et al., eds., Current Protocols, a joint venture between Greene Publishing Associates, Inc. and John Wiley & Sons, Inc., (supplemented through 2013); and *PCR Protocols A Guide to Methods and Applications* (Innis et al. eds) Academic Press Inc. San Diego, Calif. (1990).

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found hereinabove and, e.g., in WO 2007/076057 "Polymerases for Nucleotide Analogue Incorporation" by Hanzel et al. and WO 2008/051530 "Polymerase Enzymes and Reagents for Enhanced Nucleic Acid Sequencing" by Rank et al. Additional useful references for mutation, recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols, Second Edition* (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

Nucleic acids encoding the recombinant polymerases of the invention are also a feature of the invention. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids of the invention are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuj a ed., *Handbook of Bioseparations*, Academic Press (2000).

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence (other than residues noted, e.g., in Tables 3-4 or elsewhere herein, as being relevant to a feature or property of interest) are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution."

TABLE 6

Conservative amino acid substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine Alanine Valine Leucine Isoleucine Proline | Serine Threonine Cysteine Methionine Asparagine Glutamine | Phenylalanine Tyrosine Tryptophan | Lysine Arginine Histidine | Aspartate Glutamate |

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 75%, 80%, 90%, 95%, 97%, 98%, or 99% or more identity, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2012).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Amplification of Trinucleotide Repeats by Φ29-Type Polymerases

Recombinant polymerases based on Φ29 or M2Y polymerase are expressed and purified as described below. The polymerases are used to amplify a target region including either 30 CGG repeats or 95 CGG repeats. Each of the five polymerases tested is able to amplify both target regions while maintaining trinucleotide repeat copy number.

Polymerase Preparation

The phi29 and M2Y polymerase genes are cloned into pET11 (Novagen). Primers for specified mutations are designed and introduced into the gene using the Phusion Hot Start DNA Polymerase Kit (New England Biolabs). A PCR reaction is performed to incorporate mutations and product is purified using ZR-96 DNA Clean and Concentration Kits (Zymo Research). PCR products are digested with NdeI/BamHI and ligated into the vector. Plasmids are transformed into TOP10 *E. coli* competent cells, plated on selective media and incubated at 37° C. overnight. Colonies are selected and plasmid is purified using Qiagen miniprep kits. Plasmids are then sequenced (Sequetech).

Plasmid containing the recombinant polymerase gene is transformed into BL21 Star21 CDE3+Biotin Ligase cells (Invitrogen) using heat shock. Transformed cells are grown in selective media overnight at 37° C. 200A of the overnight culture are diluted into 4 mL of Overnight Express Instant TB Medium (EMD Chemicals) supplemented with biotin, glycerol, and antibiotics and grown at 37° C. until controls reach O.D. value of 4-6. Cultures are then incubated at 18° C. for 16 hours. Following this incubation, cells are harvested, resuspended in lysis buffer, and frozen at −80° C. Cells are thawed. The resulting lysate is centrifuged and supernatant is collected. Polymerase is purified over nickel followed by heparin columns. The resulting proteins are run on gels and quantified by SYPRO® staining.

Five polymerases are tested: polymerase A (SEQ ID NO:7), M2Y; polymerase B, Φ29 with a D570E substitution; polymerase C, Φ29 with K131E, Y148I, Y224K, and D570E substitutions; polymerase D, Φ29 with a Y224K substitution; and polymerase E, Φ29. All five polymerases have a C-terminal His10 tag. Positions of substitutions in Φ29 are identified relative to SEQ ID NO:1.

Amplification of Trinucleotide Repeats

Two circular nucleic acid templates with double-stranded central regions and single-stranded hairpin end regions (SMRTbells™) are prepared. One includes 30 CGG repeats from the FMR1 gene in the double-stranded central region of the template; the other includes 95 CGG repeats. The SMRTbells™ are created using a C1 hairpin adapter (pATCTCTCTCttttcctcctcctccgttgttgttgttGAGAGAGAT, SEQ ID NO:8) at both ends.

A polymerization reaction is run for each of the five polymerases with each of the two templates (one possessing 30 CGG repeats and the other 95 CGG repeats). Amplification reactions are prepared using 1x Thermo Scientific reaction buffer (33 mM Tris-acetate, 10 mM Mg-acetate, 66 mM K-acetate, 0.1% (v/v) Tween 20, 1 mM DTT), 400 µM (each) dNTPs, 15 ng SMRTbell™, and 300 nM of 3' phosphorothiolated C1 sequencing primer (5000:1 primer:template), in a 40 µL reaction volume. The sequence of the C1 primer is AACGGAGGAGGAGGA (SEQ ID NO:9). SMRTbells™ are prepared for amplification by heating to 80° C. for 2 minutes, and then slow cooling by 0.1° C. per second to 30° C. 200 ng of each mutant polymerase is immediately added in separate reactions, and the samples are incubated for 21 hours at 30° C. Reactions are cleaned using 1× volume pre-washed Agencourt Ampure XP Magnetic beads (Beckman Coulter) according to the manufacturer's specifications. Samples are eluted in 40 µL of Elution Buffer (10 mM Tris-HCl, pH 8.5; Qiagen) and quantitated using a NanoDrop 1000 Spectrophotometer.

Figure 5:
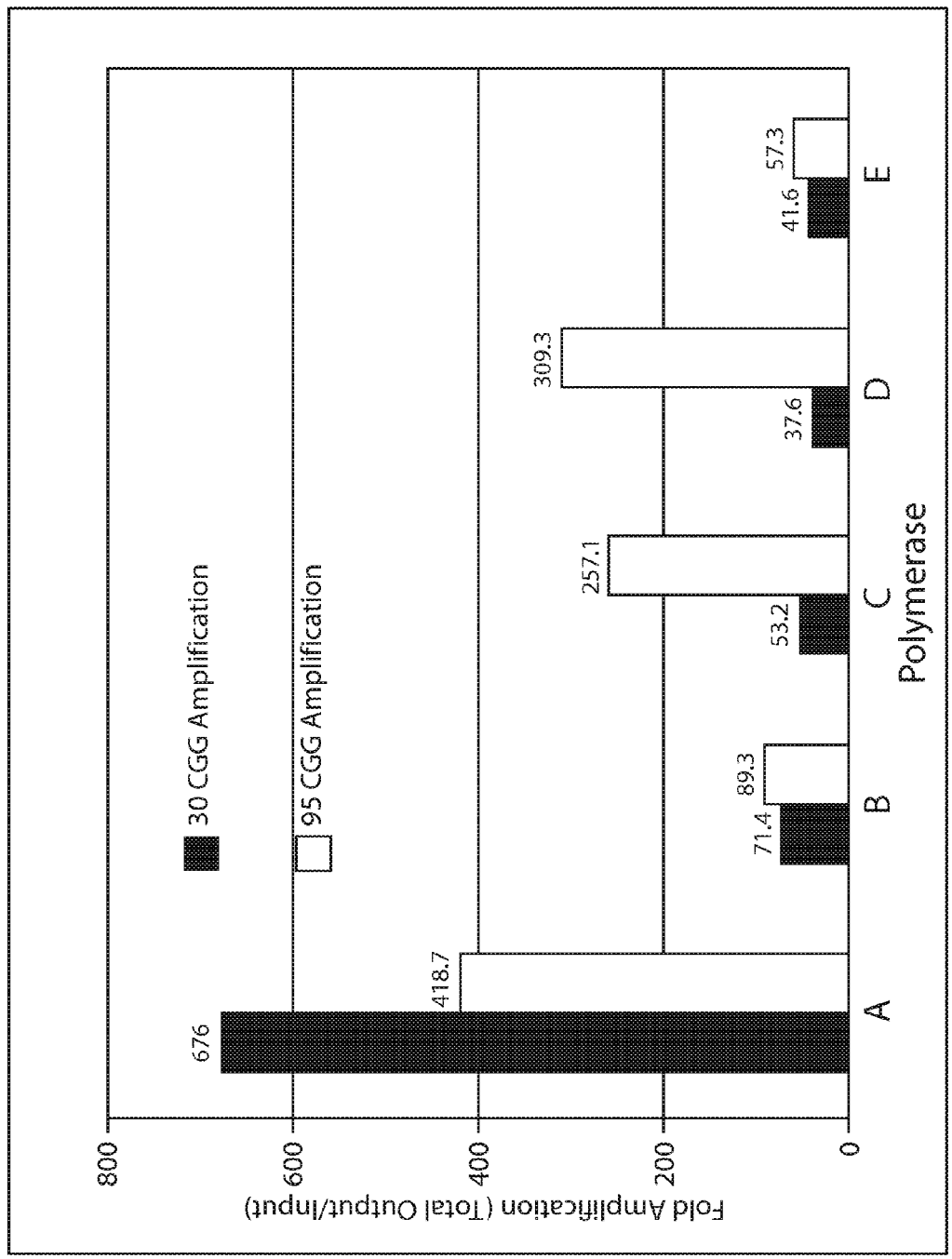
FIG. 5 presents a bar graph showing the fold amplification demonstrated by different Φ29-type polymerases for two targets, one including 30 CGG trinucleotide repeats and the other including 95 CGG trinucleotide repeats.

As shown in FIG. 5, each of the polymerases is able to amplify both the 30 CGG trinucleotide repeat target and the 95 CGG trinucleotide repeat target. Amplification ranges from about 40 fold to about 700 fold for the shorter target region, and from about 60 fold to about 400 fold for the longer target region.

To verify that the amplified products contain the expected number of repeats, 500 ng of each product is digested with 40 units PstI for three hours at 37° C. Products are visualized on an ethidium bromide stained 1% agarose gel, and expected insert sizes (572 by for 30 CGG target and 767 by for 95 CGG target) are observed.

Example 2

Amplification of Fmr1 from Genomic DNA Through Two Rounds of Targeted Rolling Circle Amplification FMR1 is amplified from genomic DNA using two sequential rounds of targeted rolling circle amplification, as follows. 20 µg genomic DNA (including ~7 pg FMR1) is digested with BsaI and BstAPI for six hours at 50-55° C. (expected fragment size 1.3 kb). Overnight ligation with a pair of hairpin adapters is performed. One hairpin adapter is blunt ended, and the other has a single-stranded overhang complementary to that produced on the FMR1 fragment by BstAPI. At least one of the adapters is tagged to assist in purification of products that include the adapter. Either the adapter includes a biotin moiety (e.g., a biotinylated base), or the adapter includes a polyA sequence in its loop to which a biotinylated poly-dT oligo binds.

After ligation of the hairpin adapters to the FMR1 BsaI/BstAPI fragment to produce a circular SMRTbell™ is complete, the ligase is inactivated. Uncircularized nucleic acids (e.g., off-target nucleic acids) are removed by treating with exonuclease for two hours. The FMR1 SMRTbell™ is protected from exonuclease digestion, since it has no free termini. The reaction is cleaned with Ampure beads. The first SMRTbell™ including the FMR1 BsaI/BstAPI fragment is isolated with streptavidin beads through binding to the biotin tagged adapter, then eluted in distilled water.

The FMR1 target region is amplified using the first SMRTbell™ as a template with polymerase A (purified as described in Example 1). The reaction is cleaned with Ampure beads. The product of this first round of amplification is digested with BsmAI and XmaI (expected fragment size 0.96 kb). The resulting BsmAI/XmaI fragment is circularized by ligation of a pair of hairpin adapters to its ends to produce a second SMRTbell™. One adapter is blunt ended, and one has a single-stranded overhang complementary to that produced on the FMR1 fragment by XmaI. Uncircularized nucleic acids are removed by treating with exonuclease. The reaction is cleaned with Ampure beads. The second SMRTbell™ is then used as a template in a second round of amplification with polymerase A.

Amplified FMR1 product is detectable after the second round of amplification, with a yield of 188 ng. Amplification is estimated to be an average of 177 fold in each of the two rounds.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of amplifying a nucleic acid target region, the method comprising:
   a) providing a nucleic acid template, which template is a circular nucleic acid having a double-stranded central region and two single-stranded hairpin end regions; wherein the double-stranded central region comprises a first polynucleotide sequence and a second polynucleotide sequence complementary to the first polynucleotide sequence, which first and second polynucleotide sequences collectively comprise the target region, a recognition site for a first restriction endonuclease, and a recognition site for a second restriction endonuclease, which recognition sites flank the target region; and wherein the circular nucleic acid comprises a first primer binding sequence;
   b) binding a first primer to the first primer binding sequence;
   c) performing polymerase-mediated template-directed primer extension of the first primer with a polymerase comprising strand displacement activity, thereby producing a first nucleic acid product comprising at least two copies of the first polynucleotide sequence and the second polynucleotide sequence, at least one copy of each of which is not base paired to the template;
   d) digesting the first product with the first and second restriction endonucleases and releasing at least one first product fragment having a double-stranded region that comprises the target region, and
   e) ligating a first hairpin adapter to one end of the first product fragment and ligating a second hairpin adapter to the other end of the first product fragment, thereby producing at least one first circular progeny nucleic acid.

2. The method of claim 1, wherein step d) is performed concurrently with step c).

3. The method of claim 1, wherein step e) is performed concurrently with step d).

4. The method of claim 1, wherein steps c), d), and e) are performed concurrently.

5. The method of claim 1, comprising performing template-directed sequencing by synthesis on at least a portion of the target region in the first circular progeny nucleic acid.

6. A method of amplifying a nucleic acid target region, the method comprising:
   a) providing a nucleic acid template, which template is a circular nucleic acid having a double-stranded central region and two single-stranded hairpin end regions; wherein the double-stranded central region comprises a first polynucleotide sequence and a second polynucleotide sequence complementary to the first polynucleotide sequence, which first and second polynucleotide sequences collectively comprise the target region and a recognition site for a first site-specific endonuclease; and wherein the circular nucleic acid comprises a first primer binding sequence;
   b) binding a first primer to the first primer binding sequence;
   c) performing polymerase-mediated template-directed primer extension of the first primer with a polymerase comprising strand displacement activity, thereby producing a first nucleic acid product comprising at least two copies of the first polynucleotide sequence and the second polynucleotide sequence, at least one copy of each of which is not base paired to the template;
   d) cutting the first product with the first endonuclease and releasing at least one first product hairpin having at least one single-stranded hairpin end region, a double-stranded region that comprises the target region, a free 5' terminus, and a free 3' terminus; and
   e) circularizing the at least one first product hairpin, thereby producing at least one first circular progeny nucleic acid.

7. The method of claim 6, wherein the recognition site for the first endonuclease is proximal to the first primer binding sequence in the template.

8. The method of claim 6, wherein the first endonuclease is a restriction endonuclease, and wherein circularizing the at least one first product hairpin comprises ligating a first hairpin adapter to the first product hairpin.

9. The method of claim 8, wherein the first circular progeny nucleic acid comprises a second primer binding sequence and a recognition site for a second restriction endonuclease, the method comprising:
   without denaturing the first circular progeny nucleic acid, binding a second primer to the second primer binding sequence;
   performing polymerase-mediated template-directed primer extension of the second primer with a polymerase comprising strand displacement activity, thereby producing a second nucleic acid product comprising at least two copies of the complement of the first copy nucleic acid, at least one copy of which is not base paired to the first circular progeny nucleic acid;
   digesting the second product with the second restriction endonuclease and releasing at least one second product hairpin having one single-stranded hairpin end region and a double-stranded region that comprises the target region; and
   ligating a second hairpin adapter to the second product hairpin, thereby producing at least one second circular progeny nucleic acid.

10. The method of claim 9, wherein the first hairpin adapter comprises the second primer binding sequence.

11. The method of claim 9, wherein the second primer binding sequence is formed by ligation of the first hairpin adapter to the first product hairpin.

12. The method of claim 9, wherein the primer extension, digesting, and ligating steps to produce the first circular progeny nucleic acid and the primer extension, digesting, and ligating steps to produce the second circular progeny nucleic acid are performed in a single reaction mixture.

13. The method of claim 8, wherein the first hairpin adapter has a single-stranded overhang that is complementary to a single-stranded overhang on the first product hairpin.

14. The method of claim 8, wherein the cleavage site for the first restriction endonuclease is within the target region.

15. The method of claim 6, wherein the first endonuclease is a nicking endonuclease, and wherein circularizing the at least one first product hairpin comprises ligating the 5' terminus of the first product hairpin intramolecularly to the 3' terminus.

16. The method of claim 1, wherein the first circular progeny nucleic acid comprises a second primer binding sequence, a recognition site for a third restriction endonuclease, and a recognition site for a fourth restriction endonuclease, which recognition sites flank the target region, the method comprising:
   without denaturing the first circular progeny nucleic acid, binding a second primer to the second primer binding sequence;
   performing polymerase-mediated template-directed primer extension of the second primer with a polymerase comprising strand displacement activity, thereby producing a second nucleic acid product comprising at least two copies of the first polynucleotide sequence and the second polynucleotide sequence, at least one copy of each of which is not base paired to the first circular progeny nucleic acid; and
   digesting the second product with the third and fourth endonucleases and releasing at least one second product fragment having a double-stranded region that comprises the target region.

17. The method of claim 16, wherein the first or second hairpin adapter comprises the second primer binding sequence.

18. The method of claim 16, wherein the second primer binding sequence is formed by ligation of the first or second hairpin adapter to the first product fragment.

19. The method of claim 1, wherein the first primer binding sequence is in one of the two single-stranded hairpin end regions in the template.

20. The method of claim 1, wherein the nucleic acid template and/or the first circular progeny nucleic acid is not subject to being cut by the first endonuclease.

21. The method of claim 1, wherein the target region comprises at least five tandem copies of a mononucleotide, dinucleotide, trinucleotide, tetranucleotide, or pentanucleotide repeat sequence.

* * * * *